(12) United States Patent
Connor

(10) Patent No.: US 9,968,297 B2
(45) Date of Patent: May 15, 2018

(54) EEG GLASSES (ELECTROENCEPHALOGRAPHIC EYEWEAR)

(71) Applicant: Robert A. Connor, St. Paul, MN (US)

(72) Inventor: Robert A. Connor, St. Paul, MN (US)

(73) Assignee: Medibotics LLC, St. Paul, MN (US)

( * ) Notice: Subject to any disclaimer, the term of this patent is extended or adjusted under 35 U.S.C. 154(b) by 0 days. days.

(21) Appl. No.: 15/464,349

(22) Filed: Mar. 21, 2017

(65) Prior Publication Data

US 2017/0188947 A1 Jul. 6, 2017

Related U.S. Application Data

(63) Continuation-in-part of application No. 15/136,948, filed on Apr. 24, 2016, and a continuation-in-part of application No. 14/562,719, filed on Dec. 7, 2014, and a continuation-in-part of application No. 14/330,649, filed on Jul. 14, 2014, said application No. 15/136,948 is a continuation-in-part of application No. 14/599,522, filed on Jan. 18, 2015, which is a continuation-in-part of application No. 14/562,719, filed on Dec. 7, 2014, said application No. 14/330,649 is a continuation-in-part of application No. 13/797,955, filed on Mar. 12, 2013, now Pat. No. 9,456,916, and a continuation-in-part of application No. 13/523,739, filed on Jun. 14, 2012, now Pat. No. 9,042,596.

(60) Provisional application No. 62/430,667, filed on Dec. 6, 2016, provisional application No. 62/322,594, filed on Apr. 14, 2016, provisional application No. 62/303,126, filed on Mar. 3, 2016, provisional application No. 62/169,661, filed on Jun. 2, 2015, provisional application No. 62/160,172, filed on May 12, 2015, provisional application No. 62/089,696, filed on Dec. 9, 2014, provisional application No.
(Continued)

(51) Int. Cl.
| | |
|---|---|
| *A61B 5/04* | (2006.01) |
| *A61B 5/00* | (2006.01) |
| *A61B 5/0476* | (2006.01) |

(52) U.S. Cl.
CPC .......... *A61B 5/6803* (2013.01); *A61B 5/0006* (2013.01); *A61B 5/0476* (2013.01)

(58) Field of Classification Search
CPC .... A61B 5/6803; A61B 5/0006; A61B 5/0476
See application file for complete search history.

(56) References Cited

U.S. PATENT DOCUMENTS

| | | | | |
|---|---|---|---|---|
| 5,606,458 A | * | 2/1997 | Fergason | ........... G02B 27/0172 359/630 |
| 7,344,244 B2 | | 3/2008 | Goodall et al. | |

(Continued)

*Primary Examiner* — Tiffany Weston
*Assistant Examiner* — Tho Tran

(57) ABSTRACT

This invention comprises EEG glasses (electroencephalographic eyewear) with a side section of an eyewear frame which spans forward and upward onto a portion of the person's forehead and then curves back downward to connect to the front section of the eyewear frame. These EEG glasses (electroencephalographic eyewear) further include a flexible protrusion which is attached to the side section and an electromagnetic energy sensor which collects data concerning electromagnetic brain activity, wherein the flexible protrusion holds the electromagnetic energy sensor.

1 Claim, 25 Drawing Sheets

Related U.S. Application Data

62/017,615, filed on Jun. 26, 2014, provisional application No. 61/939,244, filed on Feb. 12, 2014, provisional application No. 61/932,517, filed on Jan. 28, 2014, provisional application No. 61/729,494, filed on Nov. 23, 2012.

(56) References Cited

U.S. PATENT DOCUMENTS

| | | |
|---|---|---|
| 7,390,088 B2 | 6/2008 | Goodall et al. |
| 7,486,988 B2 | 2/2009 | Goodall et al. |
| 8,244,342 B2 | 8/2012 | Goodall et al. |
| 8,346,354 B2 | 1/2013 | Hyde et al. |
| 8,467,133 B2 | 6/2013 | Miller |
| 8,472,120 B2 | 6/2013 | Border et al. |
| 8,477,425 B2 | 7/2013 | Border et al. |
| 8,482,859 B2 | 7/2013 | Border et al. |
| 8,488,246 B2 | 7/2013 | Border et al. |
| 8,562,540 B2 | 10/2013 | Goodall et al. |
| 2006/0252978 A1 | 11/2006 | Vesely et al. |
| 2006/0252979 A1 | 11/2006 | Vesely et al. |
| 2007/0010757 A1 | 1/2007 | Goodall et al. |
| 2007/0019279 A1* | 1/2007 | Goodall ............ A61B 5/04001 359/291 |
| 2007/0106145 A1 | 5/2007 | Kim et al. |
| 2007/0106172 A1* | 5/2007 | Abreu ................ A61B 5/0002 600/549 |
| 2008/0161673 A1 | 7/2008 | Goodall et al. |
| 2011/0028798 A1 | 2/2011 | Hyde et al. |
| 2011/0029038 A1 | 2/2011 | Hyde et al. |
| 2011/0029044 A1 | 2/2011 | Hyde et al. |
| 2011/0221656 A1 | 9/2011 | Haddick et al. |
| 2011/0221669 A1 | 9/2011 | Shams et al. |
| 2011/0221672 A1 | 9/2011 | Osterhout et al. |
| 2011/0222745 A1 | 9/2011 | Osterhout et al. |
| 2011/0227820 A1 | 9/2011 | Haddick et al. |
| 2012/0062445 A1 | 3/2012 | Haddick et al. |
| 2012/0075168 A1 | 3/2012 | Osterhout et al. |
| 2012/0150545 A1 | 6/2012 | Simon |
| 2012/0212398 A1 | 8/2012 | Border et al. |
| 2012/0212400 A1 | 8/2012 | Border et al. |
| 2012/0218172 A1 | 8/2012 | Border et al. |
| 2012/0218301 A1 | 8/2012 | Miller |
| 2012/0235883 A1 | 9/2012 | Border et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0242678 A1 | 9/2012 | Border et al. |
| 2012/0242698 A1 | 9/2012 | Haddick et al. |
| 2013/0056010 A1 | 3/2013 | Walker et al. |
| 2013/0127980 A1 | 5/2013 | Haddick et al. |
| 2013/0242262 A1 | 9/2013 | Lewis |
| 2013/0303837 A1 | 11/2013 | Berka et al. |
| 2013/0314303 A1 | 11/2013 | Osterhout et al. |
| 2014/0023999 A1 | 1/2014 | Greder |
| 2014/0223462 A1 | 8/2014 | Aimone et al. |
| 2014/0267005 A1 | 9/2014 | Urbach |
| 2014/0267401 A1 | 9/2014 | Urbach |
| 2014/0316230 A1 | 10/2014 | Denison et al. |
| 2014/0347265 A1* | 11/2014 | Aimone ................ G09G 3/003 345/156 |
| 2014/0375545 A1 | 12/2014 | Ackerman et al. |
| 2015/0223688 A1* | 8/2015 | Wang .................... A61B 3/152 351/208 |
| 2016/0071390 A1* | 3/2016 | Sales .................... A61B 5/1114 340/573.1 |
| 2016/0256086 A1* | 9/2016 | Byrd ................... A61B 5/0059 |
| 2016/0287173 A1* | 10/2016 | Abreu ................ A61B 5/4821 |

\* cited by examiner

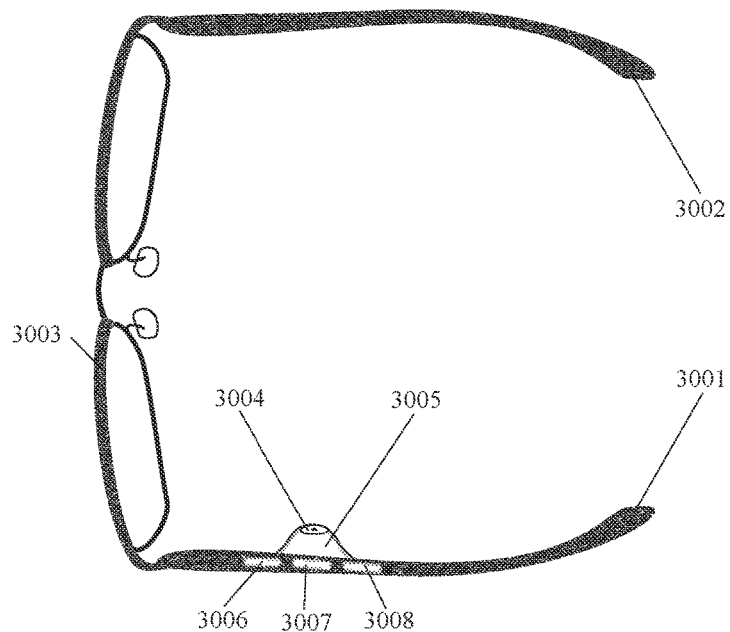
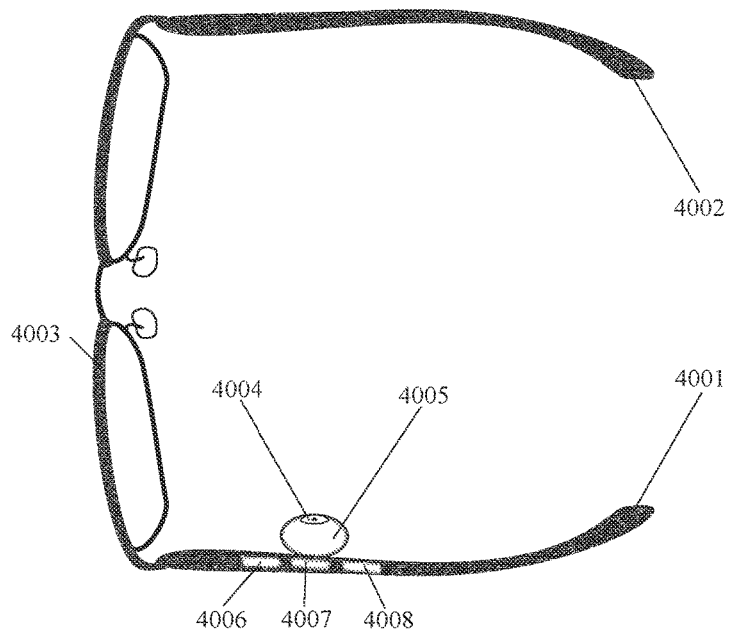

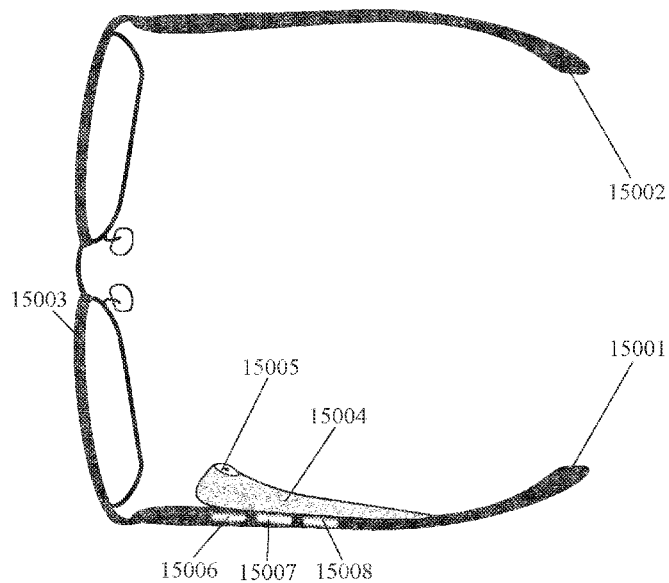
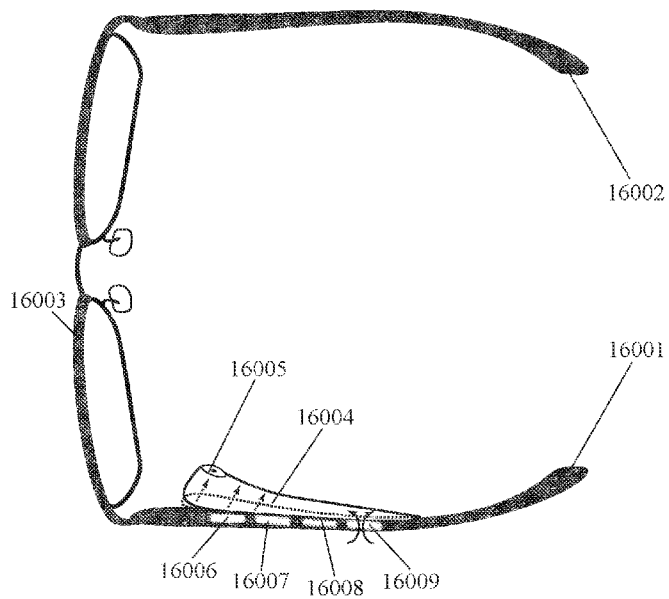

EEG GLASSES (ELECTROENCEPHALOGRAPHIC EYEWEAR)

CROSS-REFERENCE TO RELATED APPLICATIONS

This application:

<1> claims the priority benefit of U.S. Provisional Patent Application 62/430,667 entitled "EEG Glasses and Other Electroencephalographic Eyewear" filed on Dec. 6, 2016;

<2> is a continuation in part of U.S. patent application Ser. No. 14/330,649 entitled "Eyewear System for Monitoring and Modifying Nutritional Intake" filed on Jul. 14, 2014 which, in turn * was a continuation in part of U.S. patent application Ser. No. 13/523,739 entitled "Willpower Watch™—A Wearable Food Consumption Monitor" filed on Jun. 14, 2012, and * was a continuation in part of U.S. patent application Ser. No. 13/797,955 entitled "Device for Selectively Reducing Absorption of Unhealthy Food" filed on Mar. 12, 2013 which claimed the priority benefit of U.S. Provisional Patent Application 61/729,494 entitled "Device for Selectively Reducing Absorption of Unhealthy Food" filed on Nov. 23, 2012;

<3> is a continuation in part of U.S. patent application Ser. No. 14/562,719 entitled "Willpower Glasses™: A Wearable Food Consumption Monitor" filed on Dec. 7, 2014 which, in turn * claimed the priority benefit of U.S. Provisional Patent Application 61/932,517 entitled "Nutrode™: Wearable EEG Monitor for Modifying Food Consumption" filed on Jan. 28, 2014; and <4> is a continuation in part of U.S. patent application Ser. No. 15/136,948 entitled "Wearable and Mobile Brain Computer Interface (BCI) Device and Method" filed on Apr. 24, 2016 which, in turn * was a continuation-in-part of U.S. patent application Ser. No. 14/599,522 entitled "Mobile Wearable Electromagnetic Brain Activity Monitor" with a filing date of Jan. 18, 2015 which, in turn: (1) was a continuation in part of U.S. patent application Ser. No. 14/562,719 entitled "Willpower Glasses™: A Wearable Food Consumption Monitor" with a filing date of Dec. 7, 2014 which claimed the priority benefit of U.S. Provisional Patent Application 61/932,517 entitled "Nutrode™: Wearable EEG Monitor for Modifying Food Consumption" with a filing date of Jan. 28, 2014; (2) claimed the priority benefit of U.S. Provisional Patent Application 61/932,517 entitled "Nutrode™: Wearable EEG Monitor for Modifying Food Consumption" with a filing date of Jan. 28, 2014; (3) claimed the priority benefit of U.S. Provisional Patent Application 61/939,244 entitled "Brainwave-Controlled Eyewear" with a filing date of Feb. 12, 2014; (4) claimed the priority benefit of U.S. Provisional Patent Application 62/017,615 entitled "Nervision™ Integrated Eyewear and EEG Monitor" with a filing date of Jun. 26, 2014; and (5) claimed the priority benefit of U.S. Provisional Patent Application 62/089,696 entitled "Electroencephalographic Eyewear" with a filing date of Dec. 9, 2014; * claimed the priority benefit of U.S. Provisional Patent Application 62/160,172 entitled "Hair-Engaging Mobile Brain Activity Monitor" with a filing date of May 12, 2015; * claimed the priority benefit of U.S. Provisional Patent Application 62/169,661 entitled "Internet of Thinks (IoT): A Brain Computer Interface (BCI) Using EEG Patterns Associated with the Same Command Across Different Action Modes" with a filing date of Jun. 2, 2015; * claimed the priority benefit of U.S. Provisional Patent Application 62/303,126 entitled "Undulating Mobile EEG Monitor Spanning a Portion of the Forehead" with a filing date of Mar. 3, 2016; and * claimed the priority benefit of U.S. Provisional Patent Application 62/322,594 entitled "Halo-Style Mobile Electroencephalographic (EEG) Monitor" with a filing date of Apr. 14, 2016.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to mobile EEG (electroencephalographic) monitoring.

INTRODUCTION

There are many potential applications for a portable wearable device which collects data concerning electromagnetic brain activity such as electroencephalographic (EEG) data. Potential applications include: medical diagnosis during routine ambulatory activities; real-time biofeedback and behavior modification during daily activities; human-to-computer interface for control of external devices by people with impaired muscle control (e.g. due to paralysis or neurological impairment); human-to-computer interface for control of external devices during conditions in which direct mental control of external devices is preferred to manual control; real-time brain activity tracking during sports; and real-time brain activity tracking during hazardous conditions such as combat, rescue, or hostile environmental operations.

Traditional non-portable methods for collecting EEG data generally require a person to be connected to a stationary medical device with wires and to remain in a single location such as a physician's office or hospital room. Such traditional methods do not allow collection of EEG data while a person is ambulatory and/or goes about their normal daily activities. There has been some work toward the design of portable wearable devices for ambulatory collection of data concerning electromagnetic brain activity, but devices in the prior art still tend to be relatively intrusive in appearance and/or prone to shifting with significant body motion. People tend to be particularly sensitive to unusual, bulky, visually-intrusive, or downright dorky devices on their head.

During the past several centuries people have become accustomed to eyeglasses. Accordingly, eyeglasses are a particularly promising platform into which electromagnetic energy sensors can be incorporated. However, traditional eyeglass frames were not designed with the intent of providing contact with a person's forehead for electromagnetic energy sensors. This invention proposes novel designs for eyeglasses (and other eyewear) which bring electromagnetic energy sensors into contact with a person's temple and/or forehead without being too visually intrusive. This invention discloses novel designs for incorporating electromagnetic energy sensors into eyeglasses (or other eyewear) to create "EEG glasses" (electroencephalographic eyewear) which are relatively non-intrusive in appearance and relatively stable during body motion.

Review of the Prior Art

The prior art does disclose "EEG glasses" (electroencephalographic eyewear), but most of it focuses on the optical aspects of eyeglasses and only tangentially mentions the possible addition of an EEG sensor to a conventional eyeglass frame. Conventional eyeglass frames do not contact a person's forehead and are not well-suited for holding one or more electromagnetic brain activity sensors in contact with a person's forehead. The prior art does not appear to disclose the electroencephalographic eyewear designs disclosed herein which are designed to bring electromagnetic brain sensors into contact a person's forehead while being visually non-intrusive and also stable during body motion.

Relevant prior art includes U.S. Pat. No. 7,344,244 (Goodall et al., Mar. 18, 2008, "Adjustable Lens System with Neural-Based Control"), U.S. Pat. No. 7,390,088 (Goodall et al., Jun. 24, 2008, "Adjustable Lens System with Neural-Based Control"), U.S. Pat. No. 7,486,988 (Goodall et al., Feb. 3, 2009, "Method and System for Adaptive Vision Modification"), U.S. Pat. No. 8,244,342 (Goodall et al., Aug. 14, 2012, "Method and System for Adaptive Vision Modification"), U.S. Pat. No. 8,346,354 (Hyde et al., Jan. 1, 2013, "Determining a Neuromodulation Treatment Regimen in Response to Contactlessly Acquired Information"), U.S. Pat. No. 8,467,133 (Miller, Jun. 18, 2013, "See-Through Display with an Optical Assembly Including a Wedge-Shaped Illumination System"), U.S. Pat. No. 8,472,120 (Border et al., Jun. 25, 2013, "See-Through Near-Eye Display Glasses with a Small Scale Image Source"), U.S. Pat. No. 8,477,425 (Border et al., Jul. 2, 2013, "See-Through Near-Eye Display Glasses Including a Partially Reflective, Partially Transmitting Optical Element"), U.S. Pat. No. 8,482,859 (Border et al., Jul. 9, 2013, "See-Through Near-Eye Display Glasses Wherein Image Light Is Transmitted to and Reflected From an Optically Flat Film"), U.S. Pat. No. 8,488,246 (Border et al., Jul. 16, 2013, "See-Through Near-Eye Display Glasses Including a Curved Polarizing Film in the Image Source, a Partially Reflective, Partially Transmitting Optical Element and an Optically Flat Film"), and U.S. Pat. No. 8,562,540 (Goodall et al., Oct. 22, 2013, "Method and System for Adaptive Vision Modification").

Relevant prior art also includes U.S. patent applications: 20060252978 (Vesely et al., Nov. 9, 2006, "Biofeedback Eyewear System"), 20060252979 (Vesely et al., Nov. 9, 2006, "Biofeedback Eyewear System"), 20070010757 (Goodall et al., Jan. 11, 2007, "Method and System for Adaptive Vision Modification"), 20070019279 (Goodall et al., Jan. 25, 2007, "Adjustable Lens System with Neural-Based Control"), 20070106145 (Kim et al., May 10, 2007, "Accessories for Remote Monitoring"), 20080161673 (Goodall et al., Jul. 3, 2008, "Method and System for Adaptive Vision Modification"), 20110028798 (Hyde et al., Feb. 3, 2011, "Electronically Initiating an Administration of a Neuromodulation Treatment Regimen Chosen in Response to Contactlessly Acquired Information"), 20110029038 (Hyde et al., Feb. 3, 2011, "Determining a Neuromodulation Treatment Regimen in Response to Contactlessly Acquired Information"), 20110029044 (Hyde et al., Feb. 3, 2011, "Stimulating a Nervous System Component of a Mammal in Response to Contactlessly Acquired Information"), 20110221656 (Haddick et al., Sep. 15, 2011, "Displayed Content Vision Correction with Electrically Adjustable Lens"), and 20110221669 (Shams et al., Sep. 15, 2011, "Gesture Control in an Augmented Reality Eyepiece").

Relevant prior art also includes U.S. patent applications: 20110221672 (Osterhout et al., Sep. 15, 2011, "Hand-Worn Control Device in an Augmented Reality Eyepiece"), 20110222745 (Osterhout et al., Sep. 15, 2011, "Method and Apparatus for Biometric Data Capture"), 20110227820 (Haddick et al., Sep. 22, 2011, "Lock Virtual Keyboard Position in an Augmented Reality Eyepiece"), 20120062445 (Haddick et al., Mar. 15, 2012, "Adjustable Wrap Around Extendable Arm for a Head-Mounted Display"), 20120075168 (Osterhout et al., Mar. 29, 2012, "Eyepiece with Uniformly Illuminated Reflective Display"), 20120150545 (Simon, Jun. 14, 2012, "Brain-Computer Interface Test Battery for the Physiological Assessment of Nervous System Health"), 20120212398 (Border et al., 823/2012, "See-Through Near-Eye Display Glasses Including a Partially Reflective, Partially Transmitting Optical Element"), and 20120212400 (Border et al., Aug. 23, 2012, "See-Through Near-Eye Display Glasses Including a Curved Polarizing Film in the Image Source, a Partially Reflective, Partially Transmitting Optical Element and an Optically Flat Film").

Relevant prior art also includes U.S. patent applications: 20120218172 (Border et al., Aug. 30, 2012, "See-Through Near-Eye Display Glasses with a Small Scale Image Source"), 20120218301 (Miller, Aug. 30, 2012, "See-Through Display with an Optical Assembly Including a Wedge-Shaped Illumination System"), 20120235883 (Border et al., Sep. 20, 2012, "See-Through Near-Eye Display Glasses with a Light Transmissive Wedge Shaped Illumination System"), 20120235886 (Border et al., Sep. 20, 2012, "See-Through Near-Eye Display Glasses with a Small Scale Image Source"), 20120235887 (Border et al., Sep. 20, 2012, "See-Through Near-Eye Display Glasses Including a Partially Reflective, Partially Transmitting Optical Element and an Optically Flat Film"), and 20120235900 (Border et al., Sep. 20, 2012, "See-Through Near-Eye Display Glasses with a Fast Response Photochromic Film System for Quick Transition From Dark to Clear").

Relevant prior art also includes U.S. patent applications: 20120236030 (Border et al., Sep. 20, 2012, "See-Through Near-Eye Display Glasses Including a Modular Image Source"), 20120242678 (Border et al., Sep. 27, 2012, "See-Through Near-Eye Display Glasses Including an Auto-Brightness Control for the Display Brightness Based on the Brightness in the Environment"), 20120242698 (Haddick et al., Sep. 27, 2012, "See-Through Near-Eye Display Glasses with a Multi-Segment Processor-Controlled Optical Layer"), 20130056010 (Walker et al., Mar. 7, 2013, "Autonomous Positive Airway Pressure System"), 20130127980 (Haddick et al., May 23, 2013, "Video Display Modification Based on Sensor Input for a See-Through Near-to-Eye Display"), and 20130242262 (Lewis, Sep. 19, 2013, "Enhanced Optical and Perceptual Digital Eyewear").

Relevant prior art also includes U.S. patent applications: 20130303837 (Berka et al., Nov. 14, 2013, "Systems and Methods for Optimization of Sleep and Post-Sleep Performance"), 20130314303 (Osterhout et al., Nov. 28, 2013, "AR Glasses with User Action Control of and Between Internal and External Applications with Feedback"), 20140023999 (Greder, Jan. 23, 2014, "Detection and Feedback of Information Associated with Executive Function"), 20140223462 (Aimone et al., Aug. 7, 2014, "System and Method Ffor Enhancing Content Using Brain-State Data") 20140267005 (Urbach, Sep. 18, 2014, "Eye Piece for Augmented and Virtual Reality"), 20140267401 (Urbach, Sep. 18, 2014, "Visual Cortex Thought Detector Interface"), 20140316230 (Denison et al., Oct. 23, 2014, "Methods and Devices for Brain Activity Monitoring Supporting Mental State Development and Training"), 20140347265 (Aimone et al., Nov. 27, 2014, "Wearable Computing Apparatus and Method"), and 20140375545 (Ackerman et al., Dec. 25, 2014, "Adaptive Event Recognition").

SUMMARY OF THE INVENTION

This invention can be embodied in EEG glasses (electroencephalographic eyewear) comprising an eyewear frame with a front section and two side sections, wherein at least one side section starts behind a person's ear, curves upward and forward around the ear, then spans forward and upward onto a portion of the person's forehead, and then curves downward to connect to the front section. These EEG glasses (electroencephalographic eyewear) further include a flexible protrusion which is attached to the side section and an electromagnetic energy sensor which collects data concerning electromagnetic brain activity, wherein the flexible protrusion holds the electromagnetic energy sensor. These EEG glasses (electroencephalographic eyewear) can further comprise an energy source, a data processor, and a data transmitter and/or receiver. The prior art does not appear to disclose such EEG glasses (electroencephalographic eyewear) which bring electromagnetic brain sensors into contact with a person's forehead while being relatively non-intrusive and also stable during body motion.

INTRODUCTION TO THE FIGURES

FIG. 3 shows EEG glasses with a sinusoidal flexible protrusion on a side section.

FIG. 4 shows EEG glasses with an elliptical or oval protrusion on a side section.

FIG. 15 shows EEG glasses with a wedge-shaped flexible protrusion on a side section.

FIG. 16 shows EEG glasses with an adjustable wedge-shaped flexible protrusion on a side section.

DETAILED DESCRIPTION OF THE FIGURES

Figure 1:
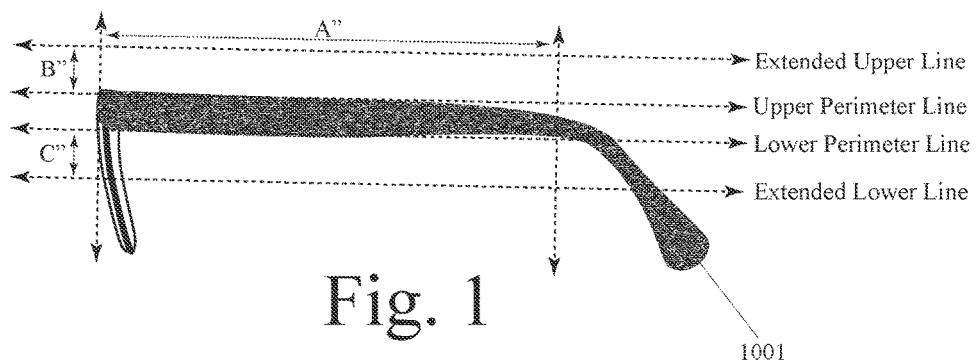
FIGS. 1 and 2 show virtual lines with respect to eyewear designs which are later used to specify designs more precisely.
Figure 2:
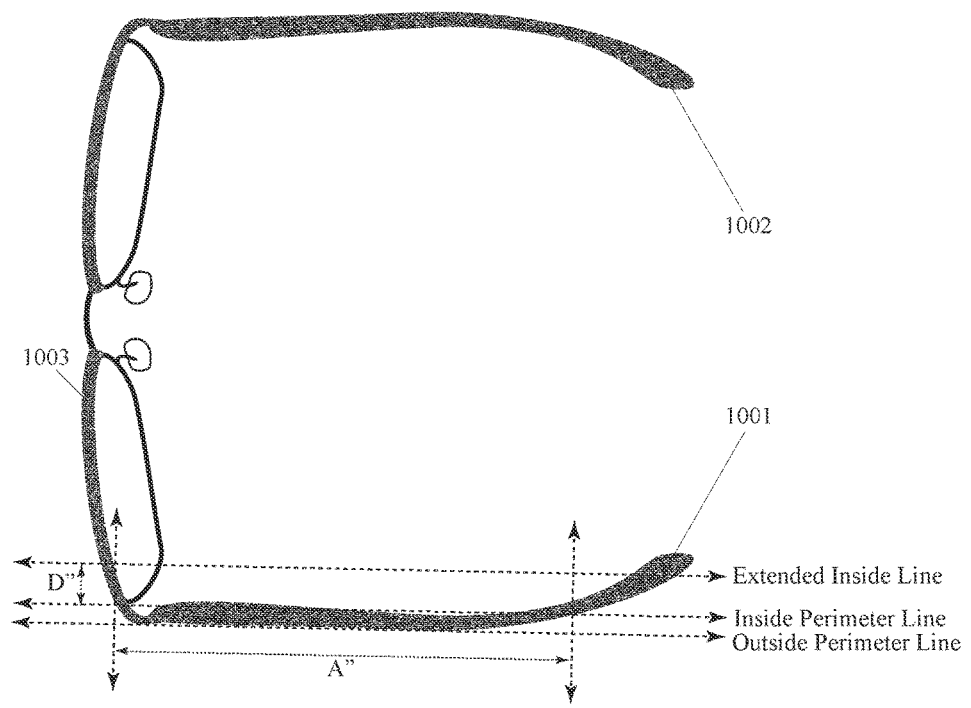

FIGS. 3 through 49 show examples of how this invention can be embodied in "EEG Glasses" (electroencephalographic eyewear). Before showing these examples, FIGS. 1 and 2 are provided to define virtual lines which can be used to specify embodiments of this invention more precisely. FIGS. 1 and 2 show side and top-down views, respectively, of a frame for eyeglasses or other eyewear, wherein this frame includes: first side section 1001; second side section 1002; and front section 1003. In an example, a first side section can be a left side section and a second side section can be a right side section, or vice versa.

FIGS. 1 and 2 show how virtual perimeter lines and extended lines can be defined for one side section of this frame for eyeglasses or other eyewear. In this example, virtual perimeter lines and extended lines are defined for side section 1001. These perimeter lines and extended lines are used subsequently in this disclosure in order to more-precisely specify the locations and dimensions of various embodiments of this invention. FIGS. 1 and 2 show how the following seven virtual straight lines can be defined for a side section of the frame for eyeglasses or other eyewear. These seven virtual straight lines are: Upper Perimeter Line; Extended Upper Line; Lower Perimeter Line; Extended Lower Line; Inside Perimeter Line; Extended Inside Line; and Outside Perimeter Line. The relative locations of these lines are specified using inch-based distance parameters A", B", C" and D". It is to be understood that metric equivalents can be substituted for inch-based measurements.

As shown in FIG. 1, the Upper Perimeter Line is the virtual straight line which most closely fits the upper perimeter of the anterior (front) A" of the side section of a frame for eyeglasses or other eyewear as viewed from a side perspective. Closeness of fit can be determined by minimizing the sum of squared deviations (distances) from the virtual straight line to the upper perimeter of the side section. As shown in FIG. 1, the Extended Upper Line is a virtual straight line which is parallel to the Upper Perimeter Line and B" (directly) above the Upper Perimeter Line. As shown in FIG. 1, the Lower Perimeter Line is the virtual straight line which is parallel to the Upper Perimeter Line and most closely fits the lower perimeter of the anterior (front) A" of the side section as viewed from a side perspective. Closeness of fit can be determined by minimizing the sum of squared deviations from the virtual straight line to the lower perimeter of the side section. As shown in FIG. 1, the Extended Lower Line is the virtual straight line which is parallel to the Lower Perimeter Line and C" (directly) below the Lower Perimeter Line. In an example, the Upper Perimeter Line, Extended Upper Line, Lower Perimeter Line, and Extended Lower Line can all be in the same vertical plane.

As shown in FIG. 2, the Inside Perimeter Line is the virtual straight line which most closely fits the inside (configured to face toward the person's head when worn) perimeter of the anterior (front) A" of the side section of a frame for eyeglasses or other eyewear as viewed from a top-down perspective. Closeness of fit can be determined by minimizing the sum of squared deviations (distances) from a virtual straight line to the inside perimeter of the side section. As shown in FIG. 2, the Extended Inside Line is the virtual straight line which is parallel to the Inside Perimeter Line and D" (directly) toward the person's head from the Inside Perimeter Line. As shown in FIG. 2, the Outside Perimeter Line is the virtual straight line which is parallel to the Upper Perimeter Line and most closely fits the outside perimeter of the anterior (front) A" of the side section as viewed from a top-down perspective. Closeness of fit can be determined by minimizing the sum of squared deviations from the virtual straight line to the outside perimeter of the side section. In an example, the Inside Perimeter Line, Extended Inside Line, and Outside Perimeter Line can all be in the same horizontal plane.

Alternatively, these virtual lines can be defined based on the front half of the side section rather than the front A" of the side section. For example: an Upper Perimeter Line can be defined as the virtual straight line which most closely fits the upper perimeter of the anterior (front) half of the side section of a frame for eyeglasses or other eyewear as viewed from a side perspective, the Lower Perimeter Line can be defined as the virtual straight line which is parallel to the Upper Perimeter Line and most closely fits the lower perimeter of the anterior (front) half of the side section as viewed from a side perspective; the Inside Perimeter Line can be defined as the virtual straight line which most closely fits the inside (configured to face toward the person's head when worn) perimeter of the anterior (front) half of the side section the side section of a frame for eyeglasses or other eyewear as viewed from a top-down perspective; and the Outside Perimeter Line can be defined as the virtual straight line which is parallel to the Upper Perimeter Line and most closely fits the outside perimeter of the anterior (front) half the side section as viewed from a top-down perspective.

In an example, a three-dimensional space can be defined as the space with an upper vertical boundary at the height of the Extended Upper Line, with a lower vertical boundary at the height of the Extended Lower Line, with an inner horizontal boundary at the horizontal location of the Extended Inside Line, and an outer horizontal boundary at the horizontal location of the Outside Perimeter Line. In an example, this three-dimensional space can be a longitudinal shape with (the same shape or varying shape) quadrilateral cross-sections. In an example, a flexible protrusion which is configured to hold an electromagnetic energy sensor on a person's head can be contained within this virtual three-dimensional space. In an example, a flexible protrusion which is attached to a side section of a frame of eyeglasses or other eyewear and which is configured to hold an electromagnetic energy sensor on a person's head can be contained within this virtual three-dimensional space related to this side section.

In an example, A" can be a number of inches selected from within the range of 2" and 6". In an example, A" can be a number of inches selected from within the range of 3" and 5". In an example, A" can equal 3". In an example, A" can equal 4". In an example, B" can be a number of inches selected from within the range of 0" and 3". In an example, B" can be a number of inches selected from within the range of 0" and 2". In an example, B" can equal 0". In an example, B" can equal ½". In an example, B" can equal 1". In an example, C" can be a number of inches selected from within the range of 0" and 2". In an example, C" can be a number of inches selected from within the range of 0" and 1". In an example, C" can equal 0". In an example, C" can equal ½". In an example, D" can be a number of inches selected from within the range of 0" and 2". In an example, D" can be a number of inches selected from within the range of 0" and 1". In an example, D" can equal ½". In an example, D" can equal 1". In an example, A"=4", B"=½", C"=½", and D"=1". In an example, A"=4", B"=0", C"=0", and D"=1". It is to be understood that metric equivalents can be substituted for inch-based measurements.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible protrusion which is part of, or attached to, a selected side section; wherein the selected side section is selected from the group consisting of the first section and the second section; wherein the flexible protrusion is contained within a three-dimensional space with an upper vertical boundary at the height of an Extended Upper Line, a lower vertical boundary at the height of an Extended Lower Line, an inner horizontal boundary at the horizontal location of an Extended Inside Line, and an outer horizontal boundary at the horizontal location of an Outside Perimeter Line; wherein an Upper Perimeter Line is a virtual straight line which most closely fits the upper perimeter of the anterior A" of the selected side section; wherein the Extended Upper Line is a virtual straight line which is parallel to the Upper Perimeter Line and B" above the Upper Perimeter Line; wherein a Lower Perimeter Line is the virtual straight line which is parallel to the Upper Perimeter Line and most closely fits the lower perimeter of the anterior A" of the selected side section; wherein the Extended Lower Line is the virtual straight line which is parallel to the Upper Perimeter Line and C" below the Lower Perimeter Line; wherein an Inside Perimeter Line is the virtual straight line which most closely fits the inside perimeter of the anterior A" of the selected side section; wherein the Extended Inside Line is the virtual straight line which is parallel to the Inside Perimeter Line and D" toward the person's head from the Inside Perimeter Line; wherein the Outside Perimeter Line is the virtual straight line which is parallel to the Upper Perimeter Line and most closely fits the outside perimeter of the anterior A" of the selected side section; and wherein A" is 6" or less, B" is ½" or less, C"

is ½" or less, and D" is 2" or less; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible protrusion which is part of, or attached to, a selected side section; wherein the selected side section is selected from the group consisting of the first section and the second section; wherein the flexible protrusion is contained within a three-dimensional space with an upper vertical boundary at the height of an Extended Upper Line, a lower vertical boundary at the height of an Extended Lower Line, an inner horizontal boundary at the horizontal location of an Extended Inside Line, and an outer horizontal boundary at the horizontal location of an Outside Perimeter Line; wherein an Upper Perimeter Line is a virtual straight line which most closely fits the upper perimeter of the selected side section; wherein the Extended Upper Line is a virtual straight line which is parallel to the Upper Perimeter Line and B" above the Upper Perimeter Line; wherein a Lower Perimeter Line is the virtual straight line which is parallel to the Upper Perimeter Line and most closely fits the lower perimeter the selected side section; wherein the Extended Lower Line is the virtual straight line which is parallel to the Upper Perimeter Line and C" below the Lower Perimeter Line; wherein an Inside Perimeter Line is the virtual straight line which most closely fits the inside perimeter of the anterior A" of the selected side section; wherein the Extended Inside Line is the virtual straight line which is parallel to the Inside Perimeter Line and D" toward the person's head from the Inside Perimeter Line; wherein the Outside Perimeter Line is the virtual straight line which is parallel to the Upper Perimeter Line and most closely fits the outside perimeter of the selected side section; and B" is ½" or less, C" is ½" or less, and D" is 2" or less; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible protrusion which is part of, or attached to, a selected side section; wherein the selected side section is selected from the group consisting of the first section and the second section; wherein the flexible protrusion is contained within a three-dimensional space with an upper vertical boundary at the height of an Upper Perimeter Line, a lower vertical boundary at the height of a Lower Perimeter Line, an inner horizontal boundary at the horizontal location of an Extended Inside Line, and an outer horizontal boundary at the horizontal location of an Outside Perimeter Line; wherein an Upper Perimeter Line is a virtual straight line which most closely fits the upper perimeter of the selected side section; wherein a Lower Perimeter Line is the virtual straight line which is parallel to the Upper Perimeter Line and most closely fits the lower perimeter the selected side section; wherein an Inside Perimeter Line is the virtual straight line which most closely fits the inside perimeter of the selected side section; wherein the Extended Inside Line is the virtual straight line which is parallel to the Inside Perimeter Line and D" toward the person's head from the Inside Perimeter Line; wherein the Outside Perimeter Line is the virtual straight line which is parallel to the Upper Perimeter Line and most closely fits the outside perimeter of the selected side section; and D" is 2" or less; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible protrusion which is part of, or attached to, a selected side section; wherein the selected side section is selected from the group consisting of the first section and the second section; and wherein this flexible protrusion is configured to be located between the person's head and the selected side section; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible protrusion which is part of, or attached to, a selected side section and which protrudes from the selected side section toward the person's head; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible protrusion which is part of, or attached to, a selected side section and is not visible from an outer side view of the frame; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible protrusion which is part of, or attached to, a selected side section, wherein the upper perimeter of the flexible protrusion is not more than ¼" higher than the upper perimeter of the selected side section, and wherein the lower perimeter of the flexible protrusion is not more than ¼" lower than the lower perimeter of the selected side section; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible and/or compressible protrusion which is part of, or attached to, a selected side section; wherein the selected side section is selected from the group consisting of the first section and the second section; wherein the flexible and/or compressible protrusion is contained within a three-dimensional space with an upper vertical boundary at the height of an Extended Upper Line, a lower vertical boundary at the height of an Extended Lower Line, an inner horizontal boundary at the horizontal location of an Extended Inside Line, and an outer horizontal boundary at the horizontal location of an Outside Perimeter Line; wherein an Upper Perimeter Line is a virtual straight line which most closely fits the upper perimeter of the anterior A" of the selected side section; wherein the Extended Upper Line is a virtual straight line which is parallel to the Upper Perimeter Line and B" above the Upper Perimeter Line; wherein a Lower Perimeter Line is the virtual straight line which is parallel to the Upper Perimeter Line and most closely fits the lower perimeter of the anterior A" of the selected side section; wherein the Extended Lower Line is the virtual straight line which is parallel to the Upper Perimeter Line and C" below the Lower Perimeter Line; wherein an Inside Perimeter Line is the virtual straight line which most closely fits the inside perimeter of the anterior A" of the selected side section; wherein the Extended Inside Line is the virtual straight line which is parallel to the Inside Perimeter Line and D" toward the person's head from the Inside Perimeter Line; wherein the Outside Perimeter Line is the virtual straight line which is parallel to the Upper Perimeter Line and most closely fits the outside perimeter of the anterior A" of the selected side section; and wherein A" is 6" or less, B" is ½" or less, C" is ½" or less, and D" is 2" or less; (c) an electromagnetic energy sensor which collects data concerning electromagnetic brain activity; wherein the flexible and/or compressible protrusion is configured to hold the electromagnetic energy sensor in proximity to and/or against the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible and/or compressible protrusion which is part of, or attached to, a selected side section; wherein the selected side section is selected from the group consisting of the first section and the second section; wherein the flexible and/or compressible protrusion is contained within a three-dimensional space with an upper vertical boundary at the height of an Extended Upper Line, a lower vertical boundary at the height of an Extended Lower Line, an inner horizontal boundary at the horizontal location of an Extended Inside Line, and an outer horizontal boundary at the horizontal location of an Outside Perimeter Line; wherein an Upper Perimeter Line is a virtual straight line which most closely fits the upper perimeter of the selected side section; wherein the Extended Upper Line is a virtual straight line which is parallel to the Upper Perimeter Line and B" above the Upper Perimeter Line; wherein a Lower Perimeter Line is the virtual straight line which is parallel to the Upper Perimeter Line and most closely fits the lower perimeter the selected side section; wherein the Extended Lower Line is the virtual straight line which is parallel to the Upper Perimeter Line and C" below the Lower Perimeter Line; wherein an Inside Perimeter Line is the virtual straight line which most closely fits the inside perimeter of the anterior A" of the selected side section; wherein the Extended Inside Line is the virtual straight line which is parallel to the Inside Perimeter Line and D" toward the person's head from the Inside Perimeter Line; wherein the Outside Perimeter Line is the virtual straight line which is parallel to the Upper Perimeter Line and most closely fits the outside perimeter of the selected side section; and B" is ½" or less, C" is ½" or less, and D" is 2" or less; (c) an electromagnetic energy sensor which collects data concerning electromagnetic brain activity; wherein the flexible and/or compressible protrusion is configured to hold the electromagnetic energy sensor in proximity to and/or against the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible and/or compressible protrusion which is part of, or attached to, a selected side section; wherein the selected side section is selected from the group consisting of the first section and the second section; wherein the flexible and/or compressible protrusion is contained within a three-dimensional space with an upper vertical boundary at the height of an Upper Perimeter Line, a lower vertical boundary at the height of a Lower Perimeter Line, an inner horizontal boundary at the horizontal location of an Extended Inside Line, and an outer horizontal boundary at the horizontal location of an Outside Perimeter Line; wherein an Upper Perimeter Line is a virtual straight line which most closely fits the upper perimeter of the selected side section; wherein a Lower Perimeter Line is the virtual straight line which is parallel to the Upper Perimeter Line and most closely fits the lower perimeter the selected side section; wherein an Inside Perimeter Line is the virtual straight line which most closely fits the inside perimeter of the selected side section; wherein the Extended Inside Line is the virtual straight line which is parallel to the Inside Perimeter Line and D" toward the person's head from the Inside Perimeter Line; wherein the Outside Perimeter Line is the virtual straight line which is parallel to the Upper Perimeter Line and most closely fits the outside perimeter of the selected side section; and D" is 2" or less; (c) an electromagnetic energy sensor which collects data concerning electromagnetic brain activity; wherein the flexible and/or compressible protrusion is configured to hold the electromagnetic energy sensor in proximity to and/or against the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible and/or compressible protrusion which is part of, or attached to, a selected side section; wherein the selected side section is selected from the group consisting of the first section and the second section; and wherein this flexible and/or compressible protrusion is configured to be located between the person's head and the selected side section; (c) an electromagnetic energy sensor which collects data concerning electromagnetic brain activity; wherein the flexible and/or compressible protrusion is configured to hold the electromagnetic energy sensor in proximity to and/or against the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible and/or compressible protrusion which is part of, or attached to, a selected side section and which protrudes from the selected side section toward the person's head; (c) an electromagnetic energy sensor which collects data concerning electromagnetic brain activity; wherein the flexible and/or compressible protrusion is configured to hold the electromagnetic energy sensor in proximity to and/or against the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible and/or compressible protrusion which is part of, or attached to, a selected side section and is not visible from an outer side view of the frame; (c) an electromagnetic energy sensor which collects data concerning electromagnetic brain activity; wherein the flexible and/or compressible protrusion is configured to hold the electromagnetic energy sensor in proximity to and/or against the person's head; (d) an energy source; (e) a data processor; and (f) a data transmitter and/or receiver.

In an example, this invention can comprise: (a) a frame for eyeglasses or other eyewear; wherein this frame further comprises a front section which is configured to span the front of a person's head, a first side section which is configured to span from a first ear to the front section, and a second side section which is configured to span from a second ear to the front section; (b) a flexible and/or compressible protrusion which is part of, or attached to, a selected side section, wherein the upper perimeter of the flexible and/or compressible protrusion is not more than ¼" higher than the upper perimeter of the selected side section, and wherein the lower perimeter of the flexible and/or compressible protrusion is not more than ¼" lower than the lower perimeter of the selected side section; (c) an electromagnetic energy sensor which collects data concerning electromagnetic brain activity; wherein the flexible and/or compressible protrusion is configured to hold the electromagnetic energy sensor in proximity to and/or against the person's head; (d) an energy source; (e) a data processor; and (f) a data transmitter and/or receiver.

In an example, a frame for eyeglasses or other eyewear can be part of a device selected from the group consisting of: Augmented Reality (AR) glasses or other AR eyewear, electronically-functional eyeglasses, electronically-functional eyewear, electronically-functional goggles, electronically-functional visor, eyeglasses with integrated camera, eyewear-based human-to-computer interface, goggles, mobile EEG monitoring eyewear, non-prescription eyeglasses, prescription eyeglasses, smart eyewear, smart glasses, smart sunglasses, and Virtual Reality (VR) glasses or other VR eyewear. In an example, this invention can comprise eyewear which is selected from the group consisting of: Augmented Reality (AR) glasses or other AR eyewear, electronically-functional eyeglasses, electronically-functional eyewear, electronically-functional goggles, electronically-functional visor, eyeglasses with integrated camera, eyewear-based human-to-computer interface, goggles, mobile EEG monitoring eyewear, non-prescription eyeglasses, prescription eyeglasses, smart eyewear, smart glasses, smart sunglasses, and Virtual Reality (VR) glasses or other VR eyewear.

In an example, a front section of a frame (for glasses or other eyewear) can span the front of a person's head in the space in front of a person's eyes and/or eyebrows. In an example, a frame can hold one or more optical elements. In an example, a frame can hold one or more optical lenses. In an example, a frame can hold one or more computer displays. In an example, a frame can hold one or more optical lenses and one or more computer displays. In an example, an optical element can function as both a lens and a computer display.

In an example, the front section, first side section, and second side section (of a frame for eyeglasses or other eyewear) can each be substantially straight. In an example, the front section, first side section, and second side section of a frame can each be curved and arcuate. In an example, a frame for eyeglasses or other eyewear can be configured like conventional eyeglasses except for an upward wave or bulge in one or both side sections. In an example, a frame for eyeglasses or other eyewear can be configured like conventional eyeglasses except for an upward sinusoidal wave or bulge in one or both side sections.

In an example, a side section of a frame for glasses or other eyewear can be curved, arcuate, undulating, wavy, and/or sinusoidal. In an example, a side section can have a single upward (sinusoidal) wave within its anterior (front) half and an electromagnetic energy sensor located on (the upper portion of) this (sinusoidal) wave. In an example, a side section can have a multiple (sinusoidal) waves along its longitudinal (front to rear) axis. In an example, a side section can bifurcate into upper and lower side portions and have an electromagnetic energy sensor located on the upper portion. In an example, a side section can include a circular, oval, or elliptical portion within its anterior (front) half and an electromagnetic energy sensor located on the upper part of this portion.

In an example, a side section of a frame for glasses or other eyewear can be configured to: start with a posterior end behind a person's ear; then curve upward and forward around portion of the ear which connects to the main body of the head; then extend forward 1"-2" in a relatively straight manner; then curve upward (in a sinusoidal manner) to span a portion of the person's temple and/or forehead; and then curve back downward (in a sinusoidal manner) to connect to the front section. In an example, a side section of a frame for glasses or other eyewear can be configured to: start with a posterior end behind a person's ear; then curve upward and forward around portion of the ear which connects to the main body of the head; then curve downward (in a sinusoidal manner) in front of the person's ear; then curve upward (in a sinusoidal manner) to span a portion of the person's temple and/or forehead; and then curve back downward (in a sinusoidal manner) to connect to the front section.

In an example a side section of a frame (for glasses or other eyewear) can have an average vertical width in the range of 1/16" to 2". In an example, a side section of a frame can have a vertical width which varies within the range of 1/16" to 2". In an example a side section of a frame (for glasses or other eyewear) can have an average vertical width in the range of 1/4" to 1". In an example, a side section of a frame can have a vertical width which varies within the range of 1/4" to 1". It is to be understood that metric equivalents can be substituted for inch measurements throughout this disclosure.

In example, a side section of a frame can have a central posterior-to-anterior (back-to-front) longitudinal axis. In an example, a posterior (e.g. rear one-third) portion of this posterior-to-anterior longitudinal axis can curve around the rear of a person's ear and an anterior (e.g. front, two-thirds) portion of this longitudinal axis can span from the ear to the front section of the frame in a relatively straight manner. In an example, a posterior (e.g. rear one-third) portion of this posterior-to-anterior longitudinal axis can curve around the rear of a person's ear and an anterior (e.g. front, two-thirds) portion of this longitudinal axis can span from the ear to the front section of the frame in an arcuate (e.g. sinusoidal) manner which spans a portion of a person's temple and/or forehead. In an example, a posterior (one-third) portion of this posterior-to-anterior longitudinal axis can curve around the rear of a person's ear, a middle (one-third) portion of this longitudinal axis can span from the ear toward the front in a relatively straight manner, and an anterior (one-third) portion of this longitudinal axis can span a portion of a person's temple and/or forehead in an arcuate (sinusoidal or conic section) manner.

In an example, the front section, first side section, and second side section of a frame can be portions of a single continuous piece of material. In an example, the front section, first side section, and second side section of a frame can be separate pieces of material which are connected to each other by hinges, joints, or welds. In an example, a frame for eyeglasses or other eyewear can be made of metal, plastic, fabric, or a combination thereof. In an example, the front section, first side section, and second side section of a frame can each be rigid or semi-rigid. In an example, the front section, first side section, and second side section of a frame can each be flexible and/or elastic. In an example, one or more sections selected from the group consisting of the front section, first side section, and second side section of a frame can be rigid and one or more sections selected from this group can be flexible and/or elastic.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; and (c) then span forward in a relatively-straight axial manner to an anterior (front) end which connects to (or becomes part of) a front section of the frame. In an example, the portion of the side section described in (c) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; and (c) then span forward 3"-5" in a relatively-straight axial manner to an anterior (front) end which connects to (or becomes part of) a front section of the frame. In an example, the portion of the side section described in (c) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then span forward in a relatively-straight axial manner; (d) then curve upward and forward to a location over the person's temple and/or forehead; and (e) then curve downward and forward to an anterior (front) end which connects to (or becomes part of) a front section of the frame. In an example, a portion of the side section described in (d) or (e) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then span forward 1"-3" in a relatively-straight axial manner; (d) then curve upward and forward 1"-3" to a location over the person's temple and/or forehead; and (e) then curve downward and forward to an anterior (front) end which connects to (or becomes part of) a front section of the frame. In an example, a portion of the side section described in (d) or (e) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then curve downward and forward; (d) then curve upward and forward to a location over the person's temple and/or forehead; and (e) then curve downward and forward to an anterior (front) end which connects to (or becomes part of) a front section of the frame. In an example, a portion of the side section described in (d) or (e) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then curve downward and forward 1"-3"; (d) then curve upward and forward 1"-3" to a location over the person's temple and/or forehead; and (e) then curve downward and forward to an anterior (front) end which connects to (or becomes part of) a front section of the frame. In an example, a portion of the side section described in (d) or (e) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then curve downward and forward; (d) then curve upward, forward, and inward to a location over the person's temple and/or forehead; and (e) then curve downward, forward, and outward to an anterior (front) end which connects to (or becomes part of) a front section of the frame. In an example, a portion of the side section described in (d) or (e) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then curve downward and forward 1"-3"; (d) then curve upward, forward, and inward 1"-3" to a location over the person's temple and/or forehead; and (e) then curve downward, forward, and outward to an anterior (front) end which connects to (or becomes part of) a front section of the frame. In an example, a portion of the side section described in (d) or (e) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then curve downward and forward; (d) then curve upward and forward to bifurcate, wherein an upper portion of this bifurcation extends forward over the person's temple and/or forehead, and wherein the lower portion of this bifurcation curves forward to connect to a front section of the frame. In an example, the upper portion of a bifurcation described in (d) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then bifurcate, wherein an upper portion of this bifurcation extends to the person's temple and/or forehead, and wherein a lower portion of this bifurcation spans forward in a relatively-straight axial manner to an anterior (front) end which connects to (or becomes part of) a front section of the frame. In an example, the upper and lower portion can connect to each other at both posterior and anterior locations. In an example, the upper portion of a bifurcation described in (c) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then bifurcate, wherein an upper portion of this bifurcation extends 0.5" to 4" to the person's temple and/or forehead, and wherein a lower portion of this bifurcation spans forward in a relatively-straight axial manner to an anterior (front) end which connects to (or becomes part of) a front section of the frame. In an example, the upper and lower portion can connect to each other at both posterior and anterior locations. In an example, the upper portion of a bifurcation described in (c) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then bifurcate, wherein an upper portion of this bifurcation curves around the person's temple and/or forehead, and wherein a lower portion of this bifurcation spans forward in a relatively-straight axial manner to an anterior (front) end which connects to (or becomes part of) a front section of the frame. In an example, upper and lower portions can be connected to each other at two or more locations, with a gap between the portions between these connections. In an example, the upper portion of a bifurcation described in (c) can hold an electromagnetic energy sensor on a person's head.

In an example, a side section of a frame for eyeglasses or other eyewear can be configured to span forward from the rear portion of a person's ear in the following manner: (a) start with a posterior (rear) end which is configured to be worn posterior to (behind) a person's ear; (b) then curve upward and forward around the tissue connection between the person's outer ear to the rest of the person's head, to the top of this tissue connection; (c) then expand, fan out, broaden, and/or widen into a fin or wedge shaped structure which curves around a side portion of the person's forehead; and then connects to a front section of the frame. In an example, the portion of the side section described in (c) can hold an electromagnetic energy sensor on a person's head.

In an example, a sensor-holding protrusion which is part of, or attached to, a side section of a frame can be flexible. In an example, a protrusion can be a flexible piece of metal, plastic, or fabric. In an example, a protrusion can be compressible. In an example, a protrusion can be a compressible foam component. In an example, a protrusion can be inflatable. In an example, a protrusion can be a balloon or other type of inflatable compartment. In an example, a protrusion can be pleated and/or folded (like a bellows) for expansion or contraction. In an example, a protrusion can be elastic. In an example, a protrusion can be an elastic band or strip. In an example, a protrusion can be tensile. In an example, a protrusion can be a spring, coil, or other tensile member. In an example, a protrusion can be a piston or other telescoping structure.

In an example, a protrusion which holds an electromagnetic energy sensor can have a shape selected from the group consisting of: arcuate, bell curve shaped, bellows, circular, conic, conic-section shaped, cylindrical, egg-shaped, elliptical, frustal, half sinusoidal, half-bell curve shaped, helical, kidney-bean shaped, oval, parabolic, piston, pyramidic, quarter sinusoidal, rounded rectangular, rounded square, sinusoidal, spherical, S-shapes, telescoping, triangular, and wedge shaped. In an example, a protrusion can be transparent or translucent so as to be less obvious.

In an example, a protrusion can be contained within a vertical space that is upward bounded by the height of an Upper Perimeter Line and downward bounded by the height of a Lower Perimeter Line. In this case, the protrusion should not be visible from an outer side view perspective of the eyewear side frame. In an example, a protrusion can be contained within a vertical space that is upward bounded by the height of an Extended Upper Line and downward bounded by the height of an Extended Perimeter Line. In an example, the Extended Upper Line can be up to 1" (or the metric equivalent) above the Upper Perimeter Line and the Extended Lower Line can be up to 1" (or the metric equivalent) below the Lower Perimeter Line.

In an example, only one side section of a frame for eyeglasses or other eyewear can have a protrusion which holds an electromagnetic energy sensor. In an example, eyewear can have a unilateral electromagnetic energy sensor. In an example, each of the two side sections of a frame for eyeglasses or other eyewear can have a protrusion which holds an electromagnetic energy sensor. In an example, eyewear can have bilateral electromagnetic energy sensors. In an example, one or both side sections can have multiple protrusions and/or multiple electromagnetic energy sensors. In an example, multiple protrusions and/or multiple electromagnetic energy sensors on a side section of an eyewear frame can span a range between 1" and 4".

In an example, a protrusion can apply force to the outer side of an electromagnetic energy sensor (which faces away from a person's body) so that the side of the inner side of an electromagnetic energy sensor (which faces toward the person's body) exerts force on the person's body. This can achieve better electromagnetic communication with the person's body. In an example, a protrusion can gently press an electromagnetic energy sensor against a person's head. In an example, a protrusion can include a spring mechanism which gently presses an electromagnetic energy sensor against a person's head. In an example, a protrusion can include an elastic mechanism which gently presses an electromagnetic energy sensor against a person's head. In an example, a protrusion can include an inflatable mechanism (filled with a gas or liquid) which gently presses an electromagnet energy sensor against a person's head.

In an example, the location of a protrusion (and thus an electromagnetic energy sensor which it holds) can be manually or automatically moved with respect to the side section of an eyewear frame. In an example, the location of a protrusion (and associated electromagnetic energy sensor) can be moved forward or backward, such as along a track or channel on the side section of an eyewear frame. In an example, the location of a protrusion (and associated electromagnetic energy sensor) can be moved up or down, such as along a track or channel on the side section of an eyewear frame. In an example, the angle of a protrusion with respect to the side section of an eyewear frame can be manually or automatically adjusted. In an example, a protrusion can be attached to different locations along the side section of an eyewear frame.

In an example, the location of contact between an electromagnetic energy sensor and a person's head can be adjusted by adjusting the location of a protrusion by one or more actions selected from the following group: sliding the protrusion along a track or channel on a side section of an eyewear frame; clipping the protrusion to different locations along the side section of an eyewear frame, rotating a threaded protrusion; adjusting the inflation pressure of an inflated protrusion; pneumatic adjustment of a liquid-filled protrusion; adjustment of a piston or other telescoping structure, adjusting the spring and/or coil tension of a protrusion comprising a spring and/or coil; and adjusting the magnetic attraction or repulsion of a magnetic protrusion.

In an example, the force and/or pressure of contact between an electromagnetic energy sensor and a person's head can be adjusted by adjusting the location of a protrusion by one of more actions selected from the following group: sliding the protrusion along a track or channel on a side section of an eyewear frame; clipping the protrusion to different locations along the side section of an eyewear frame, rotating a threaded protrusion; adjusting the inflation pressure of an inflated protrusion; pneumatic adjustment of a liquid-filled protrusion; adjusting the spring and/or coil tension of a protrusion comprising a spring and/or coil; and adjusting the magnetic attraction or repulsion of a magnetic protrusion.

In an example, this invention can further comprise one or more force and/or pressure sensors which measure the force and/or pressure applied by an electromagnetic energy sensor against a person's head (e.g. temple and/or forehead). In an example, this invention can adjust the configuration and/or location of a flexible protrusion so as to adjust the force and/or pressure applied by an electromagnetic energy sensor against a person's head (e.g. temple and/or forehead).

If data from a force and/or pressure sensor indicates inadequate force and/or pressure applied by an electromagnetic energy sensor, then this can trigger adjustment of the configuration and/or location of a flexible protrusion which holds the electromagnetic energy sensor so as to increase the force and/or pressure applied by an electromagnetic energy sensor. If data from a force and/or pressure sensor indicates excessive force and/or pressure applied by an electromagnetic energy sensor, then this can trigger adjustment of the configuration and/or location of a flexible protrusion which holds the electromagnetic energy sensor so as to decrease the force and/or pressure applied by an electromagnetic energy sensor.

In an example, if a force and/or pressure sensor indicates inadequate force and/or pressure applied by an electromagnetic energy sensor to a person's forehead, then this can trigger increased inflation of a flexible protrusion which holds the electromagnetic energy sensor. In an example, if a force and/or pressure sensor indicates excessive force and/or pressure applied by an electromagnetic energy sensor to a person's forehead, then this can trigger decreased inflation of a flexible protrusion which holds the electromagnetic energy sensor. In an example, if a force and/or pressure sensor indicates inadequate force and/or pressure applied by an electromagnetic energy sensor to a person's forehead, then this can trigger (pneumatic) extension of a telescoping protrusion which holds the electromagnetic energy sensor.

In an example, if a force and/or pressure sensor indicates excessive force and/or pressure applied by an electromagnetic energy sensor to a person's forehead, then this can trigger (pneumatic) retraction of a telescoping protrusion which holds the electromagnetic energy sensor.

In an example, if a force and/or pressure sensor indicates inadequate force and/or pressure applied by an electromagnetic energy sensor to a person's forehead, then this can trigger threaded rotation and extension of a protrusion which holds the electromagnetic energy sensor. In an example, if a force and/or pressure sensor indicates excessive force and/or pressure applied by an electromagnetic energy sensor to a person's forehead, then this can trigger threaded rotation and retraction of a protrusion which holds the electromagnetic energy sensor. In an example, if a force and/or pressure sensor indicates inadequate force and/or pressure applied by an electromagnetic energy sensor to a person's forehead, then this can trigger electromagnetic actuator extension of a protrusion which holds the electromagnetic energy sensor. In an example, if a force and/or pressure sensor indicates excessive force and/or pressure applied by an electromagnetic energy sensor to a person's forehead, then this can trigger electromagnetic actuator retraction of a protrusion which holds the electromagnetic energy sensor.

In an example, an electromagnetic energy sensor of this invention can measure the conductivity, voltage, resistance, impedance, and/or permittivity of electromagnetic energy transmitted through and/or emitted from a portion of a person's brain and/or head. In an example, an electromagnetic energy sensor can be an electroencephalographic (EEG) sensor. In an example, an electromagnetic energy sensor can be a dry electrode. In an example, an electromagnetic energy sensor can collect data on electromagnetic energy patterns and/or electromagnetic fields which are naturally generated by electromagnetic brain activity. In an example, an electromagnetic energy sensor can be used in combination with an electromagnetic energy emitter. In an example, an electromagnetic energy emitter can be in contact with the surface of a person's head. In an example, an electromagnetic energy sensor can measure the conductivity, voltage, resistance, impedance, and/or permittivity of electromagnetic energy emitted from an electromagnetic energy emitter and transmitted through a portion of a person's head.

In an example, the location of an electromagnetic energy sensor can be selected from the group of standard electrode locations consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, data from one or more electromagnetic energy sensors can be filtered to remove artifacts before the application of a primary statistical method. In an example, a filter can be used to remove electromagnetic signals from eye blinks, eye flutters, or other eye movements before the application of a primary statistical method. In an example, a notch filter can be used as well to remove 60 Hz artifacts caused by AC electrical current. In various examples, one or more filters can be selected from the group consisting of: a high-pass filter, a band-pass filter, a loss-pass filter, an electromyographic activity filter, a 0.5-1 Hz filter, and a 35-70 Hz filter.

In an example, data from an electromagnetic energy sensor can be analyzed using Fourier transformation methods in order to identify repeating energy patterns in clinical frequency bands. In an example, these clinical frequency bands can be selected from the group consisting of: Delta, Theta, Alpha, Beta, and Gamma. In an example, the relative and combinatorial power levels of energy in two or more different clinical frequency bands can be analyzed. In an example, a person can receive real-time feedback based on analysis of data concerning their electromagnetic brain activity. In an example, a person can control a computer or other device by self-modifying their electromagnetic brain activity.

In an example, an energy source for this device can be a battery internal to the device. In an example, an energy source can be internal to the device during regular operation (such as an internal battery, capacitor, energy-storing microchip, or wound coil or spring). In an example, an energy source can harvest and/or transduce energy from a person's body (such as kinetic or mechanical energy from body motion, electromagnetic energy from the person's body, blood flow or other internal fluid flow, glucose metabolism, or thermal energy from the person's body). In an example, an energy source can harvest and/or transduce energy from a source external to the device (such as electromagnetic inductance from external source, solar energy, indoor lighting energy, wired connection to an external power source, ambient or localized radiofrequency energy, or ambient thermal energy). In an example, an energy source can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy.

In an example, a data processor can be a computer. In an example, a data processor can be a central processing unit (CPU). In an example, a data processor can be a computer chip or board. In an example, a data processor can be in electromagnetic communication with an energy source, one or more electromagnetic energy sensors, and a data transmitter/receiver via wires or other electrically-conductive pathways. In an example, a data processor can process data from one or more electromagnetic energy sensors to analyze data patterns. In an example, a data processor can receive data from one or more electromagnetic energy sensors and relay this data to a data transmitter/receiver which, in turn, sends this data to a separate (remote) data processor which analyzes data patterns.

In an example, a data processor can be in wireless communication with a separate wearable device selected from the group consisting of: a wristwatch, smart watch, fitness watch, watch phone, bracelet phone, smart bracelet, fitness bracelet, smart wrist band, electronically-functional wrist band, other wrist-worn electronic device, or smart armband; a smart button, electronically-functional button, pin, brooch, pendant, beads, neck chain, necklace, dog tags, locket, or medallion; a smart finger ring, electronically-functional finger ring, electronically-functional earring, nose ring, or ear bud or clip; a wearable camera; an article of smart clothing, an electronically-functional shirt, electronically-functional pants, or a smart belt.

In an example, a data processor can be in wireless communication with a separate mobile device selected from the group consisting of: smart phone, mobile phone, holophone, or cellular phone; PDA; electronic tablet; electronic pad; and other electronically-functional handheld device. In an example, a data processor can be in wireless communication with a relatively fixed-location device selected from the group consisting of: laptop computer, desktop computer, internet terminal, smart appliance, home control system, and other fixed-location electronic communication device.

In an example, this device can further comprise a human-to-computer interface selected from the group consisting of: a button, knob, or dial; a display screen; a gesture-recognition interface; a holographic user interface; a microphone; a physical keypad or keyboard; a pressure-sensitive textile array; a spectroscopic sensor; a speech or voice recognition interface; a touch screen; a virtual keypad or keyboard; an electronically-functional textile interface; and an eye gaze tracker.

In an example, this device can further comprise a computer-to-human interface selected from the group consisting of: a coherent-light image projector; a display screen; a holographic user interface; a laser; a myostimulating member; a neurostimulating member; a non-coherent-light image projector; a speaker or other sound-emitting member; a speech or voice recognition interface; a synthesized voice; a vibrating or other tactile sensation creating member; an electromagnetic energy emitter; an electronically-functional textile interface; an infrared light emitter; an infrared light projector; and an LED or LED array.

In an example, this device an further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, this invention can further comprise one or more other types of electromagnetic energy sensors selected from the group consisting of: peripheral neurosensor, electromyography (EMG) sensor, Hall-effect sensor, electrocardiogram (ECG) sensor, cardiac monitor, EOG sensor, galvanic skin response (GSR) sensor, compass, magnometer, magnetic sensor, potentiometer, variable-resistance sensor, resistive bend sensor, piezoelectric sensor, piezomechanical sensor, and piezoresistive sensor.

In an example, this device can further comprise one or more optical sensors selected from the group consisting of: camera, other imaging member, photoelectric sensor, light intensity sensor, infrared light sensor, ultraviolet light sensor, spectroscopy sensor, near-infrared spectroscopy sensor, Raman spectroscopy sensor, spectral analysis sensor, spectrometry sensor, spectrophotometer sensor, chromatography sensor, other light-spectrum-analyzing sensor, fluorescence sensor, blood oximetry sensor, optoelectronic sensor, optical code scanner, laser sensor, optical strain detector, and variable-translucence sensor.

In an example, this device can further comprise one or more sonic energy sensors selected from the group consisting of: microphone, ultrasonic sensor, acoustic sensor, heart rate sensor, respiration or pulmonary function monitor, respiratory rate sensor, and CPAP monitor. In an example, this device can further comprise one or more biochemical sensors selected from the group consisting of: electrochemical sensor, biochemical sensor, glucose sensor, chemoreceptor sensor, gas sensor, microbial sensor, micro-sampling tissue or body fluid sensor, pH level sensor, and photochemical sensor.

In an example, this device can further comprise one or more force-related sensors selected from the group consisting of: blood pressure sensor, heart rate monitor, capacitive sensor, force sensor, particulate force transducer, electromagnetic pressure sensor, other pressure sensor, torque sensor, and torsion sensor. In an example, this device can further comprise one or more actuators selected from the group consisting of: brushless DC motor, brush-type DC motor, electric motor, electromagnetic actuator, hydraulic actuator, induction motor, MEMS actuator, piezoelectric actuator, pneumatic actuator, and stepper motor.

In an example, this device can further comprise one or more additional sensors selected from the group consisting of: humidity sensor, moisture sensor, thermometer, temperature sensor, flow sensor, differential transducer sensor, elastomeric sensor, vibration sensor, helical sensor, revolute joint sensor, ionizing radiation sensor, neurosensor, food consumption sensor, eye-tracking sensor, Micro-Electro-Mechanical System (MEMS) sensor, nanoscale sensor, nanotube sensor, and nanoparticle sensor.

In various examples, this device can comprise one or more additional wearable sensors can be selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, kinematic sensor; peripheral neurosensor, electromyography (EMG) sensor, Hall-effect sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, or piezoresistive sensor; camera, other imaging member, photoelectric sensor, light intensity sensor, infrared light sensor, ultraviolet light sensor, spectroscopy sensor, near-infrared spectroscopy sensor, Raman spectroscopy sensor, spectral analysis sensor, spectrometry sensor, spectrophotometer sensor, chromatography sensor, other light-spectrum-analyzing sensor, fluorescence sensor, blood oximetry sensor, optoelectronic sensor, optical code scanner, laser sensor, optical strain detector, variable-translucence sensor; microphone, ultrasonic sensor, acoustic sensor, heart rate sensor, respiration or pulmonary function monitor, respiratory rate sensor, CPAP monitor; blood pressure sensor, heart rate monitor, capacitive sensor, force sensor, particulate force transducer, electromagnetic pressure sensor, other pressure sensor, torque sensor, torsion sensor; electrochemical sensor, biochemical sensor, glucose sensor, chemoreceptor sensor, gas sensor, microbial sensor, micro-sampling tissue or body fluid sensor, pH level sensor, photochemical sensor; Micro-Electro-Mechanical System (MEMS) sensor, nanoscale sensor, nanotube sensor, nanoparticle sensor; humidity sensor, moisture sensor; thermometer, temperature sensor; flow sensor; differential transducer sensor, elastomeric sensor, vibration sensor, smooch detector, helical sensor, revolute joint sensor, ionizing radiation sensor, neurosensor; food consumption sensor, and eye tracking sensor.

In an example, this device can further comprise one or more additional components selected from the group consisting of: accelerometer, computer-to-human interface, data memory, data memory component, display screen, electronic payment mechanism, gesture recognition capability, GPS component, gyroscope, heart rate monitor, human-to-computer interface, light, microphone, speaker, speech-recognition software, tactile actuator, touch screen, touch-activated button, vibrator, wireless data reception component, and wireless data transmitter.

FIGS. 3 through 49 show different examples of "EEG glasses" (electroencephalographic eyewear). Relevant design and component variations discussed thus far in this disclosure or in other priority-linked disclosures can be applied to these, but are not repeated in the narratives accompanying each figure in order to reduce redundant content.

FIG. 3 shows a top-down view of an example of how this invention can be embodied in electroencephalographic eyewear comprising: (a) an eyewear frame which further comprises a front section which is configured to span the front of a person's head, a first side section which is configured to span from a first ear to the front section, and a second side section which is configured to span from a second ear to the front section; (b) a flexible protrusion which is part of, or attached to, a selected side section; wherein the selected side section is selected from the group consisting of the first section and the second section; wherein the flexible protrusion is contained within a three-dimensional space with an upper vertical boundary at the height of an Extended Upper Line, a lower vertical boundary at the height of an Extended Lower Line, an inner horizontal boundary at the horizontal location of an Extended Inside Line, and an outer horizontal boundary at the horizontal location of an Outside Perimeter Line; wherein an Upper Perimeter Line is a virtual straight line which most closely fits the upper perimeter of the anterior A" of the selected side section; wherein the Extended Upper Line is a virtual straight line which is parallel to the Upper Perimeter Line and B" above the Upper Perimeter Line; wherein a Lower Perimeter Line is the virtual straight line which is parallel to the Upper Perimeter Line and most closely fits the lower perimeter of the anterior A" of the selected side section; wherein the Extended Lower Line is the virtual straight line which is parallel to the Upper Perimeter Line and C" below the Lower Perimeter Line; wherein an Inside Perimeter Line is the virtual straight line which most closely fits the inside perimeter of the anterior A" of the selected side section; wherein the Extended Inside Line is the virtual straight line which is parallel to the Inside Perimeter Line and D" toward the person's head from the Inside Perimeter Line; wherein the Outside Perimeter Line is the virtual straight line which is parallel to the Upper Perimeter Line and most closely fits the outside perimeter of the anterior A" of the selected side section; and wherein A" is 6" or less, B" is ½" or less, C" is ½" or less, and D" is 2" or less; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

FIG. 3 also shows a top-down view of electroencephalographic eyewear comprising: (a) an eyewear frame which further comprises a front section which is configured to span the front of a person's head, a first side section which is configured to span from a first ear to the front section, and a second side section which is configured to span from a second ear to the front section; (b) a flexible protrusion which is part of, or attached to, a selected side section; wherein the selected side section is selected from the group consisting of the first section and the second section; wherein the upper perimeter of the flexible protrusion is no more than ¼" higher than the upper perimeter of the selected side section; and wherein the lower perimeter of the flexible protrusion is no more than ¼" lower than the lower perimeter of the selected side section; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

FIG. 3 also shows a top-down view of electroencephalographic eyewear comprising: (a) an eyewear frame which further comprises a front section which is configured to span the front of a person's head, a first side section which is configured to span from a first ear to the front section, and a second side section which is configured to span from a second ear to the front section; (b) a flexible protrusion which is part of, or attached to, a selected side section; wherein the selected side section is selected from the group consisting of the first section and the second section; and wherein flexible protrusion is not visible from an outer side (lateral) view of the selected side section; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

With respect to specific components, FIG. 3 shows a top-down view of electroencephalographic eyewear comprising: (a) an eyewear frame which further comprises front section 3003 which is configured to span the front of a person's head, first side section 3001 which is configured to span from a first ear to front section 3003, and second side section 3002 which is configured to span from a second ear to front section 3003; (b) flexible protrusion 3005 which is part of, or attached to, selected side section 3001; (c) electromagnetic energy sensor 3004 which collects data concerning electromagnetic brain activity; wherein flexible protrusion 3005 is configured to hold electromagnetic energy sensor 3004 on the person's head; (d) energy source 3006; (e) data processor 3007; and (f) data transmitter and/or receiver 3008.

In this example, a flexible protrusion which extends inward from a side section of a frame to a person's head (holding the electromagnetic energy sensor on the person head) has a horizontal cross-section with a sinusoidal shape. In other examples, a protrusion which holds an electromagnetic energy sensor can have a shape selected from the group consisting of: bell curve, bellows, circular, conic, conic-section, cylindrical, egg-shaped, elliptical, frustal, half sinusoidal, half-bell curve, helical, kidney-bean, oval, parabolic, piston, pyramidic, quarter sinusoidal, rounded rectangular, rounded square, sinusoidal, spherical, S-shape, telescoping, triangular, and wedge shaped. In an example, a protrusion can be transparent or translucent so as to be less obvious.

In this example, a flexible protrusion is made from a compressible material such as compressible foam. In an example, a flexible protrusion can be made from a low durometer material. In an example, a flexible protrusion can be made from memory foam. In an example, a flexible member can be an inflatable member such as a balloon which is filled with a gas or liquid. In an example, the size and/or expansion of a flexible protrusion can be manually or automatically adjusted. In an example, the degree of pressure exerted by an electromagnetic energy sensor against a person's head can be manually or automatically adjusted by adjusting the size and/or expansion of a flexible protrusion which holds the sensor.

In an example, a flexible protrusion can have a first configuration in which the flexible protrusion extends a first distance from the inside perimeter of the side section of a frame for glasses or other eyewear, a second configuration in which the flexible protrusion extends a second distance from the inside perimeter of the side section of the frame, the second distance is greater than the first distance, and the protrusion can be reversibly moved from the first configuration to the second configuration. In an example, the flexible protrusion can be less visible in the first configuration and the electromagnetic energy sensor which it holds can be in closer electromagnetic communication with the person's body in the second configuration. In an example, a flexible protrusion can be reversibly changed from the first configuration to the second configuration by an action selected from the group consisting of: inflation; pneumatic pressure; magnetic attraction or repulsion; threaded rotation; spring motion; tensile movement; sliding one end of a flexible protrusion; movement of an elastic band; movement of telescoping member; and movement of a piston.

In an example, the location of a flexible protrusion on a side section of a frame can be adjusted forward and backward and/or up and down. In an example, the location of contact between an electromagnetic energy sensor and a person's head can be manually or automatically adjusted by adjusting the location of a flexible protrusion. In an example, a side section of a frame can have one or more tracks or channels along which a flexible protrusion can slide in order to adjust the location of the flexible protrusion. In an example, a side section of a frame can have one or more tracks or channels along which an end of a flexible protrusion can slide in order to adjust the location and/or extension of the flexible protrusion.

In this example, there is one flexible protrusion which holds one electromagnetic energy sensor. In another example, there can be multiple flexible protrusions, each of which holds one electromagnetic energy sensor. In another example, there can be one flexible protrusion which holds multiple electromagnetic energy sensors. In another example, there can be multiple flexible protrusions which hold multiple electromagnetic energy sensors.

In this example, the vertical boundaries of the perimeter of the flexible protrusion are entirely within the vertical boundaries of the perimeter of the side section. In another example, the vertical boundaries of the perimeter of the flexible protrusion can be slightly higher or lower than the vertical boundaries of the perimeter of the side section. In another example, the vertical boundaries of the perimeter of the flexible protrusion can be no more than ¼" higher or lower than the vertical boundaries of the perimeter of the side section.

FIGS. 3 through 49 show various examples of how this invention can be embodied in EEG glasses or other electroencephalographic (EEG) eyewear. FIGS. 3 through 16 show examples of how this invention can be embodied in electroencephalographic eyewear comprising: (a) a frame for eyeglasses or other eyewear; wherein this frame further comprises a front section which is configured to span the front of a person's head, a first side section which is configured to span from a first ear to the front section, and a second side section which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, and then spans forward (3"-5") along a relatively-straight longitudinal axis to connect to the front section; (b) a flexible protrusion which is part of, or attached to, a selected side section; (c) an electromagnetic energy sensor which collects data concerning electromagnetic brain activity; wherein the flexible protrusion is configured to hold the electromagnetic energy sensor on the person's head; (d) an energy source; (e) a data processor; and (f) a data transmitter and/or receiver.

FIG. 3 shows a top-down view of an example of how this invention can be embodied in EEG glasses or other electroencephalographic eyewear comprising: (a) an eyewear frame which further comprises front section 3003 which is configured to span the front of a person's head, first side section 3001 which is configured to span from a first ear to front section 3003, and second side section 3002 which is configured to span from a second ear to front section 3003; (b) sinusoidal or conic-section flexible protrusion 3005 which is part of, or attached to, selected side section 3001; (c) electromagnetic energy sensor 3004 which collects data concerning electromagnetic brain activity; wherein flexible protrusion 3005 is configured to hold electromagnetic energy sensor 3004 on the person's head; (d) energy source 3006; (e) data processor 3007; and (f) data transmitter and/or receiver 3008.

In an example, a protrusion can be part of, or attached to, a selected side section, wherein the upper perimeter of the protrusion is not more than ¼" higher than the upper perimeter of the selected side section, and wherein the lower perimeter of the protrusion is not more than ¼" lower than the lower perimeter of the selected side section. In an example, flexible protrusion 3005 can be made from compressible foam. In an example, flexible protrusion 3005 can be filled with a gas or liquid. In an example, the extension of flexible protrusion 3005 can be adjusted by adjusting the amount and/or pressure of a gas or liquid inside it. Metric equivalents can also be used for inch measurements. Other relevant components and design variations discussed elsewhere in this disclosure or priority-linked disclosures can also be incorporated into this example.

FIG. 4 shows a top-down view of an example of how this invention can be embodied in EEG glasses or other electroencephalographic eyewear comprising: (a) an eyewear frame which further comprises front section 4003 which is configured to span the front of a person's head, first side section 4001 which is configured to span from a first ear to front section 4003, and second side section 4002 which is configured to span from a second ear to front section 4003; (b) elliptical or oval flexible protrusion 4005 which is part of, or attached to, selected side section 4001; (c) electromagnetic energy sensor 4004 which collects data concerning electromagnetic brain activity; wherein flexible protrusion 4005 is configured to hold electromagnetic energy sensor 4004 on the person's head; (d) energy source 4006; (e) data processor 4007; and (f) data transmitter and/or receiver 4008.

In an example, a protrusion can be part of, or attached to, a selected side section, wherein the upper perimeter of the protrusion is not more than ¼" higher than the upper perimeter of the selected side section, and wherein the lower perimeter of the protrusion is not more than ¼" lower than the lower perimeter of the selected side section. In an example, flexible protrusion 4005 can be made from compressible foam. In an example, flexible protrusion 4005 can be filled with a gas or liquid. In an example, the extension of flexible protrusion 4005 can be adjusted by adjusting the amount and/or pressure of a gas or liquid inside it. Metric equivalents can also be used for inch measurements. Other relevant components and design variations discussed elsewhere in this disclosure or priority-linked disclosures can also be incorporated into this example.

Figure 5:
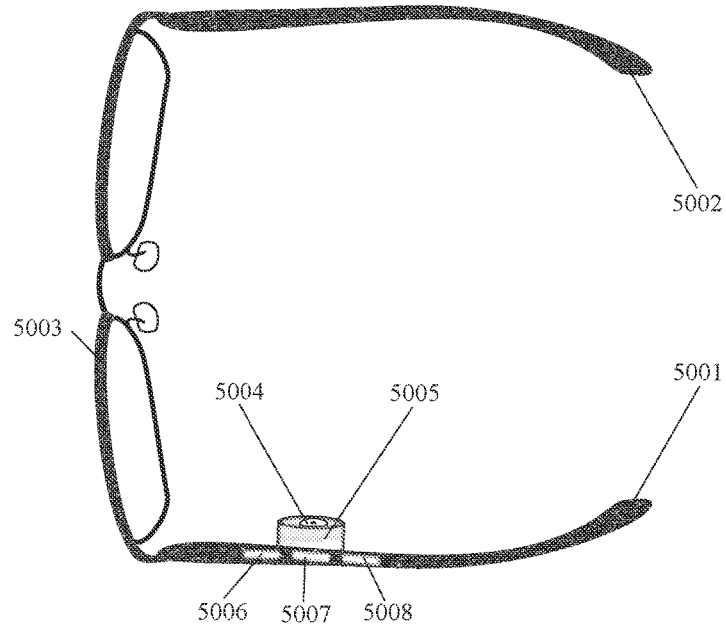
FIG. 5 shows EEG glasses with a cylindrical or rectangular protrusion on a side section.

FIG. 5 shows a top-down view of an example of how this invention can be embodied in EEG glasses or other electroencephalographic eyewear comprising: (a) an eyewear frame which further comprises front section 5003 which is configured to span the front of a person's head, first side section 5001 which is configured to span from a first ear to front section 5003, and second side section 5002 which is configured to span from a second ear to front section 5003; (b) cylindrical or rectangular protrusion 5005 which is part of, or attached to, selected side section 5001; (c) electromagnetic energy sensor 5004 which collects data concerning electromagnetic brain activity; wherein cylindrical protrusion 5005 is configured to hold electromagnetic energy sensor 5004 on the person's head; (d) energy source 5006; (e) data processor 5007; and (f) data transmitter and/or receiver 5008.

In an example, a protrusion can be part of, or attached to, a selected side section, wherein the upper perimeter of the protrusion is not more than ¼" higher than the upper perimeter of the selected side section, and wherein the lower perimeter of the protrusion is not more than ¼" lower than the lower perimeter of the selected side section. In an example, protrusion 5005 can be made from compressible foam. In an example, protrusion 5005 can be filled with a gas or liquid. In an example, the extension of protrusion 5005 can be adjusted by adjusting the amount and/or pressure of a gas or liquid inside it. Metric equivalents can also be used for inch measurements. Other relevant components and design variations discussed elsewhere in this disclosure or priority-linked disclosures can also be incorporated into this example.

Figure 6:
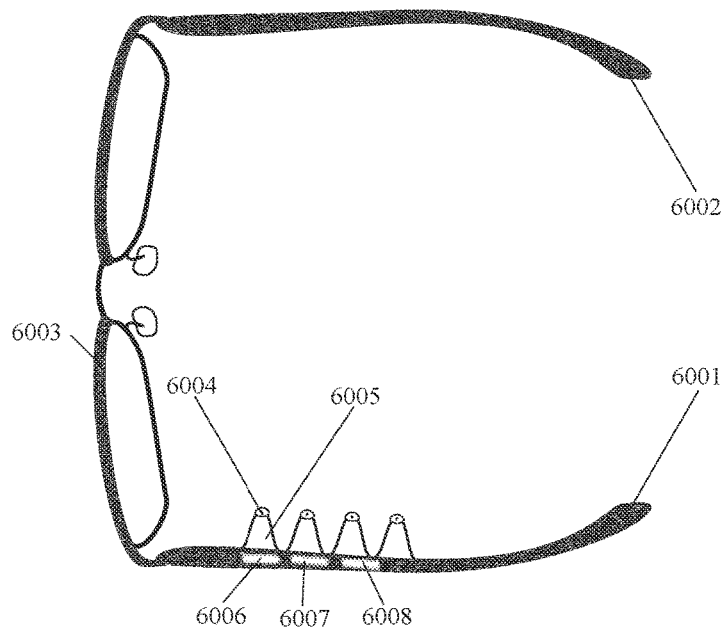
FIG. 6 shows EEG glasses with multiple sinusoidal protrusions on a side section.

FIG. 6 shows a top-down view of an example of how this invention can be embodied in EEG glasses or other electroencephalographic eyewear comprising: (a) an eyewear frame which further comprises front section 6003 which is configured to span the front of a person's head, first side section 6001 which is configured to span from a first ear to front section 6003, and second side section 6002 which is configured to span from a second ear to front section 6003; (b) a plurality of arcuate (sinusoidal) protrusions, including 6005, which are part of, or attached to, selected side section 6001; (c) a plurality of electromagnetic energy sensors, including 6004, which collect data concerning electromagnetic brain activity; wherein the plurality of protrusions are configured to hold the plurality of electromagnetic energy sensors on the person's head; (d) energy source 6006; (e) data processor 6007; and (f) data transmitter and/or receiver 6008.

In an example, protrusions can be part of, or attached to, a selected side section, wherein the upper perimeters of the protrusions are not more than ¼" higher than the upper perimeter of the selected side section, and wherein the lower perimeter of the protrusion is not more than ¼" lower than the lower perimeter of the selected side section. In an example, protrusions can be made from compressible foam. In an example, protrusions can be filled with a gas or liquid. In an example, extension of the protrusions can be adjusted by adjusting the amounts and/or pressures of gases or liquids inside them. Metric equivalents can also be used for inch measurements. Other relevant components and design variations discussed elsewhere in this disclosure or priority-linked disclosures can also be incorporated into this example.

Figure 7:
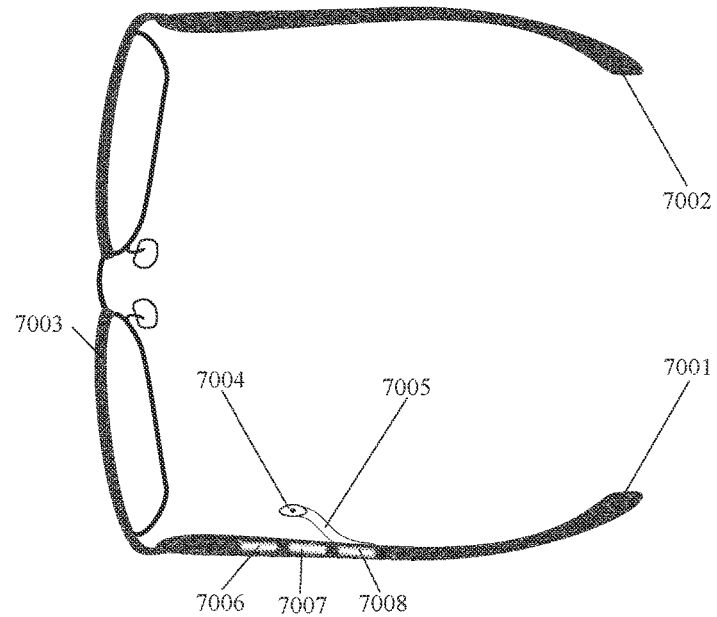
FIG. 7 shows EEG glasses with an arcuate tensile protrusion on a side section.

FIG. 7 shows a top-down view of an example of how this invention can be embodied in EEG glasses or other electroencephalographic eyewear comprising: (a) an eyewear frame which further comprises front section 7003 which is configured to span the front of a person's head, first side section 7001 which is configured to span from a first ear to front section 7003, and second side section 7002 which is configured to span from a second ear to front section 7003; (b) an arcuate tensile protrusion 7005 which is part of, or attached to, selected side section 7001; (c) an electromagnetic energy sensor 7004 which collects data concerning electromagnetic brain activity; wherein the protrusion is configured to hold the electromagnetic energy sensor on the person's head; (d) energy source 7006; (e) data processor 7007; and (f) data transmitter and/or receiver 7008.

In an example, the protrusion can be part of, or attached to, a selected side section, wherein the upper perimeter of the protrusion is not more than ¼" higher than the upper perimeter of the selected side section, and wherein the lower perimeter of the protrusion is not more than ¼" lower than the lower perimeter of the selected side section. In this example, the posterior (rear) end of the protrusion is directly attached to the selected side section and the anterior (front) end of the protrusion is not directly attached to the selected side section. In an example, the protrusion can have a half-sinusoidal shape. Metric equivalents can also be used for inch measurements. Other relevant components and design variations discussed elsewhere in this disclosure or priority-linked disclosures can also be incorporated into this example.

Figure 8:
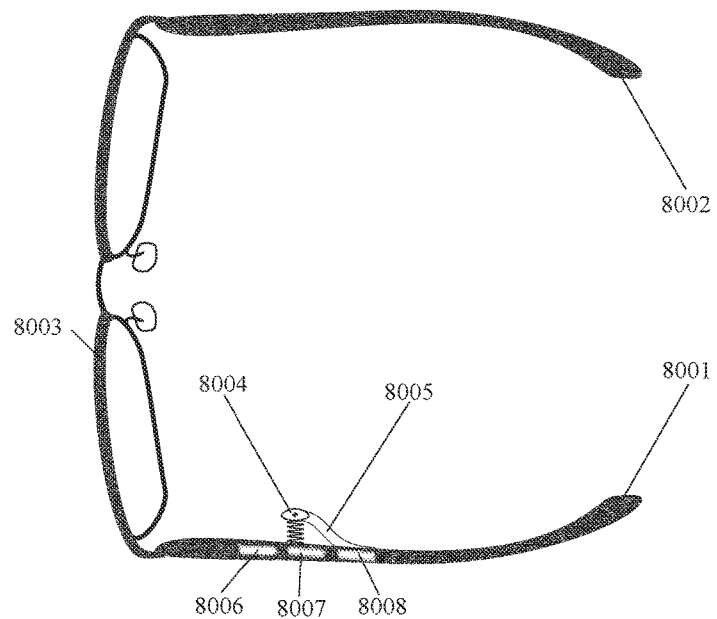
FIG. 8 shows EEG glasses with a spring-attached tensile protrusion on a side section.

FIG. 8 shows a top-down view of an example of how this invention can be embodied in EEG glasses or other electroencephalographic eyewear comprising: (a) an eyewear frame which further comprises front section 8003 which is configured to span the front of a person's head, first side section 8001 which is configured to span from a first ear to front section 8003, and second side section 8002 which is configured to span from a second ear to front section 8003; (b) an arcuate tensile protrusion 8005 which is part of, or attached to, selected side section 8001; (c) an electromagnetic energy sensor 8004 which collects data concerning electromagnetic brain activity; wherein the protrusion is configured to hold the electromagnetic energy sensor on the person's head; (d) energy source 8006; (e) data processor 8007; and (f) data transmitter and/or receiver 8008.

In an example, a protrusion can be part of, or attached to, a selected side section, wherein the upper perimeter of the protrusion is not more than ¼" higher than the upper perimeter of the selected side section, and wherein the lower perimeter of the protrusion is not more than ¼" lower than the lower perimeter of the selected side section. In this example, there is a spring between the anterior (front) end of the arcuate protrusion and the selected side section. Metric equivalents can also be used for inch measurements. Other relevant components and design variations discussed elsewhere in this disclosure or priority-linked disclosures can also be incorporated into this example.

Figure 9:
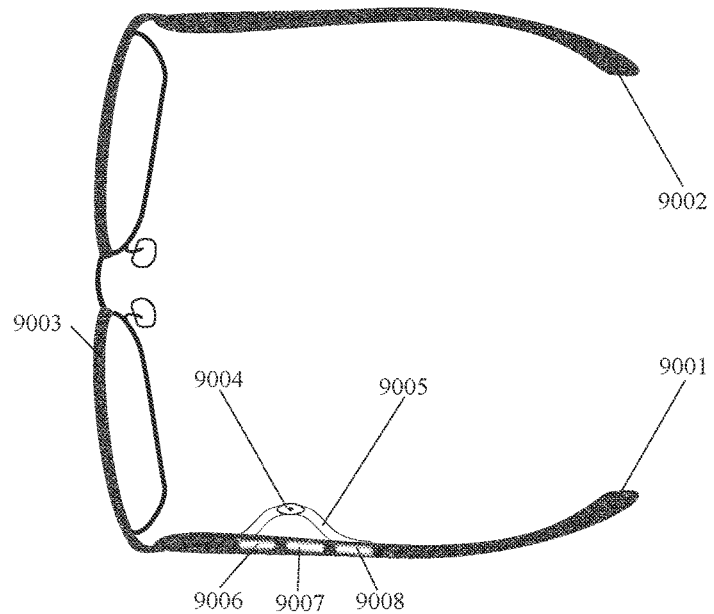
FIG. 9 shows EEG glasses with a sinusoidal tensile protrusion on a side section.

FIG. 9 shows a top-down view of an example of how this invention can be embodied in EEG glasses or other electroencephalographic eyewear comprising: (a) an eyewear frame which further comprises front section 9003 which is configured to span the front of a person's head, first side section 9001 which is configured to span from a first ear to front section 9003, and second side section 9002 which is configured to span from a second ear to front section 9003; (b) an arcuate tensile protrusion 9005 which is part of, or attached to, selected side section 9001; (c) an electromagnetic energy sensor 9004 which collects data concerning electromagnetic brain activity; wherein the protrusion is configured to hold the electromagnetic energy sensor on the person's head; (d) energy source 9006; (e) data processor 9007; and (f) data transmitter and/or receiver 9008.

In an example, a protrusion can be part of, or attached to, a selected side section, wherein the upper perimeter of the protrusion is not more than ¼" higher than the upper perimeter of the selected side section, and wherein the lower perimeter of the protrusion is not more than ¼" lower than the lower perimeter of the selected side section. In this example, both the posterior (rear) end and the anterior (front) end of the arcuate tensile protrusion are directly attached to the selected side section, but the middle of the arcuate tensile protrusion between these ends is not directly attached to the selected side section. Metric equivalents can also be used for inch measurements. Other relevant components and design variations discussed elsewhere in this disclosure or priority-linked disclosures can also be incorporated into this example.

Figure 10:
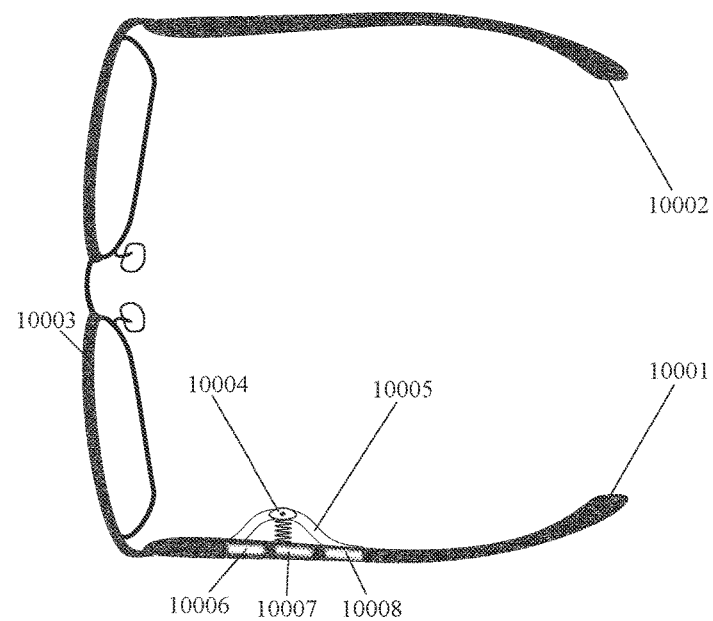
FIG. 10 shows EEG glasses with a spring-attached sinusoidal tensile protrusion on a side section.

FIG. 10 shows a top-down view of an example of how this invention can be embodied in EEG glasses or other electro-encephalographic eyewear comprising: (a) an eyewear frame which further comprises front section 10003 which is configured to span the front of a person's head, first side section 10001 which is configured to span from a first ear to front section 10003, and second side section 10002 which is configured to span from a second ear to front section 10003; (b) arcuate tensile protrusion 10005 which is part of, or attached to, selected side section 10001; (c) electromagnetic energy sensor 10004 which collects data concerning electromagnetic brain activity; wherein the protrusion is configured to hold the electromagnetic energy sensor on the person's head; (d) energy source 10006; (e) data processor 10007; and (f) data transmitter and/or receiver 10008.

In an example, a protrusion can be part of, or attached to, a selected side section, wherein the upper perimeter of the protrusion is not more than 1/4" higher than the upper perimeter of the selected side section, and wherein the lower perimeter of the protrusion is not more than 1/4" lower than the lower perimeter of the selected side section. In this example: both the posterior (rear) end and the anterior (front) end of the arcuate tensile protrusion are directly attached to the selected side section; and there is a spring between the middle portion of the arcuate tensile protrusion and the selected side section. Metric equivalents can also be used for inch measurements. Other relevant components and design variations discussed elsewhere in this disclosure or priority-linked disclosures can also be incorporated into this example.

Figure 11:
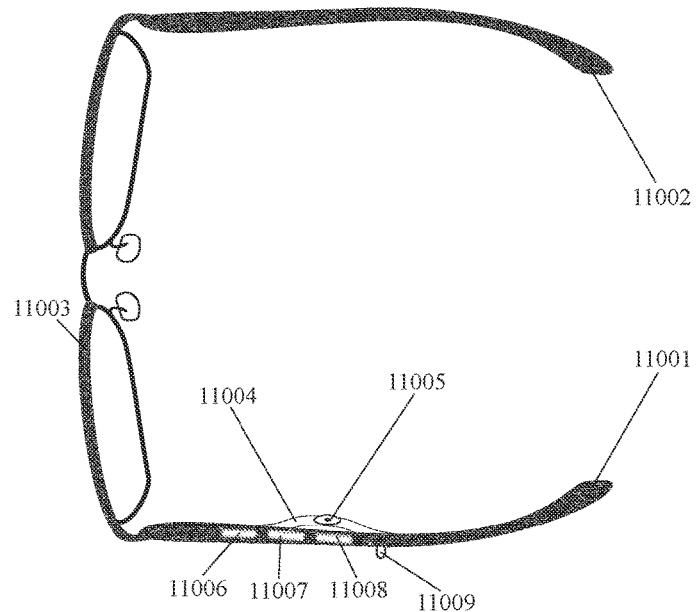
FIGS. 11 and 12 show how an arcuate tensile protrusion on EEG glasses can be adjusted.
Figure 12:
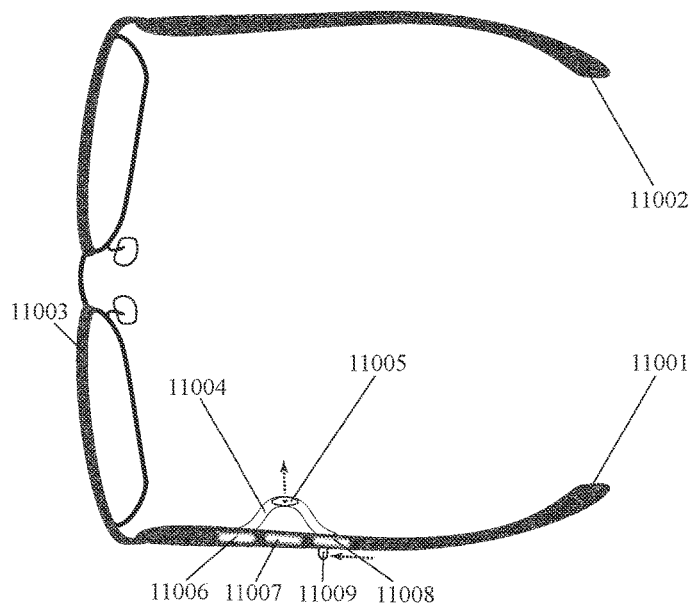

FIGS. 11 and 12 show two sequential top-down views of an example showing how a flexible protrusion which holds an electromagnetic energy sensor can be adjusted. This example comprises: (a) an eyewear frame which further comprises front section 11003 which is configured to span the front of a person's head, first side section 11001 which is configured to span from a first ear to front section 11003, and second side section 11002 which is configured to span from a second ear to front section 11003; (b) flexible protrusion 11004 which is part of, or attached to, selected side section 11001; (c) electromagnetic energy sensor 11005 which collects data concerning electromagnetic brain activity; wherein the protrusion is configured to hold the electromagnetic energy sensor on the person's head; (d) energy source 11006; (e) data processor 11007; (f) data transmitter and/or receiver 11008; and (g) sliding knob 11009.

In this example, flexible protrusion 11004 has a first configuration in which it extends a first distance from the selected side section toward a person's head, has a second configuration in which it extends a second distance from the selected side section toward the person's head, the second distance is greater than the first distance, and the flexible protrusion can be reversibly adjusted (moved or changed) from the first configuration to the second configuration. FIG. 11 shows the flexible protrusion in its first configuration and FIG. 12 shows the flexible protrusion in its second configuration.

In this example, the flexible protrusion is adjusted (moved or changed) from its first configuration to its second configuration by manually moving sliding knob 11009, which moves one end of the flexible protrusion closer to the other end of the flexible protrusion and causes the middle of the flexible protrusion to bulge (further) towards the person's head. In this example, one end of the flexible protrusion is slid closer to the other end along a track or channel, causing the middle of the flexible protrusion to bulge (further) outwards toward the person's head. In another example, a flexible protrusion can be automatically moved from its first configuration to its second configuration by an actuator. Metric equivalents can also be used for inch measurements. Other relevant components and design variations discussed elsewhere in this disclosure or priority-linked disclosures can also be incorporated into this example.

Figure 13:
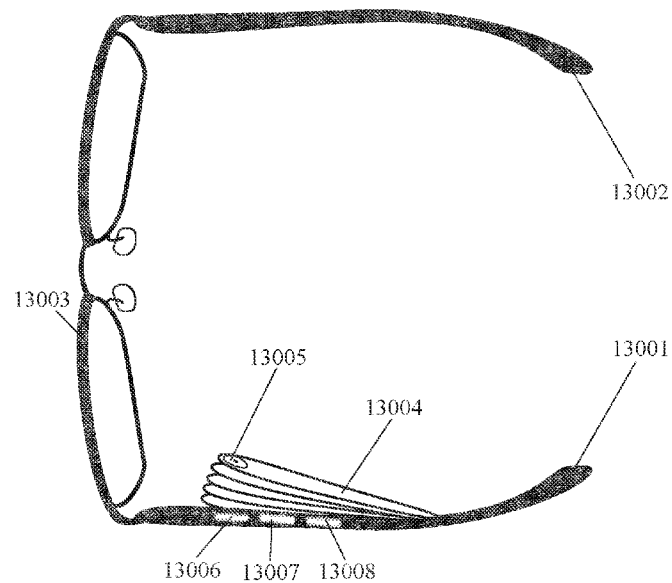
FIG. 13 shows EEG glasses with a folded and/or pleated protrusion on a side section.

FIG. 13 shows a top-down view of an example of how this invention can be embodied in EEG glasses or other electro-encephalographic eyewear comprising: (a) an eyewear frame which further comprises front section 13003 which is configured to span the front of a person's head, first side section 13001 which is configured to span from a first ear to front section 13003, and second side section 13002 which is configured to span from a second ear to front section 13003; (b) a folded and/or pleated protrusion 13004 which is part of, or attached to, selected side section 13001; (c) an electromagnetic energy sensor 13005 which collects data concerning electromagnetic brain activity; wherein the protrusion is configured to hold the electromagnetic energy sensor on the person's head; (d) energy source 13006; (e) data processor 13007; and (f) data transmitter and/or receiver 13008.

In an example, the protrusion can be part of, or attached to, a selected side section, wherein the upper perimeter of the protrusion is not more than 1/4" higher than the upper perimeter of the selected side section, and wherein the lower perimeter of the protrusion is not more than 1/4" lower than the lower perimeter of the selected side section. In an example, a folded and/or pleated protrusion can be extended (further) from the side section toward the person's head by filling the protrusion with a gas or liquid. In this example, the folded and/or pleated protrusion is shaped like a bellows or accordion. Metric equivalents can also be used for inch measurements. Other relevant components and design variations discussed elsewhere in this disclosure or priority-linked disclosures can also be incorporated into this example.

Figure 14:
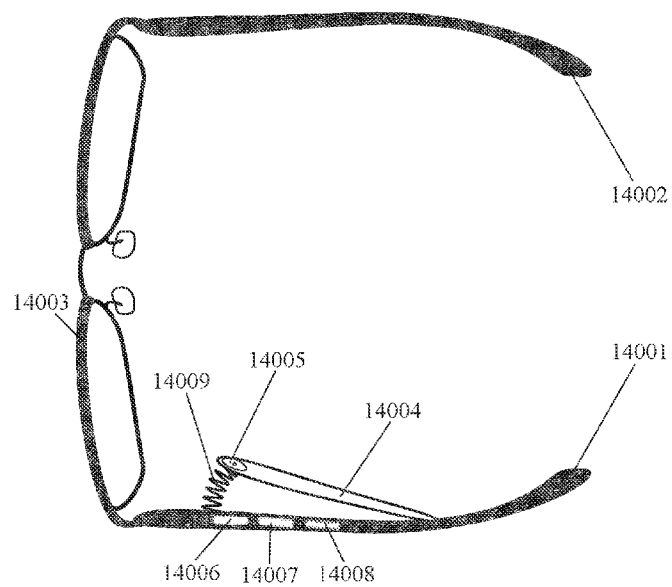
FIG. 14 shows EEG glasses with a spring-attached pivoting protrusion on a side section.

FIG. 14 shows a top-down view of an example of how this invention can be embodied in EEG glasses or other electro-encephalographic eyewear comprising: (a) an eyewear frame which further comprises front section 14003 which is configured to span the front of a person's head, first side section 14001 which is configured to span from a first ear to front section 14003, and second side section 14002 which is configured to span from a second ear to front section 14003; (b) a pivoting protrusion 14004 which is part of, or attached to, selected side section 14001; (c) an electromagnetic energy sensor 14005 which collects data concerning electromagnetic brain activity; wherein the protrusion is configured to hold the electromagnetic energy sensor on the person's head; (d) energy source 14006; (e) data processor 14007; and (f) data transmitter and/or receiver 14008.

In an example, the protrusion can be part of, or attached to, a selected side section, wherein the upper perimeter of the protrusion is not more than 1/4" higher than the upper perimeter of the selected side section, and wherein the lower perimeter of the protrusion is not more than 1/4" lower than the lower perimeter of the selected side section. In this example, there is a spring 14009 between the pivoting protrusion and the side section. Metric equivalents can also be used for inch measurements. Other relevant components and design variations discussed elsewhere in this disclosure or priority-linked disclosures can also be incorporated into this example.

FIG. 15 shows a top-down view of an example of how this invention can be embodied in EEG glasses or other electroencephalographic eyewear comprising: (a) an eyewear frame which further comprises front section 15003 which is configured to span the front of a person's head, first side section 15001 which is configured to span from a first ear to front section 15003, and second side section 15002 which is configured to span from a second ear to front section 15003; (b) a wedge-shaped flexible protrusion 15004 which is part of, or attached to, selected side section 15001; (c) an electromagnetic energy sensor 15005 which collects data concerning electromagnetic brain activity; wherein the protrusion is configured to hold the electromagnetic energy sensor on the person's head; (d) energy source 15006; (e) data processor 15007; and (f) data transmitter and/or receiver 15008.

In an example, the protrusion can be part of, or attached to, a selected side section, wherein the upper perimeter of the protrusion is not more than ¼" higher than the upper perimeter of the selected side section, and wherein the lower perimeter of the protrusion is not more than ¼" lower than the lower perimeter of the selected side section. In this example, the wedge-shaped protrusion is made from compressible foam. Metric equivalents can also be used for inch measurements. Other relevant components and design variations discussed elsewhere in this disclosure or priority-linked disclosures can also be incorporated into this example.

FIG. 16 shows a top-down view of an example of how this invention can be embodied in EEG glasses or other electroencephalographic eyewear comprising: (a) an eyewear frame which further comprises front section 16003 which is configured to span the front of a person's head, first side section 16001 which is configured to span from a first ear to front section 16003, and second side section 16002 which is configured to span from a second ear to front section 16003; (b) a wedge-shaped flexible protrusion 16004 which is part of, or attached to, selected side section 16001; (c) an electromagnetic energy sensor 16005 which collects data concerning electromagnetic brain activity; wherein the protrusion is configured to hold the electromagnetic energy sensor on the person's head; (d) energy source 16006; (e) data processor 16007; (0 data transmitter and/or receiver 16008; and pump 16009.

In an example, the protrusion can be part of, or attached to, a selected side section, wherein the upper perimeter of the protrusion is not more than ¼" higher than the upper perimeter of the selected side section, and wherein the lower perimeter of the protrusion is not more than ¼" lower than the lower perimeter of the selected side section. In this example, the wedge-shaped protrusion can be inflated or deflated by activation of pump 16009. Metric equivalents can also be used for inch measurements. Other relevant components and design variations discussed elsewhere in this disclosure or priority-linked disclosures can also be incorporated into this example.

Figure 17:
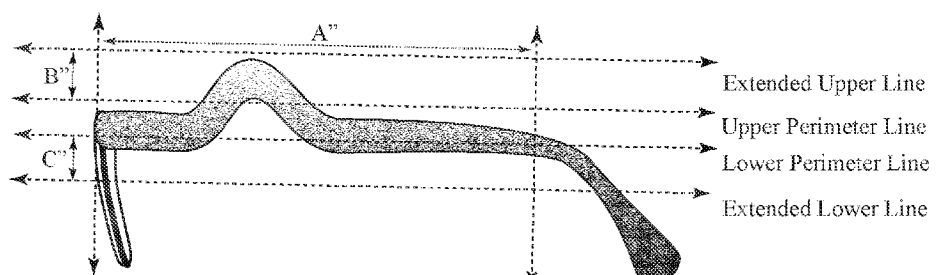
FIGS. 17 and 18 show two views of EEG glasses with an upward wave on a side section.
Figure 18:
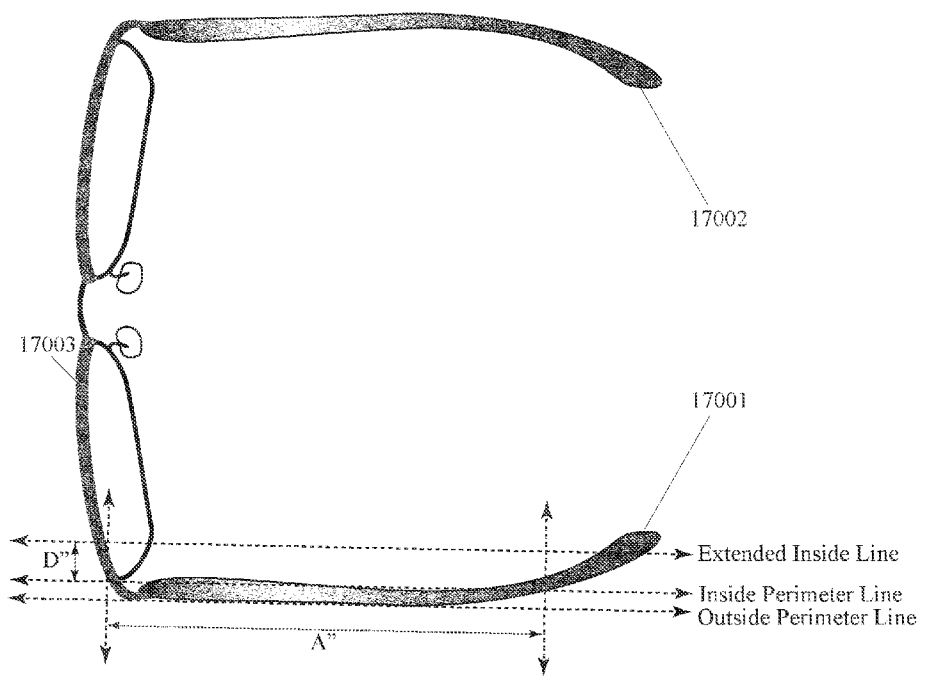

FIGS. 17 and 18 show a side view and a top-down view, respectively, of an eyewear frame with an upward (sinusoidal) wave which comprises a front section 17003 which is configured to span the front of a person's head, a first side section 17001 which is configured to span from a first ear to the front section, and a second side section 17002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, then spans forward (1"-3") along a relatively-straight longitudinal axis, then curves upward and forward (1"-3") to a location over the person's temple and/or forehead, and then curves downward and forward to connect to the front section. FIGS. 17 and 18 also show how virtual reference lines can be defined relative to this type of eyewear frame. Metric equivalents can also be used for inch measurements.

Figure 19:
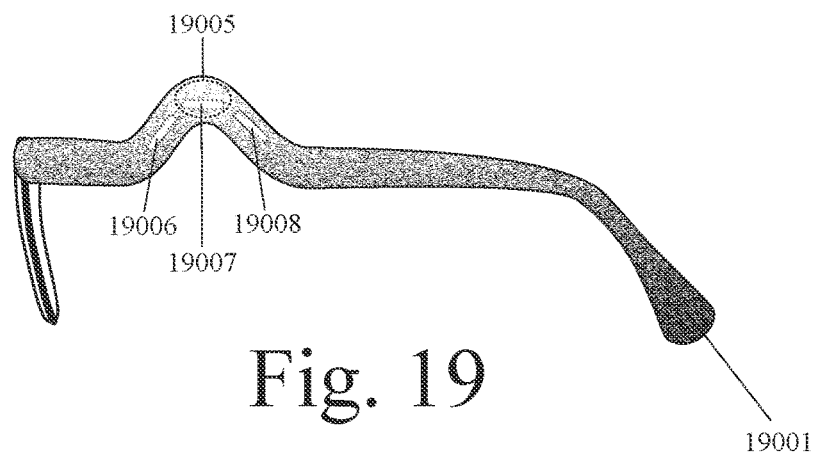
FIGS. 19 and 20 show two views of EEG glasses with an upward wave and flexible protrusion on a side section.
Figure 20:
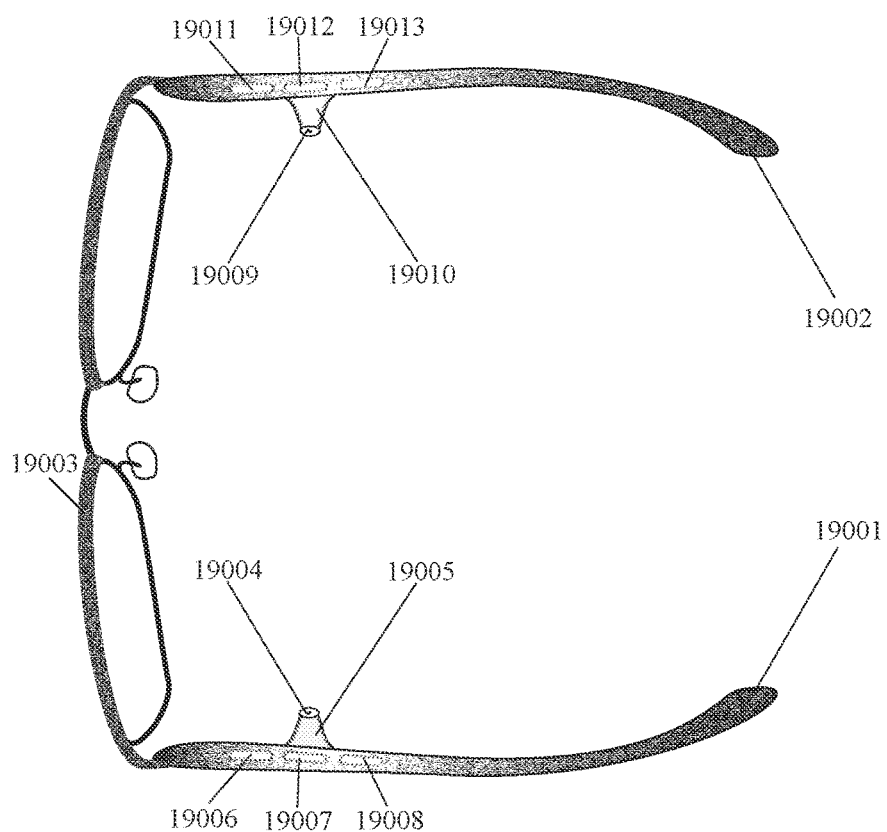

FIGS. 19 and 20 show an example of how this invention can be embodied in electroencephalographic eyewear with the type of upward-wave frame that was shown in FIGS. 17 and 18. FIG. 19 shows a side view. FIG. 20 shows a top-down view. Specifically, FIGS. 19 and 20 show an example of how this invention can be embodied in electroencephalographic eyewear comprising: (a) a frame for eyeglasses or other eyewear; wherein this frame further comprises front section 19003 which is configured to span the front of a person's head, first side section 19001 which is configured to span from a first ear to the front section, and second side section 19002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, then spans forward (1"-3") along a relatively-straight longitudinal axis, then curves upward and forward (1"-3") to a location over the person's temple and/or forehead, and then curves downward and forward to connect to the front section; (b) flexible protrusion 19005 which is part of, or attached to, first side section 19001; (c) electromagnetic energy sensor 19004 which collects data concerning electromagnetic brain activity; wherein flexible protrusion 19005 is configured to hold electromagnetic energy sensor 19004 on the person's head; (d) energy source 19006; (e) data processor 19007; and (f) data transmitter and/or receiver 19008.

The example shown in FIGS. 19 and 20 also has a (symmetric) set of components on the other side section, including second flexible protrusion 19010, second electromagnetic energy sensor 19009, second energy source 19011, second data processor 19012, and second data transmitter and/or receiver 19013. In an example, an electromagnetic energy sensor can be located at (or near) the top if the upward wave of the side section. Metric equivalents can also be used for inch measurements. Other relevant components and design variations discussed elsewhere in this disclosure or priority-linked disclosures can also be incorporated into this example.

Figure 21:
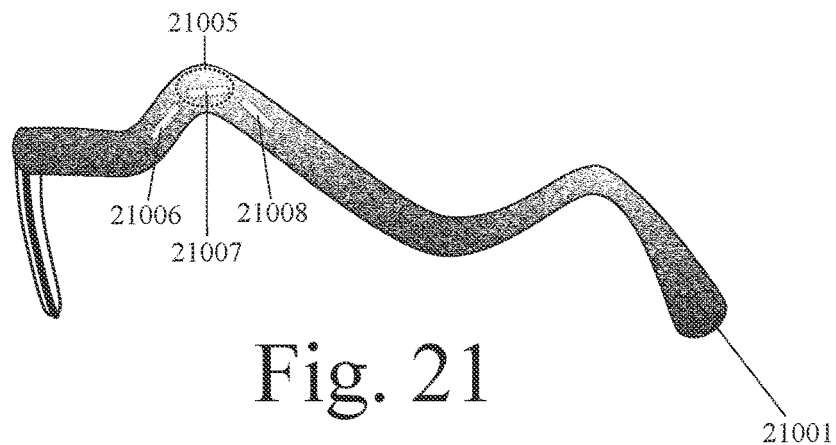
FIGS. 21 and 22 show two views of first example of EEG glasses with two upward waves on a side section.
Figure 22:
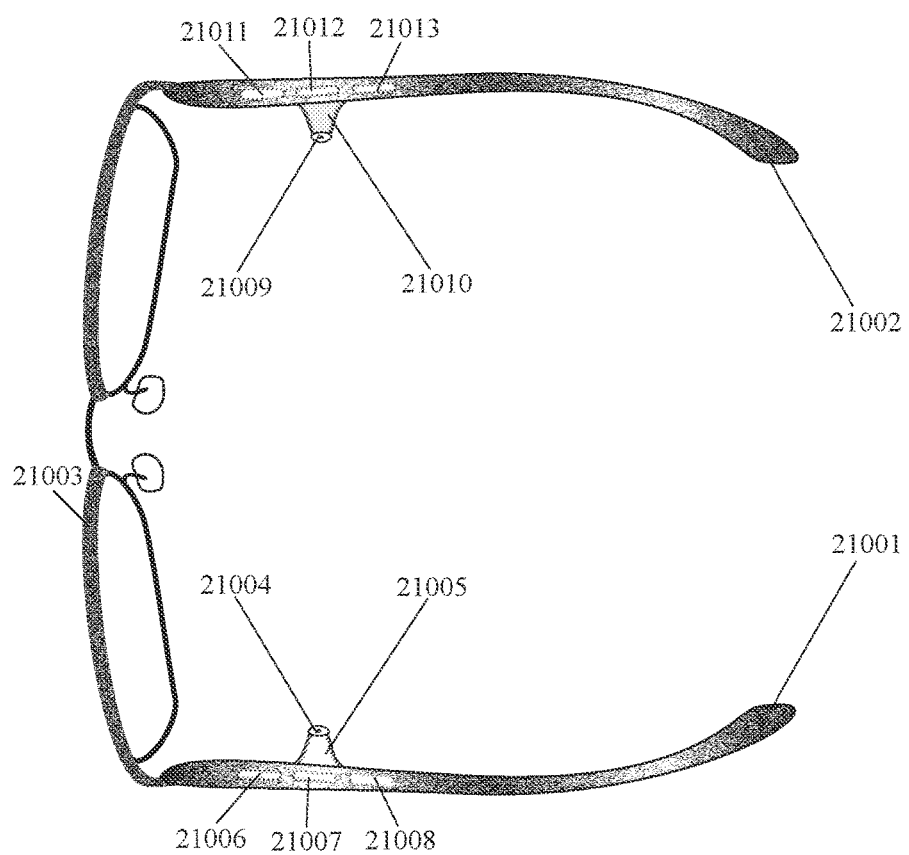

FIGS. 21 and 22 show an example of how this invention can be embodied in electroencephalographic eyewear with a (sinusoidal) undulating frame. FIG. 21 shows a side view. FIG. 22 shows a top-down view. Specifically, FIGS. 21 and 22 show an example of how this invention can be embodied in electroencephalographic eyewear comprising: (a) a frame for eyeglasses or other eyewear; wherein this frame further comprises front section 21003 which is configured to span the front of a person's head, first side section 21001 which is configured to span from a first ear to the front section, and second side section 21002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, then curves downward and forward (1"-3"), then curves upward and forward (1"-3") to a location over the person's temple and/or forehead, and then curves downward and forward to connect to the front section; (b) flexible protrusion 21005 which is part of, or attached to, selected side section 21001; (c) electromagnetic energy sensor 21004 which collects data concerning electromagnetic brain activity; wherein flexible protrusion 21005 is configured to hold electromagnetic energy sensor 21004 on the person's head; (d) energy source 21006; (e) data processor 21007; and (f) data transmitter and/or receiver 21008.

The example shown in FIGS. 21 and 22 also has a (symmetric) set of components on the other side section, including second flexible protrusion 21010, second electromagnetic energy sensor 21009, second energy source 21011, second data processor 21012, and second data transmitter and/or receiver 21013. Metric equivalents can also be used for inch measurements. Other relevant components and design variations discussed elsewhere in this disclosure or priority-linked disclosures can also be incorporated into this example.

Figure 23:
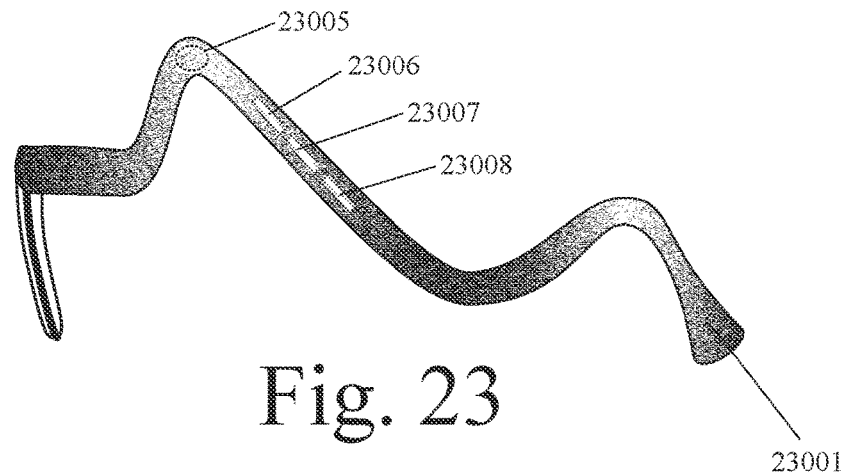
FIGS. 23 and 24 show two views of second example of EEG glasses with two upward waves on a side section.
Figure 24:
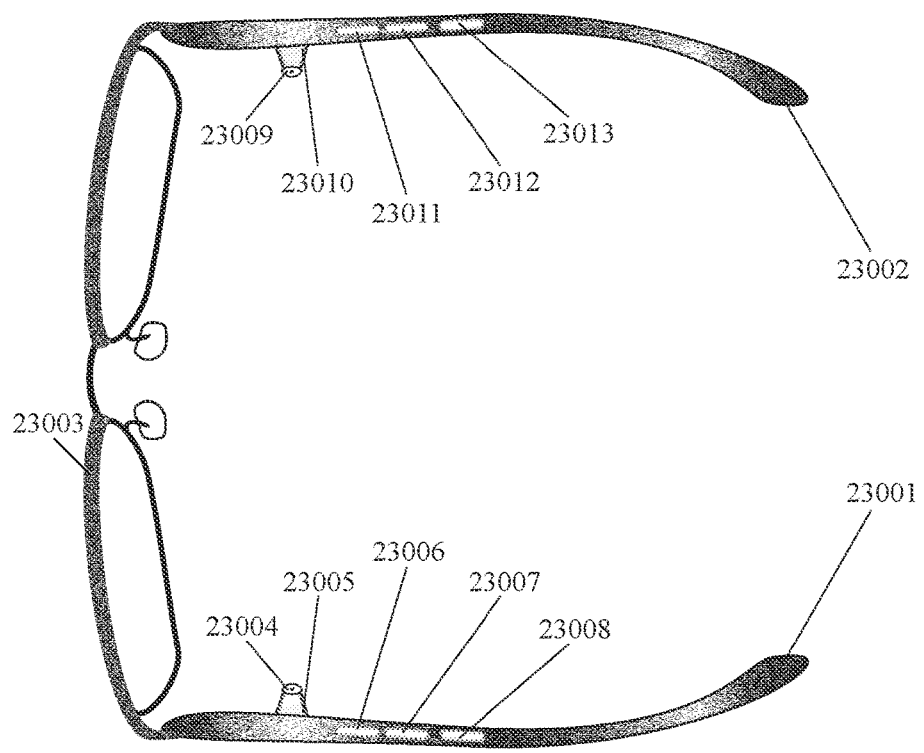

FIGS. 23 and 24 show another example of how this invention can be embodied in electroencephalographic eyewear with a (sinusoidal) undulating frame which is similar to the example shown in FIGS. 21 and 22 except that the energy source, data processor, and data transmitter and/or receiver are in a more-central location. FIG. 23 shows a side view. FIG. 24 shows a top-down view.

Specifically, FIGS. 23 and 24 show an example of how this invention can be embodied in electroencephalographic eyewear comprising: (a) a frame for eyeglasses or other eyewear; wherein this frame further comprises front section 23003 which is configured to span the front of a person's head, first side section 23001 which is configured to span from a first ear to the front section, and second side section 23002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, then curves downward and forward, then curves upward and forward to a location over the person's temple and/or forehead, and then curves downward and forward to connect to the front section; (b) flexible protrusion 23005 which is part of, or attached to, selected side section 23001; (c) electromagnetic energy sensor 23004 which collects data concerning electromagnetic brain activity; wherein flexible protrusion 23005 is configured to hold electromagnetic energy sensor 23004 on the person's head; (d) energy source 23006; (e) data processor 23007; and (f) data transmitter and/or receiver 23008.

The example shown in FIGS. 23 and 24 also has a (symmetric) set of components on the other side section, including second flexible protrusion 23010, second electromagnetic energy sensor 23009, second energy source 23011, second data processor 23012, and second data transmitter and/or receiver 23013. Metric equivalents can also be used for inch measurements. Other relevant components and design variations discussed elsewhere in this disclosure or priority-linked disclosures can also be incorporated into this example.

Figure 25:
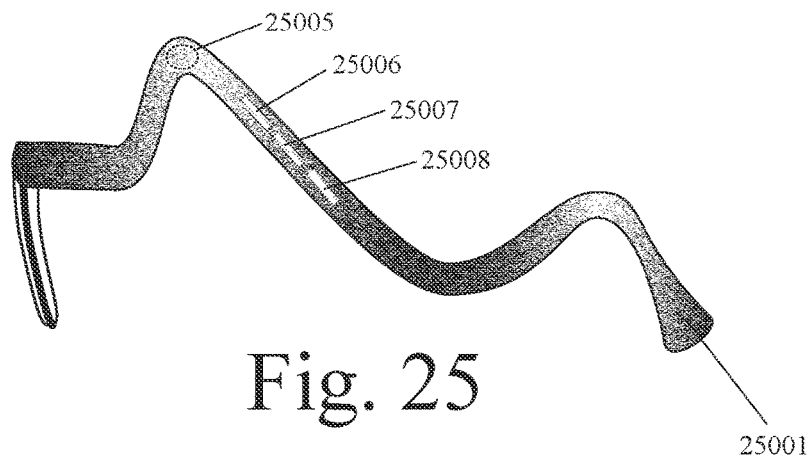
FIGS. 25 and 26 show two views of EEG glasses with two upward waves and an inward wave on a side section.
Figure 26:
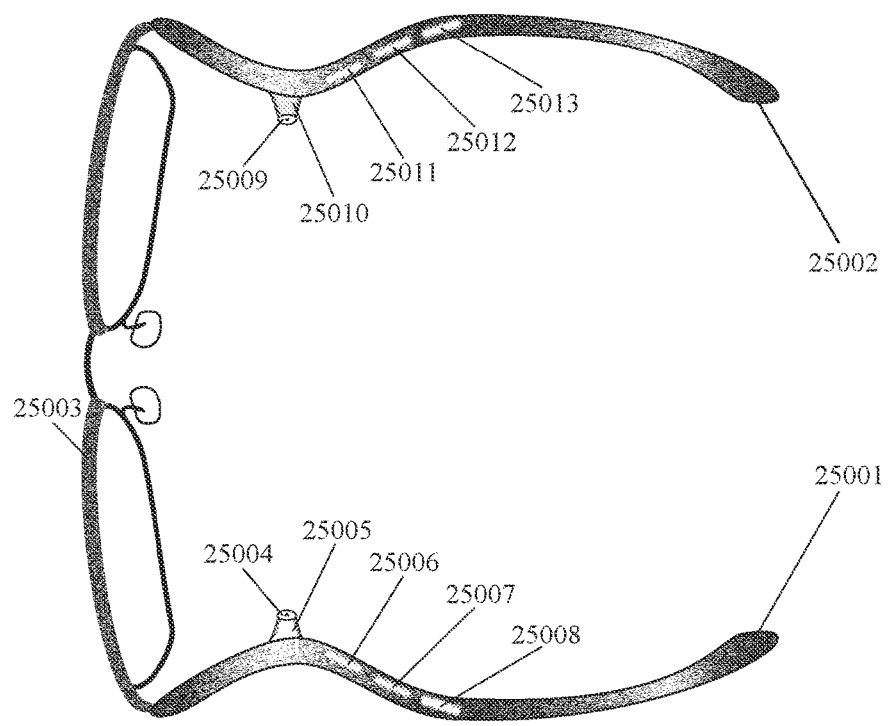

FIGS. 25 and 26 show another example of how this invention can be embodied in electroencephalographic eyewear with a (sinusoidal) undulating frame which is similar to the example shown in FIGS. 23 and 24 except that the anterior (upward wave) portions of the side sections bow inwards toward the person's forehead. In an example, virtual radial lines can be drawn which extend outward into space from the centroid (volume center or mass center) of a person's head. In an example, "outward" can be defined moving farther from this centroid along a virtual radial line and "inward" can be defined as moving closer to this centroid along a virtual radial line. FIG. 25 shows a side view. FIG. 26 shows a top-down view.

Specifically, FIGS. 25 and 26 show an example of how this invention can be embodied in electroencephalographic eyewear comprising: (a) a frame for eyeglasses or other eyewear; wherein this frame further comprises front section 25003 which is configured to span the front of a person's head, first side section 25001 which is configured to span from a first ear to the front section, and second side section 25002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, then curves downward and forward, then curves upward, forward, and inward to a location over the person's temple and/or forehead, and then curves downward, forward, and outward to connect to the front section; (b) flexible protrusion 25005 which is part of, or attached to, selected side section 25001; (c) electromagnetic energy sensor 25004 which collects data concerning electromagnetic brain activity; wherein flexible protrusion 25005 is configured to hold electromagnetic energy sensor 25004 on the person's head; (d) energy source 25006; (e) data processor 25007; and (f) data transmitter and/or receiver 25008.

The example shown in FIGS. 25 and 26 also has a (symmetric) set of components on the other side section, including second flexible protrusion 25010, second electromagnetic energy sensor 25009, second energy source 25011, second data processor 25012, and second data transmitter and/or receiver 25013. Metric equivalents can also be used for inch measurements. Other relevant components and design variations discussed elsewhere in this disclosure or priority-linked disclosures can also be incorporated into this example.

Figure 27:
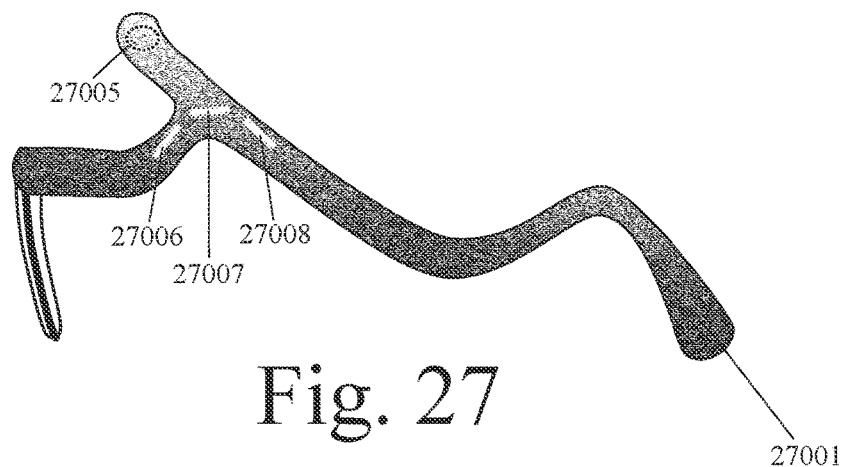
FIGS. 27 and 28 show two views of EEG glasses with two upward waves and a prong on a side section.
Figure 28:
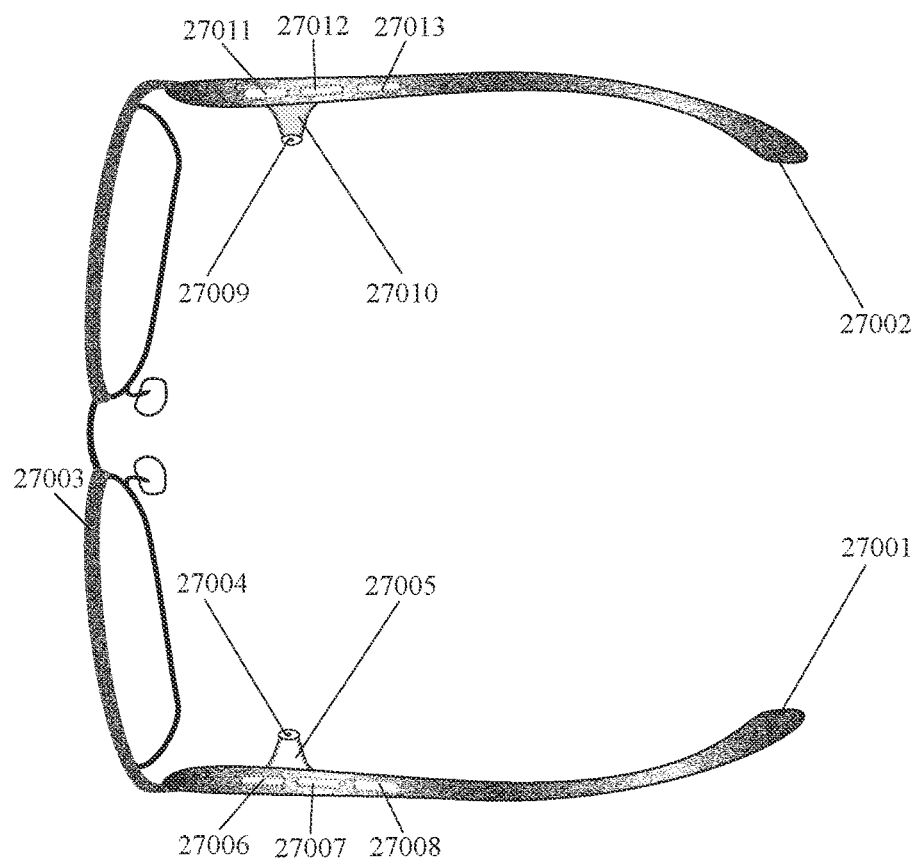

FIGS. 27 and 28 show another example of how this invention can be embodied in electroencephalographic eyewear wherein the side section of the frame has a bifurcation. This bifurcating frame has an upper arm (or projection) which curves up onto the side of the person's forehead. FIG. 27 shows a side view. FIG. 28 shows a top-down view.

Specifically, FIGS. 27 and 28 show an example of how this invention can be embodied in electroencephalographic eyewear comprising: (a) a frame for eyeglasses or other eyewear; wherein this frame further comprises front section 27003 which is configured to span the front of a person's head, first side section 27001 which is configured to span from a first ear to the front section, and second side section 27002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, then curves downward and forward, then curves upward and forward and bifurcates, wherein an upper portion of this bifurcation extends forward (at least ½") onto the side of the person's forehead and wherein a lower portion of this bifurcation curves forward to connect to the front section; (b) flexible protrusion 27005 which is part of, or attached to, selected side section 27001; (c) electromagnetic energy sensor 27004 which collects data concerning electromagnetic brain activity; wherein flexible protrusion 27005 is configured to hold electromagnetic energy sensor 27004 on the person's head; (d) energy source 27006; (e) data processor 27007; and (f) data transmitter and/or receiver 27008.

The example shown in FIGS. 27 and 28 also has a (symmetric) set of components on the other side section, including second flexible protrusion 27010, second electromagnetic energy sensor 27009, second energy source 27011, second data processor 27012, and second data transmitter and/or receiver 27013. Metric equivalents can also be used for inch measurements. Other relevant components and design variations discussed elsewhere in this disclosure or priority-linked disclosures can also be incorporated into this example.

Figure 29:
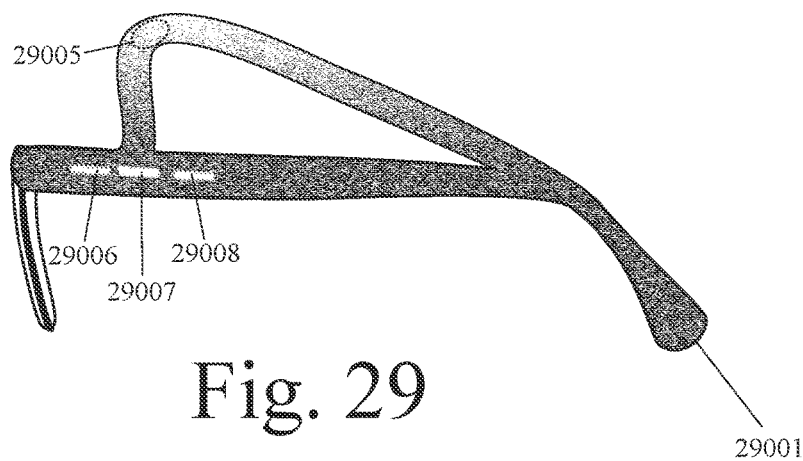
FIGS. 29 and 30 show two views of EEG glasses with a bifurcation on a side section.
Figure 30:
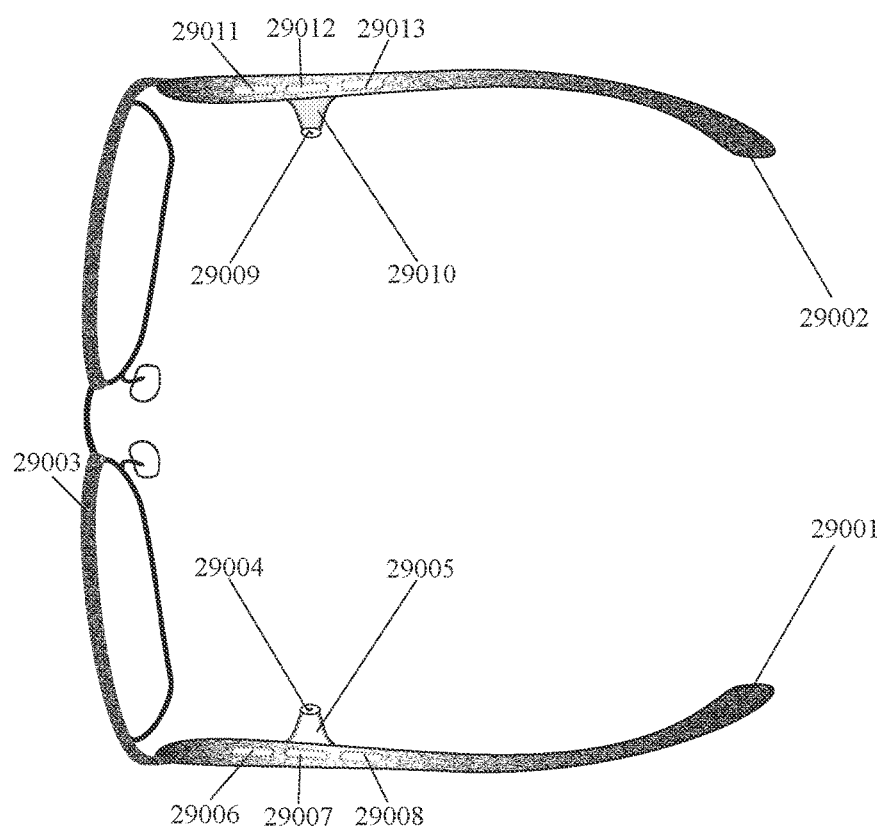

FIGS. 29 and 30 show another example of how this invention can be embodied in electroencephalographic eyewear wherein the side section of the frame has a bifurcation. In this frame, an upper portion of a bifurcation curves up onto the side of the person's forehead and then descends back down to reconnect to the lower portion. FIG. 29 shows a side view. FIG. 30 shows a top-down view.

Specifically, FIGS. 29 and 30 show an example of how this invention can be embodied in electroencephalographic eyewear comprising: (a) a frame for eyeglasses or other eyewear; wherein this frame further comprises front section 29003 which is configured to span the front of a person's head, first side section 29001 which is configured to span from a first ear to the front section, and second side section 29002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, and then bifurcates, wherein a lower portion of this bifurcation spans forward in a relatively-straight axial manner to connect to the front section and wherein an upper portion of this bifurcation curves up onto the side of the person's forehead and then descends to reconnect with the lower portion or front section; (b) flexible protrusion 29005 which is part of, or attached to, selected side section 29001; (c) electromagnetic energy sensor 29004 which collects data concerning electromagnetic brain activity; wherein flexible protrusion 29005 is configured to hold electromagnetic energy sensor 29004 on the person's head; (d) energy source 29006; (e) data processor 29007; and (f) data transmitter and/or receiver 29008.

The example shown in FIGS. 29 and 30 also has a (symmetric) set of components on the other side section, including second flexible protrusion 29010, second electromagnetic energy sensor 29009, second energy source 29011, second data processor 29012, and second data transmitter and/or receiver 29013. Metric equivalents can also be used for inch measurements. Other relevant components and design variations discussed elsewhere in this disclosure or priority-linked disclosures can also be incorporated into this example.

Figure 31:
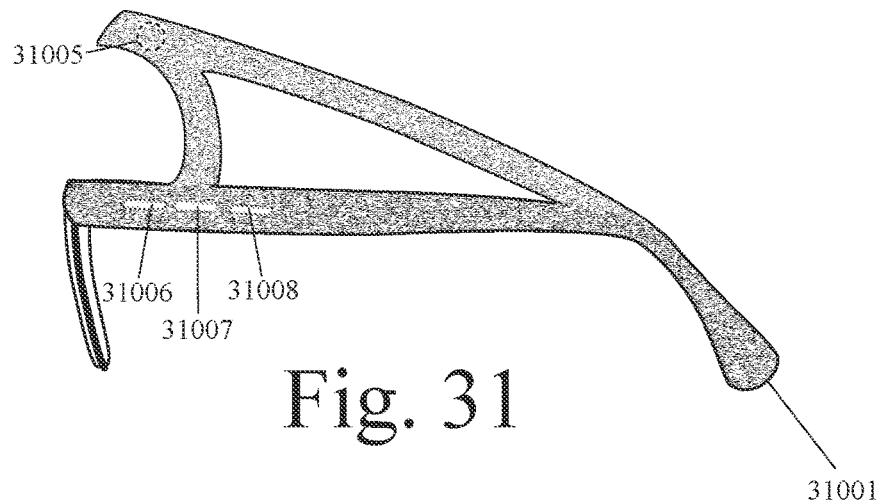
FIGS. 31 and 32 show two views of EEG glasses with a forehead-spanning curve.
Figure 32:
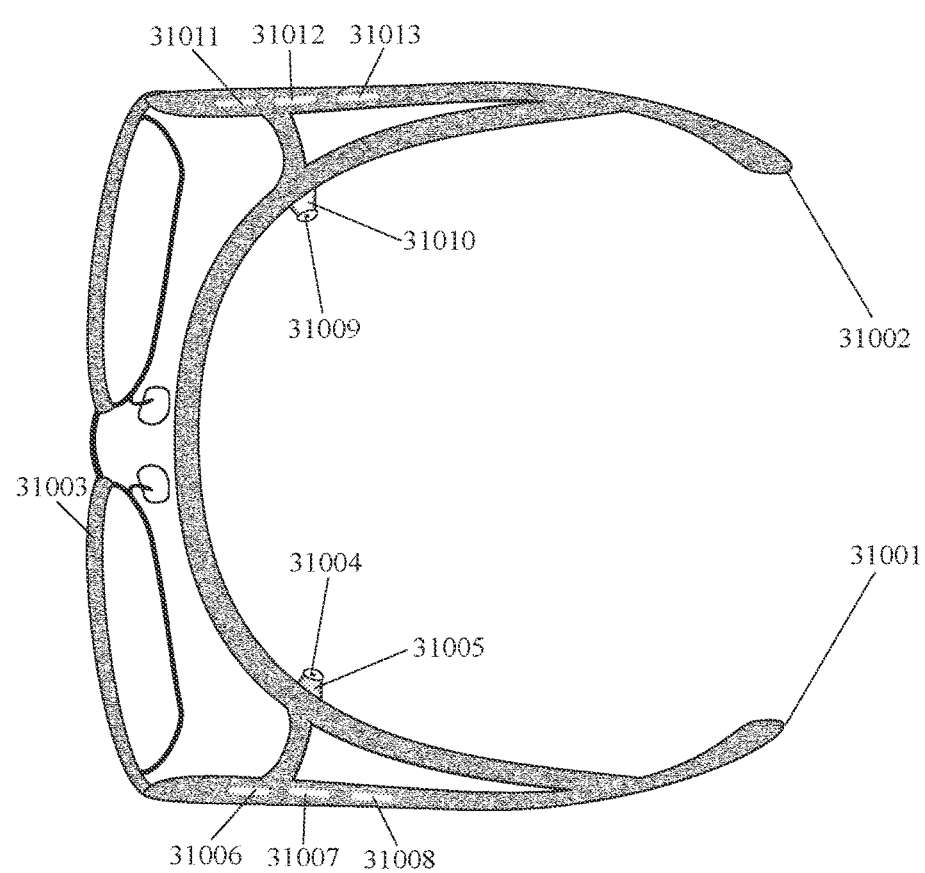

FIGS. 31 and 32 show an example of how this invention can be embodied in electroencephalographic eyewear that includes an upper (second) front section which curves entirely around a person's forehead. FIG. 31 shows a side view. FIG. 32 shows a top-down view.

Specifically, FIGS. 31 and 32 show an example of how this invention can be embodied in electroencephalographic eyewear comprising: (a) a frame for eyeglasses or other eyewear; wherein this frame further comprises front section 31003 which is configured to span the front of a person's head, first side section 31001 which is configured to span from a first ear to the front section, and second side section 31002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, and then bifurcates, wherein an upper portion of this bifurcation curves across the person's forehead above the front section and wherein a lower portion of this bifurcation spans forward in a relatively-straight axial manner to connect to the front section; (b) flexible protrusion 31005 which is part of, or attached to, selected side section 31001; (c) electromagnetic energy sensor 31004 which collects data concerning electromagnetic brain activity; wherein flexible protrusion 31005 is configured to hold electromagnetic energy sensor 31004 on the person's head; (d) energy source 31006; (e) data processor 31007; and (f) data transmitter and/or receiver 31008.

The example shown in FIGS. 31 and 32 also has a (symmetric) set of components on the other side section, including second flexible protrusion 31010, second electromagnetic energy sensor 31009, second energy source 31011, second data processor 31012, and second data transmitter and/or receiver 31013. In this example, there is also an anterior connecting strut (or connector) between the upper portion of the bifurcation and the lower portion of the bifurcation. In this example, this anterior connecting strut forms one side of a triangular gap, wherein the other two sides of this triangular gap are formed by the upper and lower portions of the bifurcation. In an example, the upper portion of the bifurcation can be transparent. In an example, the upper portion of the bifurcation can be made from fabric. In an example, the upper portion of the bifurcation can be elastic and/or stretchable. Metric equivalents can also be used for inch measurements. Other relevant components and design variations discussed elsewhere in this disclosure or priority-linked disclosures can also be incorporated into this example.

Figure 33:
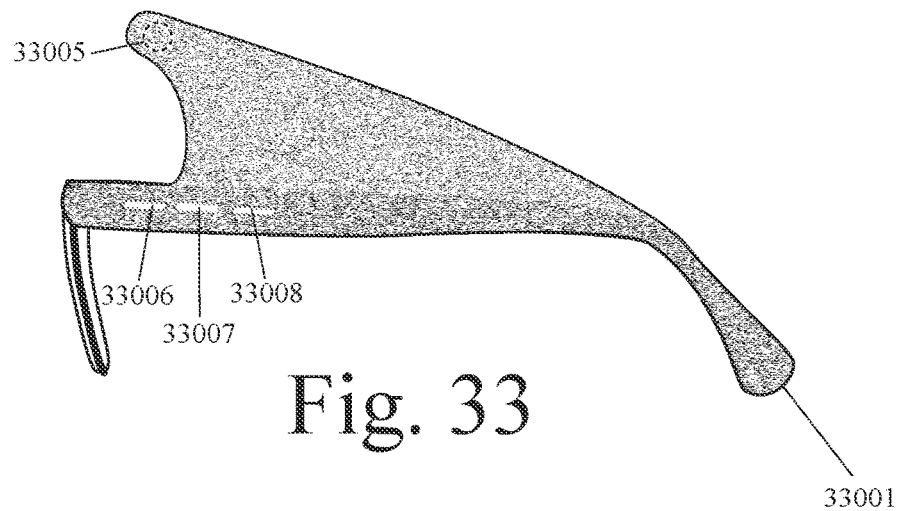
FIGS. 33 and 34 show two views of EEG glasses with an upward and inward curving fin or wedge.
Figure 34:
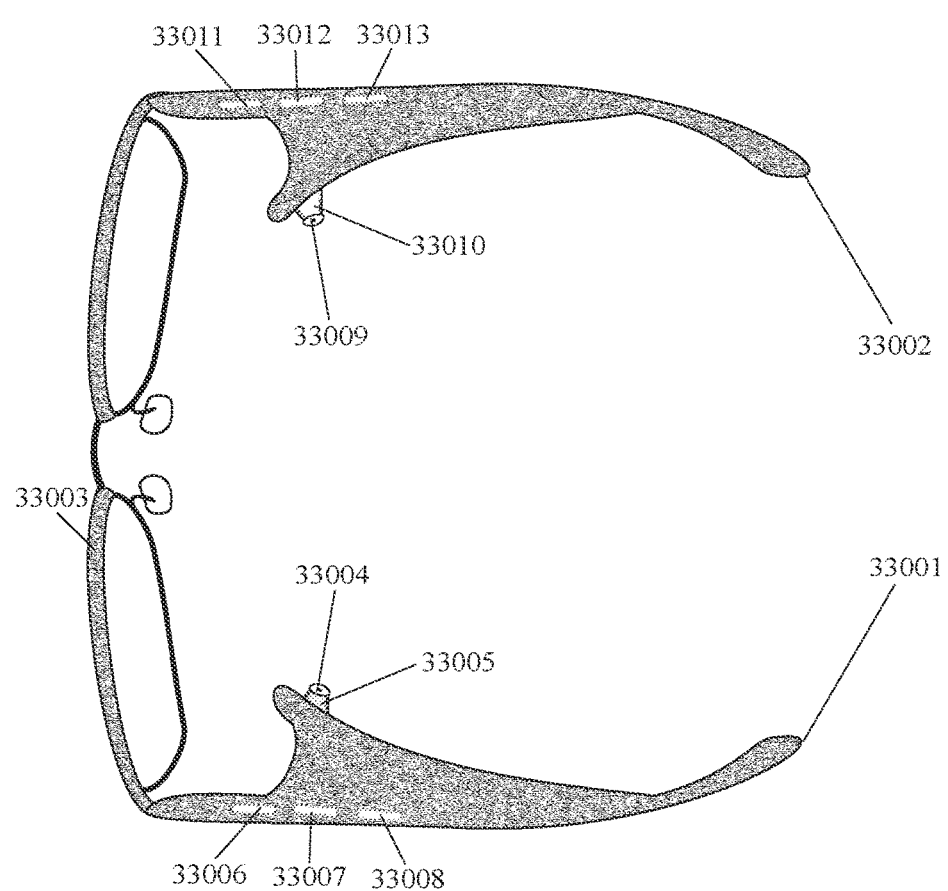

FIGS. 33 and 34 show an example of how this invention can be embodied in electroencephalographic eyewear with a fin or wedge shaped side portion which curves upward and inward onto the side of a person's forehead. FIG. 33 shows a side view. FIG. 34 shows a top-down view.

Specifically, FIGS. 33 and 34 show an example of how this invention can be embodied in electroencephalographic eyewear comprising: (a) a frame for eyeglasses or other eyewear; wherein this frame further comprises front section 33003 which is configured to span the front of a person's head, first side section 33001 which is configured to span from a first ear to the front section, and second side section 33002 which is configured to span from a second ear to the front section; wherein the first side section starts with a posterior end which is configured to be worn posterior to a person's ear, then curves upward and forward around the tissue connection between the person's outer ear to the rest of the person's head to the top of this tissue connection, and then widens (fans out, broadens, or expands) into a fin (wedge or triangular) shaped structure which is configured to curve upward and inward onto the side of the person's forehead and also connect to the front section; (b) flexible protrusion 33005 which is part of, or attached to, selected side section 33001; (c) electromagnetic energy sensor 33004 which collects data concerning electromagnetic brain activity; wherein flexible protrusion 33005 is configured to hold electromagnetic energy sensor 33004 on the person's head; (d) energy source 33006; (e) data processor 33007; and (f) data transmitter and/or receiver 33008.

The example shown in FIGS. 33 and 34 also has a (symmetric) set of components on the other side section, including second flexible protrusion 33010, second electromagnetic energy sensor 33009, second energy source 33011, second data processor 33012, and second data transmitter and/or receiver 33013. In an example, the fin (wedge or triangular) shaped structure in this example can be soft and compressible. In an example, the fin (wedge or triangular) shaped structure in this example can be made from compressible foam or be an inflatable member (such as a balloon). In an example, the fin (wedge or triangular) shaped structure in this example can be made from plastic or metal.

In an example, the fin (wedge or triangular) shaped structure can widen from a posterior portion width of less than ½" to an anterior width of greater than ½". In an example, the fin (wedge or triangular) shaped structure can widen from a posterior portion width of less than ½" to an anterior width of greater than ¾". Metric equivalents can also be used for inch measurements. Other relevant components and design variations discussed elsewhere in this disclosure or priority-linked disclosures can also be incorporated into this example.

Figure 35:
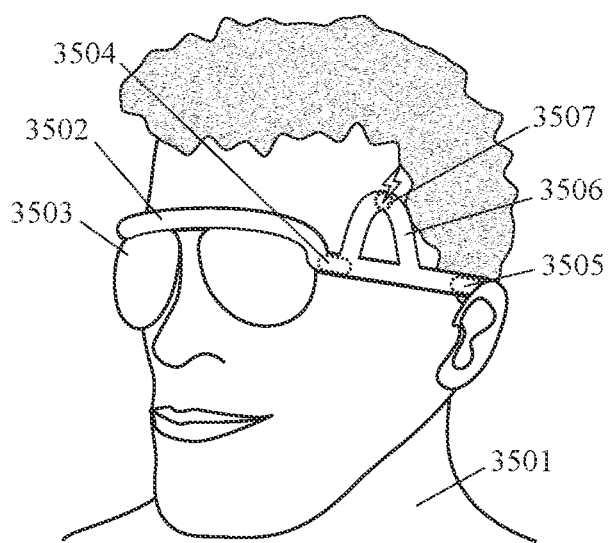
FIG. 35 shows EEG glasses with an arcuate bifurcating wave onto a person's forehead and/or temple.

FIG. 35 shows an example of eyewear for monitoring a person's electromagnetic brain activity comprising: at least one optical member which is configured to be held in proximity to an eye; a support member with at least one upward protrusion which is configured to span a portion of a person's forehead, temple, and/or a side of the person's head; and at least one electromagnetic brain activity sensor which is held in place by the upward protrusion. The example in FIG. 35 further comprises at least one imaging member and a data processing unit.

Specifically, FIG. 35 shows an example of eyewear for monitoring a person's (3501) electromagnetic brain activity comprising: at least one optical member (3503) which is configured to be held in proximity to an eye; a support member (3502) with at least one upward protrusion (3506) which is configured to span a portion of a person's forehead, temple, and/or a side of the person's head; and at least one electromagnetic brain activity sensor (3507) which is held in place by upward protrusion (3506). The example in FIG. 35 further comprises at least one imaging member (3504) and a data processing unit (3505).

In FIG. 35, upward protrusion 3506 ascends from a side portion of support member 3502. In this example, upward protrusion 3506 has a sinusoidal section shape. In an example, an upward protrusion can have a conic section shape. In this example, upward protrusion 3506 is one of two support member pathways which span from a person's ear to the front of the person's face. In this example, the other support member pathway is relatively straight. In this example, an electromagnetic energy sensor measures the conductivity, voltage, impedance, or resistance of electromagnetic energy transmitted through body tissue. In this example, electromagnetic brain activity sensor 3507 is an EEG sensor which is held in place by upward protrusion 3506. This example can include other component variations which were discussed earlier.

Figure 36:
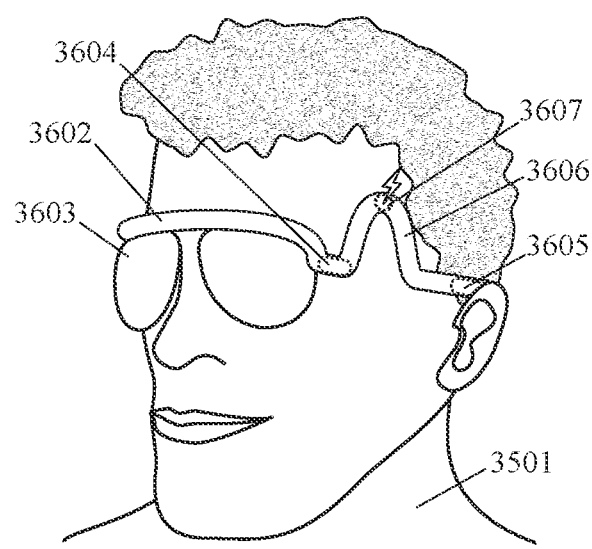
FIG. 36 shows EEG glasses with an arcuate upward wave onto a person's forehead and/or temple.

FIG. 36 shows an example of eyewear for monitoring a person's electromagnetic brain activity comprising: at least one optical member which is configured to be held in proximity to an eye; a support member with at least one upward protrusion which is configured to span a portion of a person's forehead, temple, and/or a side of the person's head; and at least one electromagnetic brain activity sensor which is held in place by the upward protrusion. The example in FIG. 36 further comprises at least one imaging member and a data processing unit.

Specifically, FIG. 36 shows an example of eyewear for monitoring a person's (3601) electromagnetic brain activity comprising: at least one optical member (3603) which is configured to be held in proximity to an eye; a support member (3602) with at least one upward protrusion (3606) which is configured to span a portion of a person's forehead, temple, and/or a side of the person's head; and at least one electromagnetic brain activity sensor (3607) which is held in place by upward protrusion (3606). The example in FIG. 36 further comprises at least one imaging member (3604) and a data processing unit (3605).

In FIG. 36, upward protrusion 3606 ascends from a side portion of support member 3602. In this example, upward protrusion 3606 has a sinusoidal section shape. In an example, an upward protrusion can have a conic section shape. In this example, upward protrusion 3606 is the sole pathway which spans from a person's ear to the front of the person's face. In this example, an electromagnetic energy sensor measures the conductivity, voltage, impedance, or resistance of electromagnetic energy transmitted through body tissue. In this example, electromagnetic brain activity sensor 3607 is an EEG sensor which is held in place by upward protrusion 3606. This example can include other component variations which were discussed earlier.

Figure 37:
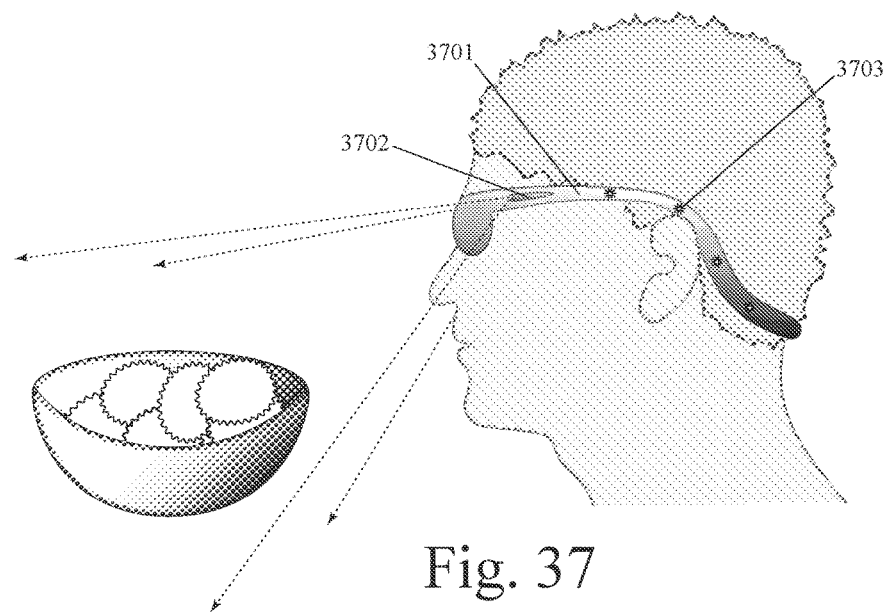
FIGS. 37 and 38 show how EEG glasses can be used to measure and/or modify a person's food consumption.
Figure 38:
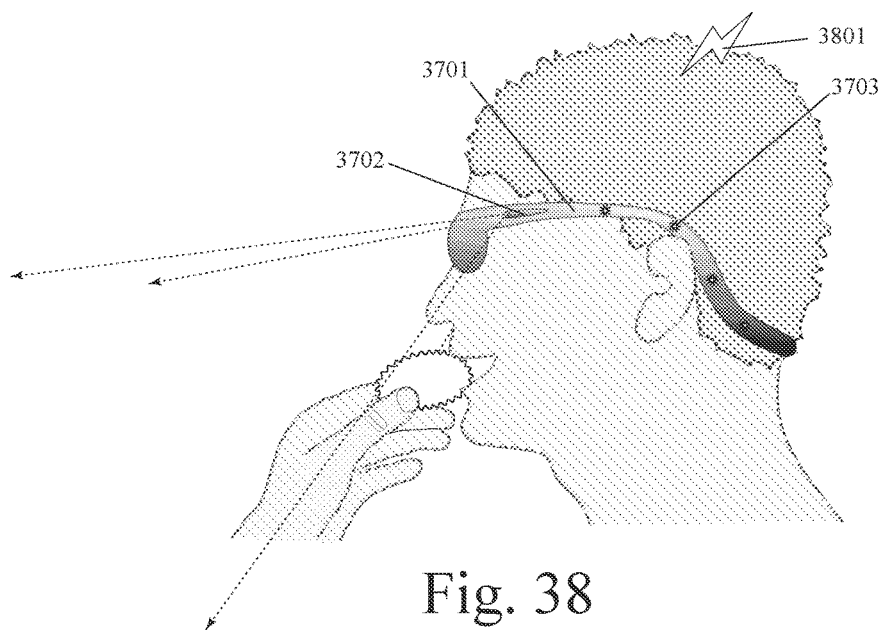

FIGS. 37 and 38 show an example of a device that doubles as eyewear and can be used to measure and/or modify a person's food consumption. In this example, wearable EEG monitor 3701 comprises a plurality of electrodes or other brain activity sensors (including 3703) and two wearable cameras (including 3702 shown on the left side). In this example, this device is assumed to be left-right symmetric, so a second camera is assumed to be on the right side of the person's head. In an example, wearable EEG monitor 3701 can further comprise a control unit. In an example, this control unit can comprise a power source, data processor, and data transmitter.

As shown in FIGS. 37 and 38, the anterior portion of wearable EEG monitor 3701 comprises an eyewear frame. In this example, this eyewear frame includes lenses. In an example, this eyewear frame can include a display surface instead of lenses. In an example, lenses can function as a display surface. In an example, this eyewear frame can be rigid, semi-rigid, or flexible.

As shown in FIGS. 37 and 38, the posterior portion of wearable EEG monitor 3701 comprises an arcuate member which loops around the lower-rear portion of the back of the person's head at a level which is equal to, or lower than, the person's ears. The sides of this device rest on top of the person's ears. In an example, this posterior arcuate portion of this device can have the same degree of rigidity, flexibility, and/or elasticity as the anterior eyewear frame portion of this device. In an example, this posterior arcuate portion of this device can have a higher degree of flexibility and/or elasticity than the anterior eyewear frame portion of this device. In an example, the anterior eyewear frame portion of this device can be made of metal and/or plastic and the posterior arcuate portion of this device can be made of fabric.

As shown in FIGS. 37 and 38, the two wearable cameras (including 3702 on the left side) of this device can take stereoscopic pictures of food when the person is looking at food (see FIG. 37) and when the person is eating food (see FIG. 38). In an example, having images of food both before and during consumption can enable more accurate identification of food type and more accurate measure of food quantity consumed. Also, stereoscopic imaging of food can enable 3D and volumetric modeling to better estimate the quantity of food consumed.

FIG. 38 shows a change 3801 in electromagnetic brain activity that is triggered when the person eats food. This change 3801 in electromagnetic brain activity is measured by wearable EEG monitor 3701. This change 3801 in brain activity based on food consumption is then linked to previously-identified patterns of food consumption and used to estimate the type and quantity of food consumed.

Figure 39:
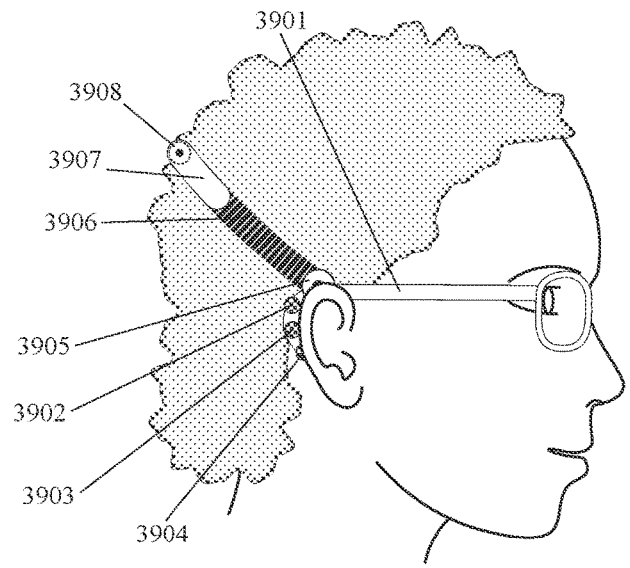
FIGS. 39 and 40 show two views of a first example of EEG glasses with a loop that moves onto a person's forehead.
Figure 40:
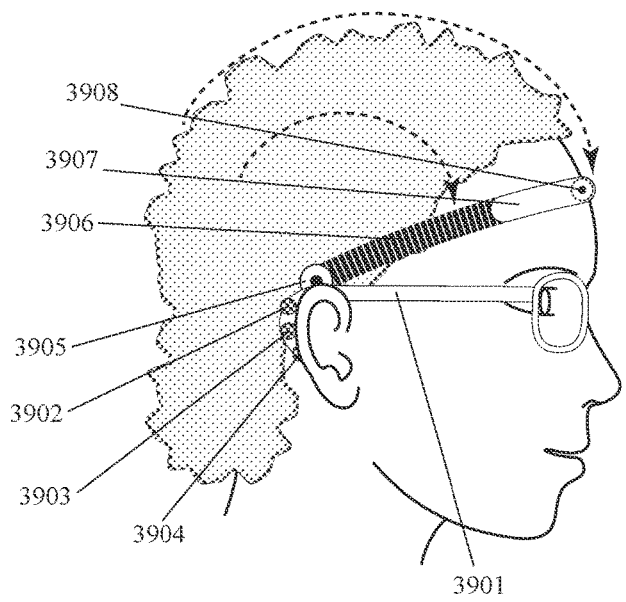

FIGS. 39 and 40 show two sequential views of a wearable device for measuring electromagnetic brain activity. FIG. 39 shows a view of this example at a first time wherein a movable loop with one or more electromagnetic energy sensors is configured to loop around the rear and/or upper-rear portion of a person's head. FIG. 40 shows a view of this example at a second time wherein the movable loop has been moved so that it is configured to loop around the person's forehead.

FIGS. 39 and 40 show an example of a wearable device for measuring electromagnetic brain activity comprising: eyewear 3901; a movable loop (including joint 3905, stretchable portion 3906, and end portion 3907), wherein this movable loop has a first configuration in which it loops around the rear and/or upper-rear portion of a person's head, wherein this movable loop has a second configuration in which is loops across the person's forehead, and wherein this movable loop can be reversibly moved from the first configuration to the second configuration; at least one electromagnetic energy sensor 3908 which is configured to be held in proximity to the person's forehead by the movable loop in the second configuration, wherein the electromagnetic energy sensor collects data concerning electromagnetic activity of the person's brain; a wireless data transmitter and/or receiver 3902; a data processor 3903; and a power source 3904. In an example, this device can have a symmetric configuration on the other side of the person's head, which is not shown here.

In an example, a movable loop can include a joint, hinge, or axle. In an example, a movable loop can pivot or rotate around a joint, hinge, or axle. In an example, the portion of a movable loop which is furthest from a person's ear can pivot or rotate around a joint, hinge, or axle which is within 1" of a person's ear. In an example, the portion of a movable loop which is furthest from a person's ear can pivot or rotate around a joint, hinge, or axle which is within 3" of a person's ear. In an example, a movable loop can be manually and reversibly moved from its first configuration to its second configuration. In an example, a joint, hinge, or axle can be reversibly locked or unlocked, so as to reversibly lock a movable loop in its first configuration or second configuration.

In an example, a movable loop can have a first configuration in which it loops around the rear and/or upper-rear portion of a person's head and a second configuration in which it loops around (across) a person's forehead. In an example, a movable loop can transition from its first configuration to its second configuration by pivoting or rotating around a joint, hinge, or axle. In an example, a movable loop can have a first configuration wherein its longitudinal axis is parallel to a vector between the 9 o'clock (270 degree) and 11 o'clock (330 degree) vectors and can have a second configuration wherein its longitudinal axis is parallel to a vector between the 1 o'clock (30 degree) and 3 o'clock (90 degree) vectors. In an example, a movable loop can have a first configuration wherein its longitudinal axis is parallel to a vector between the 10 o'clock (300 degree) and 12 o'clock (0 degree) vectors and can have a second configuration wherein its longitudinal axis is parallel to a vector between the 1 o'clock (30 degree) and 3 o'clock (90 degree) vectors.

In an example, a movable loop can be stretchable, elastic, and/or expandable. In an example, a movable loop can further comprise a first portion with a first degree of stretchability, elasticity, and/or expandability and a second portion with a second degree of stretchability, elasticity, and/or expandability, wherein the second degree is less than the first degree. In the example shown in FIGS. 39 and 40, the movable loop has a stretchable portion 3906 (with a greater degree of stretchability) and an end portion 3907 (with a lower degree of stretchability). Having at least one stretchable, elastic, and/or expandable portion of a movable loop allows the loop to be more easily moved from its first configuration to its second configuration. Having at least one stretchable, elastic, and/or expandable portion of a movable loop can also enable to loop to hold one or more electromagnetic energy sensors more securely against a person's forehead in the second configuration.

In an example, the stretchable portion of a movable loop can be an elastic band or strap. In an example, the stretchable portion of a movable loop can include a spring mechanism. In an example, a movable loop can include telescoping members. In an example, telescoping members can be held in tension by a spring mechanism so that they are compelled toward a contracted configuration in order to fit snugly against a person's head. In an example, a movable loop can have a first perimeter distance in a first configuration and a second perimeter distance in a second configuration, wherein the first distance is shorter than the second distance.

In an example, a movable loop and eyeglasses (or other eyewear) can be integral components of a single wearable device. In an example, a movable loop can be a separate device which is attached to eyeglasses (or other eyewear). In an example, a movable loop can be configured to receive the side frame of a pair of eyeglasses (or other eyewear). In an example, a movable loop can further comprise an opening which is configured to receive the side-piece of an eyeglass (or other eyewear) frame. In an example, a movable loop can further comprise a clip or other attachment mechanism to which the side-piece of an eyeglass (or other eyewear) frame can be attached. Other relevant variations and components discussed in other portions of this concurrent disclosure or prior disclosures incorporated herein by reference can also be applied to this example.

Figure 41:
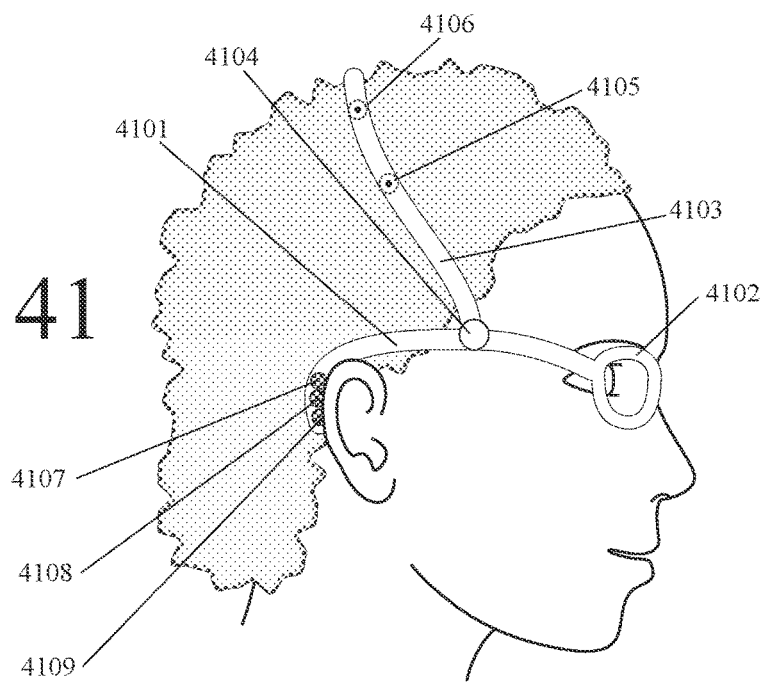
FIGS. 41 and 42 show two views of a second example of EEG glasses with a loop that moves onto a person's forehead.
Figure 42:
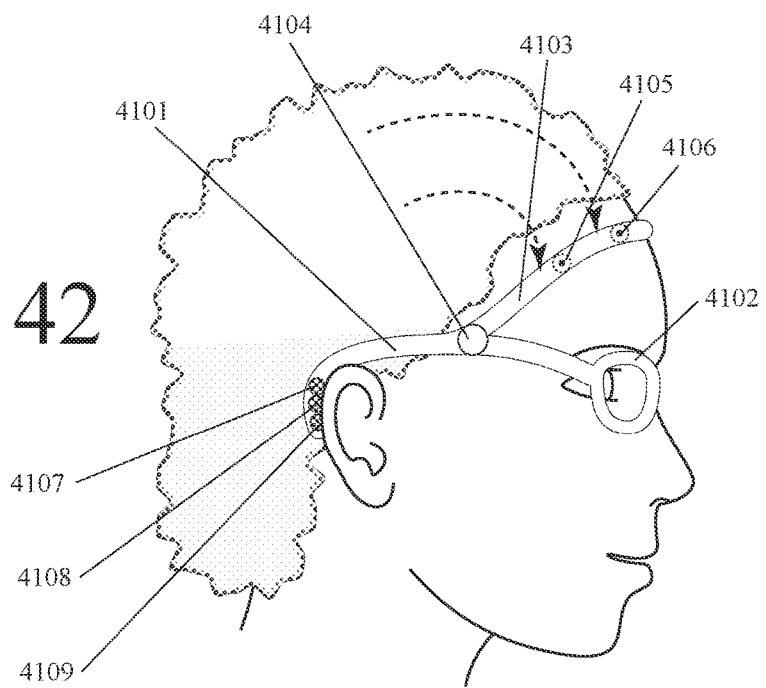

FIGS. 41 and 42 show two sequential views of a wearable and mobile Brain Computer Interface (BCI) comprising: eyewear which further comprises—a side frame (4101), a front frame (4102), a joint (4104) on the side frame, a movable loop (4103) which is configured to loop over the top of a person's head or around back of a person's head in a first configuration and which is configured to span across a person's forehead in a second configuration, wherein the movable loop pivots and/or rotates around the joint from the first configuration to the second configuration; one or more electromagnetic energy sensors (4105 and 4106) which are part of, or attached to, the movable loop, wherein these electromagnetic energy sensors collect data concerning electromagnetic brain activity; a power source (4107); a data processor (4108); and a data transmitter and/or receiver (4109). FIG. 41 shows this device when the movable loop is in the first configuration. FIG. 42 shows this device when the movable loop is in the second configuration. In an example, this device can be symmetric, with symmetric components and structure on the other side of the person's head.

Figure 43:
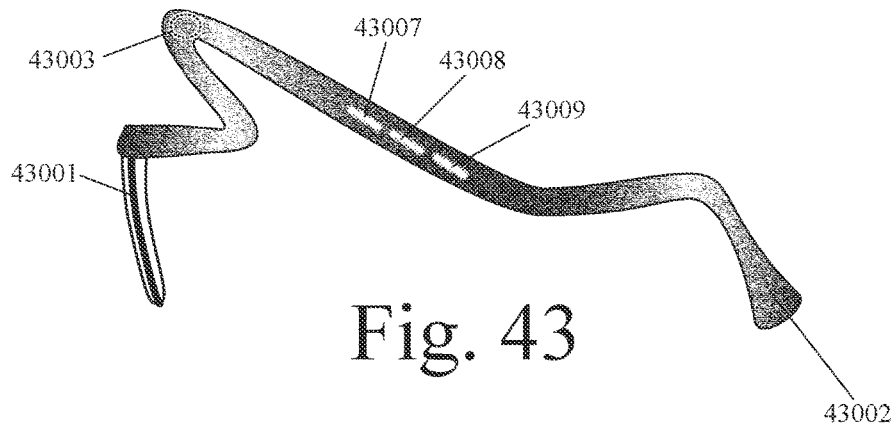
FIGS. 43 and 44 show two views of a first example of EEG glasses with a forward-backward loop over a person's forehead.
Figure 44:
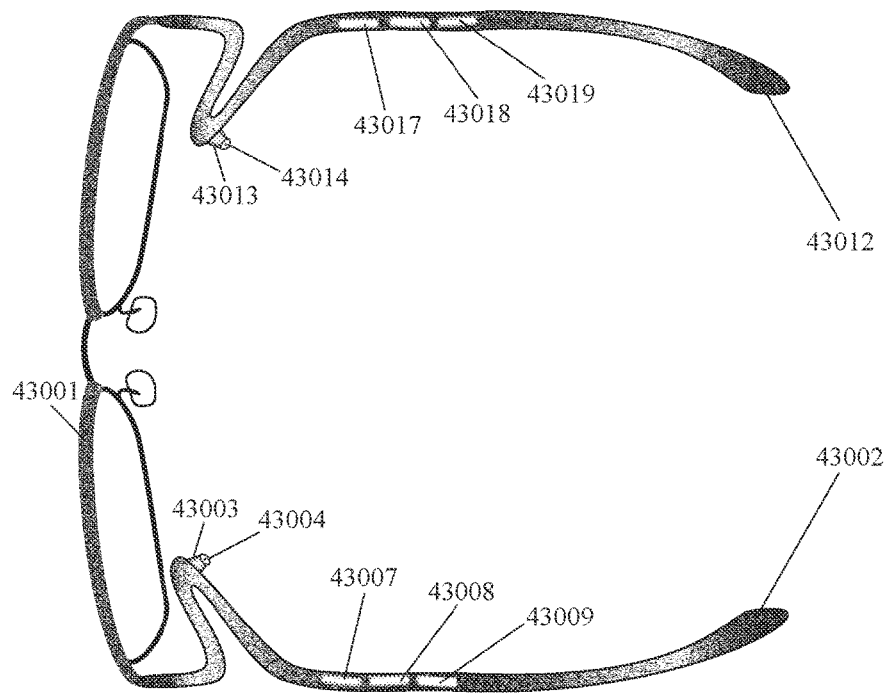

FIGS. 43 and 44 show side and top-down views, respectively, of an example of EEG glasses (electroencephalographic eyewear) comprising: (a) a front section of an eyewear frame which is configured to span the front of a person's face; (b) a side section of the eyewear frame which is configured to: span forward from one of the person's ears; then span upward, forward, and inward (toward the center of the person's forehead) to a location over the person's forehead (above one of the person's eyes); then span downward, backward, and outward (away from the center of the person's forehead); and then span forward to connect to the front section; and (c) at least one electromagnetic energy sensor which collects data concerning electromagnetic brain activity which is attached to the side section. In an example, the eyewear from can include a second side section with a similar configuration.

This example of EEG glasses (electroencephalographic eyewear) can also be described as comprising: (a) a front section of an eyewear frame which is configured to span the front of a person's face; (b) a side section of the eyewear frame which includes an upward loop which is configured to curve upward, forward, and inward (toward the center of the person's forehead) to a location over the person's forehead (above one of the person's eyes) and then curve downward, backward, and outward (away from the center of the person's forehead); and (c) at least one electromagnetic energy sensor which collects data concerning electromagnetic brain activity which is attached to the side section. In an example, the eyewear from can include a second side section with a similar configuration.

This example of EEG glasses (electroencephalographic eyewear) can also be described as comprising: (a) a front section of an eyewear frame which is configured to span the front of a person's face; (b) a side section of the eyewear frame with an arcuate zigzag portion, wherein this arcuate zigzag portion is configured to span forward (to a location over the person's forehead above one of the person's eyes), then span backward (to a location over the person's temple), and then span forward again (to connect to the front section); and (c) at least one electromagnetic energy sensor which collects data concerning electromagnetic brain activity which is attached to the side section. In an example, the eyewear from can include a second side section with a similar configuration.

This example of EEG glasses (electroencephalographic eyewear) can also be described as comprising: (a) a front section of an eyewear frame which is configured to span the front of a person's face; (b) a side section of the eyewear frame with an arcuate zigzag portion, wherein this arcuate zigzag portion is configured to span forward and upward (to a location over the person's forehead above one of the person's eyes), then span backward and downward, and then span forward (to connect to the front section); and (c) at least one electromagnetic energy sensor which collects data concerning electromagnetic brain activity which is attached to the side section. In an example, the eyewear from can include a second side section with a similar configuration.

This example of EEG glasses (electroencephalographic eyewear) can also be described as comprising: (a) a front section of an eyewear frame which is configured to span the front of a person's face; (b) a side section of the eyewear frame with an arcuate zigzag portion, wherein this arcuate zigzag portion is configured to span forward, upward, and inward toward the center of the person's forehead (to a location over the person's forehead above one of the person's eyes), then span backward, downward, and outward away from the center of the person's forehead, and then span forward (to connect to the front section); and (c) at least one electromagnetic energy sensor which collects data concerning electromagnetic brain activity which is attached to the side section. In an example, the eyewear from can include a second side section with a similar configuration.

With respect to specific components, FIGS. 43 and 44 show side and top-down views, respectively, of an example of EEG glasses (electroencephalographic eyewear) comprising: a front section 43001 of an eyewear frame; a first side section 43002 of the eyewear frame, wherein the first side section spans from one of the person's ears to the front section of the eyewear frame, wherein the first side section includes a loop which curves upward, forward, and inward (closer to the center of the person's forehead) to a location over the person's forehead (above an eye) and then curves downward, backward, and outward (farther from the center of the person's forehead); a first flexible protrusion 43003 on the first side section; a first electromagnetic energy sensor 43004 which collects data concerning electromagnetic brain activity on the first flexible protrusion; a first energy source 43007; a first data processor 43008; a first data transmitter and/or receiver 43009; a second side section 43012 of the eyewear frame, wherein the second side section spans from one of the person's ears to the front section of the eyewear frame, wherein the second side section includes a loop which curves upward, forward, and inward (closer to the center of the person's forehead) to a location over the person's forehead (above an eye) and then curves downward, backward, and outward (farther from the center of the person's forehead); a second flexible protrusion 43013 on the second side section; a second electromagnetic energy sensor 43014 which collects data concerning electromagnetic brain activity on the second flexible protrusion; a second energy source 43017; a second data processor 43018; and a second data transmitter and/or receiver 43019.

In this example, there is an energy source, a data processor, and a data transmitter and/or receiver on each side section. In an example, there can be an energy source, data processor, and data transmitter and/or receiver on only one side section. In an example, a flexible protrusion and/or an electromagnetic energy sensor can be attached to the portion of a side section which is located over the person's forehead above an eye. In this example, there is only one electromagnetic energy sensor on a side section. In an example, there can be two or more electromagnetic energy sensors on a side section. Other relevant components and design variations discussed elsewhere in this disclosure or priority-linked disclosures can also be incorporated into this example.

Figure 45:
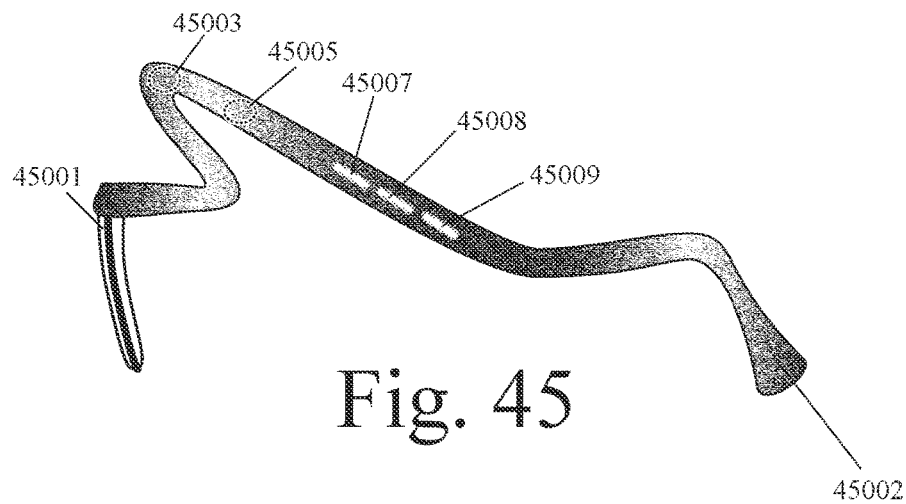
FIGS. 45 and 46 show two views of a second example of EEG glasses with a forward-backward loop over a person's forehead.
Figure 46:
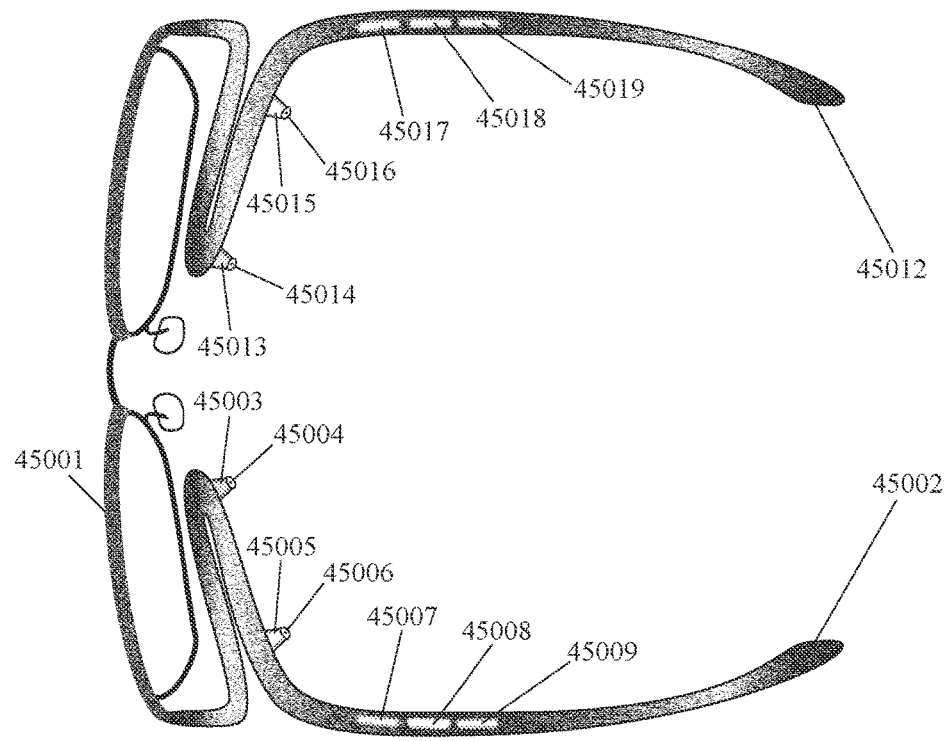

FIGS. 45 and 46 show an example of EEG glasses (electroencephalographic eyewear) which is similar to the example shown in FIGS. 43 and 44 except that: the side sections extend further inward toward the center of the person's forehead; and there are two electromagnetic energy sensors on each side section. In an example, inward loops of right-side and left-side sections may be separated by a distance of 5" or less (across a person's forehead). In an example, inward loops of right-side and left-side sections may be separated by a distance of 3" or less (across a person's forehead).

With respect to specific components, FIGS. 45 and 46 show side and top-down views, respectively, of an example of EEG glasses (electroencephalographic eyewear) comprising: a front section 45001 of an eyewear frame; a first side section 45002 of the eyewear frame, wherein the first side section spans from one of the person's ears to the front section of the eyewear frame, wherein the first side section includes a loop which curves upward, forward, and inward (closer to the center of the person's forehead) to a location over the person's forehead (above an eye) and then curves downward, backward, and outward (farther from the center of the person's forehead); first and second flexible protrusions 45003 and 45005 on the first side section; first and second electromagnetic energy sensors 45004 and 45006 which collect data concerning electromagnetic brain activity on the first flexible protrusion; a first energy source 45007; a first data processor 45008; a first data transmitter and/or receiver 45009; a second side section 45012 of the eyewear frame, wherein the second side section spans from one of the person's ears to the front section of the eyewear frame, wherein the second side section includes a loop which curves upward, forward, and inward (closer to the center of the person's forehead) to a location over the person's forehead (above an eye) and then curves downward, backward, and outward (farther from the center of the person's forehead); third and fourth flexible protrusions 45013 and 45015 on the second side section; third and fourth electromagnetic energy sensors 45014 and 45016 which collect data concerning electromagnetic brain activity on the second flexible protrusion; a second energy source 45017; a second data processor 45018; and a second data transmitter and/or receiver 45019. Other relevant components and design variations discussed elsewhere in this disclosure or priority-linked disclosures can also be incorporated into this example.

Figure 47:
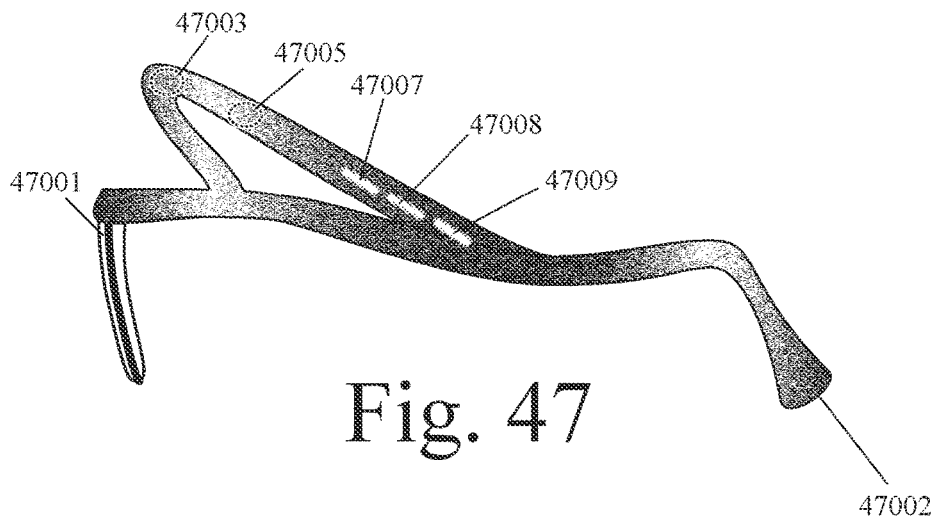
FIGS. 47 and 48 show two views EEG glasses with a side section bifurcation and a forward-backward loop over a person's forehead.
Figure 48:
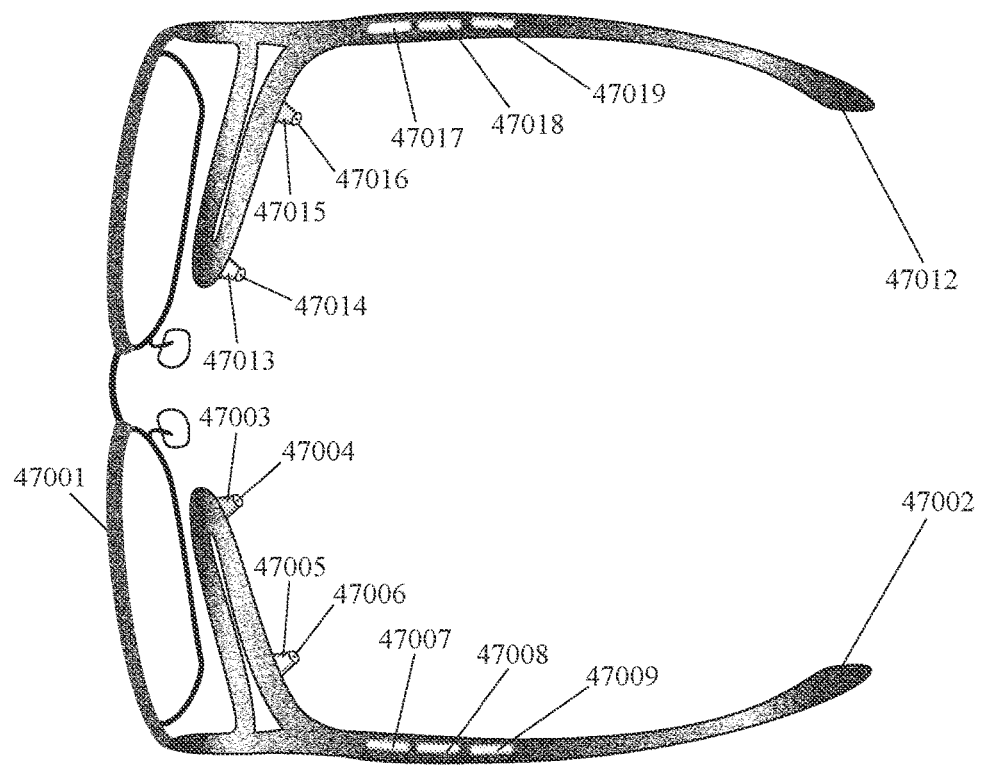

FIGS. 47 and 48 show an example of EEG glasses (electroencephalographic eyewear) which is similar to the example shown in FIGS. 45 and 46 except that the side sections each include a direct link which connects the ends of a forward-upward loop. This creates a bifurcation in a side section: with a first branch of the side section extending forward, upward, and inward to a location over the person's forehead; and a section branch of the side section extending in a relatively straight manner from the person's ear to the front sector of the eyewear frame.

With respect to specific components, FIGS. 47 and 48 show side and top-down views, respectively, of an example of EEG glasses (electroencephalographic eyewear) comprising: a front section 47001 of an eyewear frame; a first side section 47002 of the eyewear frame, wherein the first side section spans from one of the person's ears to the front section of the eyewear frame, wherein the first side section includes a loop which curves upward, forward, and inward (closer to the center of the person's forehead) to a location over the person's forehead (above an eye) and then curves downward, backward, and outward (farther from the center of the person's forehead); first and second flexible protrusions 47003 and 47005 on the first side section; first and second electromagnetic energy sensors 47004 and 47006 which collect data concerning electromagnetic brain activity on the first flexible protrusion; a first energy source 47007; a first data processor 47008; a first data transmitter and/or receiver 47009; a second side section 47012 of the eyewear frame, wherein the second side section spans from one of the person's ears to the front section of the eyewear frame, wherein the second side section includes a loop which curves upward, forward, and inward (closer to the center of the person's forehead) to a location over the person's forehead (above an eye) and then curves downward, backward, and outward (farther from the center of the person's forehead); third and fourth flexible protrusions 47013 and 47015 on the second side section; third and fourth electromagnetic energy sensors 47014 and 47016 which collect data concerning electromagnetic brain activity on the second flexible protrusion; a second energy source 47017; a second data processor 47018; and a second data transmitter and/or receiver 47019. Other relevant components and design variations discussed elsewhere in this disclosure or priority-linked disclosures can also be incorporated into this example.

Figure 49:
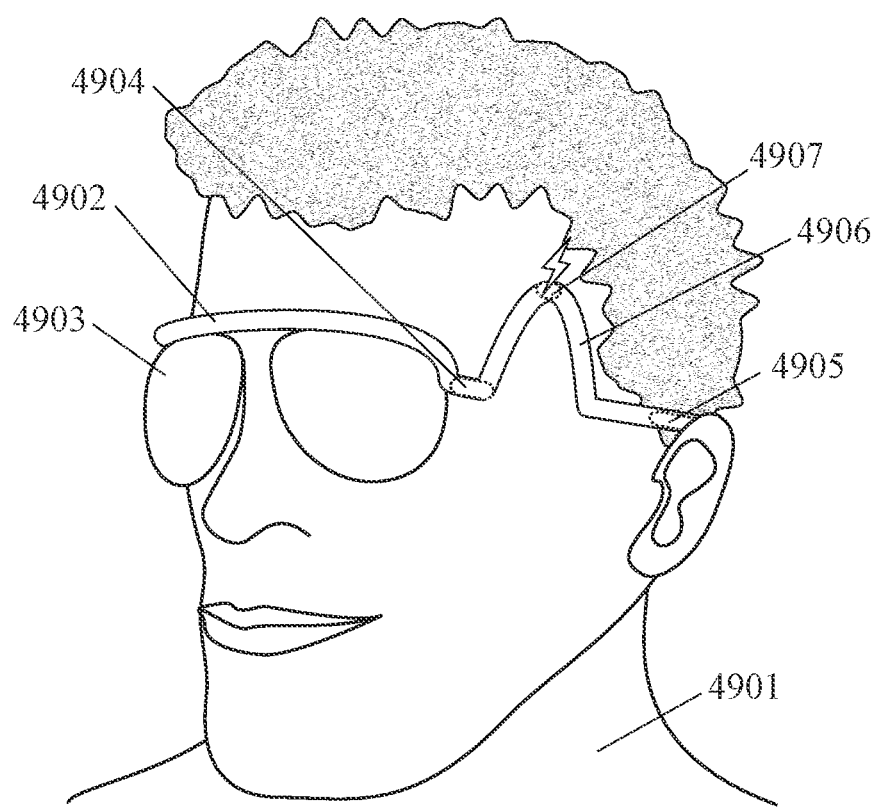
FIG. 49 shows EEG glasses with a conic section upward wave onto a person's forehead and/or temple.

FIG. 49 shows EEG glasses with a conic section upward wave onto a person's forehead and/or temple. FIG. 49 shows an example of eyewear for monitoring a person's electromagnetic brain activity comprising: at least one optical member which is configured to be held in proximity to an eye; a support member with at least one upward protrusion which is configured to span a portion of a person's forehead, temple, and/or a side of the person's head; and at least one electromagnetic brain activity sensor which is held in place by the upward protrusion. The example in FIG. 49 further comprises at least one imaging member and a data processing unit.

Specifically, FIG. 49 shows an example of eyewear for monitoring a person's (4901) electromagnetic brain activity comprising: at least one optical member (4903) which is configured to be held in proximity to an eye; a support member (4902) with at least one upward protrusion (4906) which is configured to span a portion of a person's forehead, temple, and/or a side of the person's head; and at least one electromagnetic brain activity sensor (4907) which is held in place by upward protrusion (4906). The example in FIG. 49 further comprises at least one imaging member (4904) and a data processing unit (4905).

In FIG. 49, upward protrusion 4906 ascends from a side portion of support member 4902. In this example, upward protrusion 4906 has a conic section shape. In this example, upward protrusion 4906 is the sole pathway which spans from a person's ear to the front of the person's face. In this example, an electromagnetic energy sensor measures the conductivity, voltage, impedance, or resistance of electromagnetic energy transmitted through body tissue. In this example, electromagnetic brain activity sensor 4907 is an EEG sensor which is held in place by upward protrusion 4906. This example can include other component variations which were discussed earlier.

In an example, the side frame of eyewear can be configured to span from a person's ear to a front frame. In an example, a rear portion of a side frame can curve around the rear of the person's outer ear. In an example, a side frame can be arcuate. In an example, a portion of a side frame between a person's ear and a front frame can arc, curve, wave, and/or undulate upwards. In an example, a side frame can have a downward-facing concave portion. In an example, a front frame of eyewear can hold one or more lenses. In an example, this eyewear can be a pair of eyeglasses. In an example, the front frame of eyewear can hold one or more image displays. In an example, this eyewear can be virtual reality (VR) and/or augmented reality (AR) eyewear.

In an example, the joint around which a movable loop pivots and/or rotates can be located along the (rear to front) longitudinal mid-section of a side frame. In an example, a joint can be located within 2" of the longitudinal mid-point of a side frame. In an example, a joint around which a movable loop pivots and/or rotates can be located along the rear third of a side frame. In an example, a joint can be located within 2" of the rear end a side frame. In an example, a joint can further comprise a locking mechanism which locks it in place when a movable loop is at a selected angle and/or in a selected position. In an example, a joint can have restricted movement such that it restricts the movement of a movable loop so that the loop does not descend lower than a selected position on a person's forehead.

In an example, a movable loop can be made out of metal or a polymer. In an example, a movable loop can be flexibly resilient. In an example, a movable loop can be made out of fabric. In an example, a movable loop can be elastic, stretchable, and/or expandable. In an example, a movable loop can further comprise an elastic, stretchable, and/or expandable portion. In an example, a movable loop can further comprise a telescoping portion. In an example, a movable loop holds one or more electromagnetic energy sensors on a person's forehead when the loop is in the second configuration. Other relevant variations and components discussed in other portions of this concurrent disclosure or prior disclosures incorporated herein by reference can also be applied to this example.

In an example, an electromagnetic energy sensor for collecting data concerning electromagnetic brain activity can be an electroencephalographic (EEG) sensor. In an example, an electromagnetic energy sensor can be an electrode. In an example, an electromagnetic energy sensor can be a dry electrode. In an example, there can be two or more electromagnetic energy sensors which collect data concerning electromagnetic brain activity.

In an example, one or more electromagnetic energy sensors can be modular. In an example, one or more electromagnetic energy sensors can be removably attached. In an example, a device can comprise a first number of electromagnetic energy sensors and a second number of locations where electromagnetic energy sensors can be attached, wherein the second number is greater than the first number. In an example, one or more electromagnetic energy sensors can be removably attached by one or more attachment mechanisms selected from the group consisting of: magnetic attachment; hook-and-eye fabric; protrusion and opening; snap; clip; clasp; hook; buckle; plug attachment; pin; button; thread and groove; tongue and groove.

In an example, data concerning a person's brain activity can be collected by one or more electromagnetic energy sensors at one or multiple selected recording sites. In an example, the locations of one or more electromagnetic energy sensors can be selected from the group of EEG placement sites consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, one or more reference places can be selected from the group of sites consisting of A1 and A2.

In an example, collection of data concerning brain activity can comprise measuring electromagnetic data concerning impedance, voltage difference, and/or energy transfer between two sites on a person's head—a selected recording site and a reference site. In an example, electromagnetic brain activity data can be collected by an electromagnetic energy sensor at a selected recording place. In an example, electromagnetic brain activity data from a selected recording place (relative to a reference place) can be called a "channel" In an example, electromagnetic brain activity data from multiple recording places can be called a "montage." In an example, brain activity data can be recorded at a rate in the range of 100 to 300 samples per second.

In an example, a statistical method can be used to identify specific patterns in a person's electromagnetic brain activity and/or specific changes in a person's electromagnetic brain activity. In an example, data from one or more electromagnetic energy sensors can be filtered to remove artifacts before the application of a statistical method. In an example, a filter can be used to remove electromagnetic signals from eye blinks, eye flutters, or other eye movements before the application of a statistical method. In an example, a notch filter can be used as well to remove 60 Hz artifacts caused by AC electrical current. In various examples, one or more filters can be selected from the group consisting of: a high-pass filter, a band-pass filter, a loss-pass filter, an electromyographic activity filter, a 0.5-1 Hz filter, and a 35-70 Hz filter.

In an example, a pattern and/or change in electromagnetic brain activity can be a one-time pattern. In another example, a pattern of electromagnetic brain activity can repeat over time in a rhythmic manner. In an example, a primary statistical method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods.

In an example, a primary statistical method for identifying patterns and/or changes in electromagnetic brain activity can comprise finding the mean or average value of data from one or more brain activity channels during a period of time. In an example, a statistical method can comprise identifying a significant change in the mean or average value of data from one or more brain activity channels. In an example, a statistical method can comprise finding the median value of data from one or more brain activity channels during a period of time. In an example, a statistical method can comprise identifying a significant change in the median value of data from one or more brain activity channels. In an example, a statistical method can comprise identifying significant changes in the relative mean or median data values among multiple brain activity channels. In an example, a statistical method can comprise identifying significant changes in mean data values from a first set of sensor locations relative to mean data values from a second set of sensor locations. In an example, a statistical method can comprise identifying significant changes in mean data recorded from a first region of the brain relative to mean data recorded from a second region of the brain.

In an example, a primary statistical method for identifying patterns and/or changes in electromagnetic brain activity can comprise finding the minimum or maximum value of data from one or more brain activity channels during a period of time. In an example, a statistical method can comprise identifying a significant change in the minimum or maximum value of data from one or more brain activity channels. In an example, a statistical method can comprise identifying significant changes in the relative minimum or maximum data values among multiple brain activity channels. In an example, a statistical method can comprise identifying significant changes in minimum or maximum data values from a first set of sensor locations relative to minimum or maximum data values from a second set of sensor locations. In an example, a statistical method can comprise identifying significant changes in minimum or maximum data values recorded from a first region of the brain relative to minimum or maximum data values recorded from a second region of the brain.

In an example, a primary statistical method for identifying patterns and/or changes in electromagnetic brain activity can comprise finding the variance or the standard deviation of data from one or more brain activity channels during a period of time. In an example, a statistical method can comprise identifying a significant change in the variance or the standard deviation of data from one or more brain activity channels. In an example, a statistical method can comprise identifying significant changes in the covariation and/or correlation among data from multiple brain activity channels. In an example, a statistical method can comprise identifying significant changes in the covariation or correlation between data from a first set of sensor locations relative and data from a second set of sensor locations. In an example, a statistical method can comprise identifying significant changes in the covariation or correlation of data values recorded from a first region of the brain and a second region of the brain.

In an example, a primary statistical method for identifying patterns and/or changes in electromagnetic brain activity can comprise finding the amplitude of waveform data from one or more channels during a period of time. In an example, a statistical method can comprise identifying a significant change in the amplitude of waveform data from one or more channels. In an example, a statistical method can comprise identifying significant changes in the relative wave amplitudes from one or more channels. In an example, a statistical method can comprise identifying significant changes in the amplitude of electromagnetic signals recorded from a first region of the brain relative to the amplitude of electromagnetic signals recorded from a second region of the brain.

In an example, a primary statistical method for identifying patterns and/or changes in electromagnetic brain activity can comprise finding the power of waveform brain activity data from one or more channels during a period of time. In an example, a statistical method can comprise identifying a significant change in the power of waveform data from one or more channels. In an example, a statistical method can comprise identifying significant changes in the relative power levels of one or more channels. In an example, a statistical method can comprise identifying significant changes in the power of electromagnetic signals recorded from a first region of the brain relative to the power of electromagnetic signals recorded from a second region of the brain.

In an example, a primary statistical method for identifying patterns and/or changes in electromagnetic brain activity can comprise finding a frequency or a frequency band of waveform and/or rhythmic brain activity data from one or more channels which repeats over time. In an example, Fourier Transform methods can be used to find a frequency or a frequency band of waveform and/or rhythmic data which repeats over time. In an example, a statistical method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a primary statistical method for identifying patterns and/or changes in electromagnetic brain activity can comprise identifying significant changes in the amplitude, power level, phase, frequency, covariation, entropy, and/or oscillation of waveform data from one or more channels. In an example, a statistical method can comprise identifying significant changes in the amplitude, power level, phase, frequency, covariation, entropy, and/or oscillation of waveform data within a selected frequency band. In an example, a statistical method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, Delta brainwaves can be measured and analyzed within a frequency band of 1 to 4 Hz. In various examples, Delta brainwaves or other rhythmic, cyclical, and/or repeating electromagnetic signals associated with brain activity can be measured and analyzed within a frequency band selected from the group consisting of: 0.5-3.5 Hz, 0.5-4 Hz, 1-3 Hz, 1-4 Hz, and 2-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific sensor site, a specific sensor channel, and/or a specific montage of channels.

In an example, Theta brainwaves can be measured and analyzed within a frequency band of 4 to 8 Hz. In various examples, Theta brainwaves or other rhythmic, cyclical, and/or repeating electromagnetic signals associated with brain activity can be measured and analyzed within a frequency band selected from the group consisting of: 3.5-7 Hz, 3-7 Hz, 4-7 Hz, 4-7.5 Hz, 4-8 Hz, and 5-7 Hz. In an example, a method can track changes in the power of brainwaves in the Theta band. In an example, a method can track a frequency shift within the Theta band. In an example, a method can track changes in wave shape for brainwaves in the Theta band. In an example, a method can track a change in which brain regions originate or modify brainwaves within the Theta band. In an example, a method can track a change in brainwave activity within the Theta band as measured from a specific sensor site, a specific sensor channel, and/or a specific montage of channels.

In an example, Alpha brainwaves can be measured and analyzed within a frequency band of 7 to 14 Hz. In various examples, Alpha brainwaves or other rhythmic, cyclical, and/or repeating electromagnetic signals associated with brain activity can be measured and analyzed within a frequency band selected from the group consisting of: 7-13 Hz, 7-14 Hz, 8-12 Hz, 8-13 Hz, 7-11 Hz, 8-10 Hz, and 8-10 Hz. In an example, a method can track an increase or decrease in the relative power of brainwaves in the Alpha band. In an example, a method can track a downward or upward shift in the frequency of brainwaves within the Alpha band. In an example, a method can track a change in wave shape for brainwaves in the Alpha frequency band. In an example, a method can track a change in which brain regions originate or modify brainwaves within the Alpha frequency band. In an example, a method can track a change in brainwave activity within the Alpha band on one side of a person's brain relative to the other side. In an example, a method can track a change in brainwave activity within the Alpha band in a particular brain lobe or organelle. In an example, a method can track a change in brainwave activity within the Alpha band as measured from a specific sensor site, a specific sensor channel, and/or a specific montage of channels.

In an example, Beta brainwaves can be measured and analyzed within a frequency band of 12 to 30 Hz. In various examples, Beta brainwaves or other rhythmic, cyclical, and/or repeating electromagnetic signals associated with brain activity can be measured and analyzed within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. In an example, specific patterns or trends in brainwaves in the Beta frequency band can be statistically identified.

In an example, Gamma brainwaves can be measured and analyzed within a frequency band of 30 to 100 Hz. In various examples, Gamma brainwaves or other rhythmic, cyclical, and/or repeating electromagnetic signals associated with brain activity can be measured and analyzed within a frequency band selected from the group consisting of: 30-100 Hz, 35-100 Hz, 40-100 Hz, and greater than 30 Hz. In an example, specific patterns or trends in brainwaves in the Gamma frequency band can be statistically identified.

In an example, a primary statistical method can employ multivariate analysis of electromagnetic brainwave activity in the Delta, Theta, and Alpha frequency bands to identify patterns. In an example, a primary statistical method can comprise calculating an arithmetic function, or a change in an arithmetic function, of the different power levels in multiple frequency bands. In an example, a primary statistical method can comprise a difference, or a change in a difference, between power levels in different frequency bands. In an example, a primary statistical method can comprise a ratio, or a change in a ratio, of power levels in different frequency bands. In an example, a primary statistical method can comprise a sum, or a change in a sum, of power levels in different frequency bands. In an example, a primary statistical method can comprise a product, or a change in a product, of power levels in different frequency bands.

In various examples, specific patterns of electromagnetic brain activity can be analyzed and identified using one or more methods selected from the group consisting of: ANOVA or MANOVA; artificial neural network; auto-regression; Bonferroni analysis; Carlavian curve analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method.

In an example, a power source for this device can comprise a rechargeable battery. In an example, a power source can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy.

In an example, a data processing unit can process data from one or more electromagnetic energy sensors. In an example a data processing unit can be a microchip, circuit board, CPU, and/or miniature computer. In an example, a data transmitter and/or receiver can be a wireless data transmitter and/or receiver. In an example, data transmitter and/or receiver can be in wireless communication with a remote computer, a handheld electronic device, a separate wearable device, a separate array of wearable sensors, a communication network tower, a satellite, a home control system, and/or an implantable medical device.

I claim:

1. A pair of eyeglasses which collects data concerning electromagnetic energy from a person's brain comprising:
   a front portion of a frame of the pair of eyeglasses which is configured to be worn on the person's head and to span from one eye to the other eye across a portion of the front of the person's face;
   at least one optical lens which is configured to be worn within 6" of one of the person's eyes and which is attached to or an integrated part of the front portion of the frame of the pair of eyeglasses;
   at least one side portion of the frame of the pair of eyeglasses which is attached to or an integrated part of the front portion of the frame of the pair of eyeglasses and which is configured to be worn on or around one of the person's ears, wherein a middle section of the side portion of the frame of the pair of eyeglasses is shaped like a conic section;
   an electromagnetic energy sensor which is attached to or an integrated part of the middle section of the side portion of the frame of the pair of eyeglasses and which is configured to receive electromagnetic energy from the person's brain; and a control unit with which the at least one electromagnetic energy sensor is in electromagnetic communication.

* * * * *